United States Patent [19]
Mezes et al.

[11] Patent Number: 5,976,845
[45] Date of Patent: Nov. 2, 1999

[54] COMPOSITE ANTIBODIES OF HUMAN SUBGROUP IV LIGHT CHAIN CAPABLE OF BINDING TO TAG-72

[75] Inventors: Peter S. Mezes, Oldlyme, Conn.; Ruth A. Richard, Midland, Mich.; Kimberly S. Johnson, New London, Conn.

[73] Assignee: The Dow Chemical Company, Midland, Mich.

[21] Appl. No.: 08/487,743

[22] Filed: Jun. 7, 1995

Related U.S. Application Data

[60] Division of application No. 08/261,354, Jun. 16, 1994, which is a continuation-in-part of application No. 07/964,536, Oct. 20, 1992, abandoned, and a continuation-in-part of application No. 07/510,697, Jul. 17, 1990, abandoned.

[51] Int. Cl.$^6$ ............................. C12N 15/07; C07K 16/30
[52] U.S. Cl. ...................... 435/172.2; 435/328; 435/344; 530/387.3; 530/387.7; 530/388.8; 424/133.1; 424/138.1
[58] Field of Search ............................... 530/387.3, 387.7, 530/388.8; 424/130.1, 133.1, 138.1; 435/172.2, 328, 344

[56] References Cited

U.S. PATENT DOCUMENTS

| | | |
|---|---|---|
| 4,642,334 | 2/1987 | Moore et al. |
| 4,656,134 | 4/1987 | Ringold |

FOREIGN PATENT DOCUMENTS

| | | |
|---|---|---|
| 8943540 | 4/1990 | Australia |
| 8900692 | 6/1988 | WIPO |
| 8901783 | 3/1989 | WIPO |
| 9004410 | 10/1989 | WIPO |

OTHER PUBLICATIONS

Jones et al. (1986), Nature, 321:522–525.
Brown et al. (1987), Cancer Research, 47:3577–3583.
Marsh et al, Nucleic Acids Research, 13:6531–6544, (1985).
Polke et al, Immunobiol., 163:95–109, (1982).
Klobeck et al., Nucleic Acids Research, 13:6516–6528, (1985).
Clackson et al., Nature, 352:624–628, (1991).
Huse et al., Science, 246: 1275–1281, (1989).
Whittle et al., Protein Engineering, 6:499–505, (1987).
Brady et al., J. Mol. Biol., 219:603–604, (1991).
Riechmann et al., Nature, 332: 323–327, (1988).
Colcher et al., Cancer Research, 49:1738–1745, (1989).
Sheer et al., Cancer Research, 48:6811–6818, (1988).
Harris et al., Tib Tech, 11:42–44, (1993).
Waldman, Science, 252:1657–1660, (1991).
Primus et al., Cancer Immunol Immunother, 31:249–257, (1990).
Neeleman and Wunsch, A General Method Applicable to the Search for Similarities in the Amino Acid Sequence of Two Proteins, J.Mol. Biol. 48:443–453 (1970).
Pearson and Lipman, Improved tools for biological sequence comparison, Proc. Natl. Acad. Sci, USA, 85:2444–2448 (1988).

*Primary Examiner*—Thomas M. Cunningham
*Attorney, Agent, or Firm*—Karen L. Kimble; Mark S. Scott

[57] ABSTRACT

This invention concerns a subset of composite Hum4 $V_L$, $V_H$ antibodies with high affinities to a high molecular weight, tumor-associated sialylated glycoprotein antigen (TAG-72) of human origin. These antibodies have variable regions with (1) $V_L$ segments derived from the human subgroup IV germline gene, and (2) a $V_H$ segment which is capable of combining with the $V_L$ to form a three dimensional structure having the ability to bind TAG-72. In vivo methods of treatment and diagnostic assay using these composite antibodies is also disclosed.

19 Claims, 64 Drawing Sheets

FIG. 2A

```
VHαTAG      TCTCTTCCTC CACCACCAAA TCCACCATTT GTAAATCAAC CCT
CC49        .......... .......... .......... .......... ...
CC83        .......... .......... .......... .......... ...

VHαTAG      ATGTTAACAT ATCACAGAGT GGAGCAACAG AATCAGGGCA
CC49        .......... .......... .......... ..........
CC83        .......... .......... .......... ..........

VHαTAG      AAAATATGCT GAGAGATTTA TCCCTGTCGT TACAACCAAA
CC49        .......... .........T .......... ..........
CC83        .......... .......... .......... ..........

VHαTAG      GCATCTGTCT AGAATTCATA AAAACTTTAT GGGATACATT
CC49        .......... .......... .......... ..........
CC83        .......... .......... .......... ..........

VHαTAG      TCCTCAGAGA GGAATAGGAT TTGGACCTGA CGATCCTGCT
CC49        .......... .......... .......... ..........
CC83        .......... .......... .......... ..........
```

FIG. 2B

```
         GCCCGAGCCA TGTGATGACA GTTCTTCTCC AGTTGAACTA
VHαTAG   .......... .......... .......... ..........
CC49     .......... .......... .......... ..........
CC83     .......... .......... .......... ..........

GGTCCTTATC TAAGAAATGC ACTGCTCATG AATATGCAAA
VHαTAG   .......... .......... .......... ..........
CC49     .......... .......... .......... ..........
CC83     .......... .......... .......... ..........

TCACCCGAGT CTATGGCAGT AAATACAGAG ATGTTCATAC
VHαTAG   .......... .......... .......... ..........
CC49     .......... .......... .......... ..........
CC83     .......... .......... .......... ..........

CATAAAAACA ATATATGATC AGTGTCTTCT CCGCTATCCC
VHαTAG   .......... .......... .......... ..........
CC46     .......... .......... .......... ..........
CC49     .......... ....G..... .......... ..........
CC83     .......... .......... .......... ..........
CC92     .......... .......... .......... ..........
```

FIG. 2C

```
V_H αTAG   TGGACACACT GACTCTAACC ATG GAA TGG AGC TGG
CC46       .......... .......... ... ... ... ... ...
CC49       .......... .......... ... ... ... ... ...
CC83       .......... .......... ... ... ... ... ...
CC92       .......... .......... ... ... ... ... ...

V_H αTAG   GTC TTT CTC TTC CTG TCA GTA ACT ACA G
CC46       ... ... ... ... ... ... ... ... ... .
CC49       ... ... ... ... ... ... ... ... ... .
CC83       ... ... ... ... ... ... ... ... ... .
CC92       ... ... ... ... ... ... ... ... ... .

V_H αTAG   GTAAGGGGCT CACCATTTCC AAATCTAAAG TGGAGTCAGG
CC46       .......... .......... .......... ..........
CC49       .......... .......... .......... ..........
CC83       .......... .......... .......... ..........
CC92       .......... .......... .......... ..........
```

FIG. 2D

```
VHαTAG   GCCTGAGGTG ACAAAGATAT CACCTTTGGC TTTCCACAG
CC46     .......... .......... .......... .........
CC49     .......... ......G... .......... ....G....
CC83     .......... .......... .......... .........
CC92     .......... .......... .......... .........

VHαTAG   GT GTC CAC TCC CAG GTT CAG CAG CTG CAG CAG TCT
CC46     .. ... ... ... ... ... ... ... ... ... ... ...
CC49     .. ... ... ... ..A T.. ... ... ... ... ... ...
CC83     .. ... ... ... ... ... ... ... .T. ..A ... ...
CC92     .. ... ... ... ... ... ... ... .T. ... ... ...

VHαTAG   GAC GCT GAG TTG GTG AAA CCT GGG GCT TCA GTG
CC46     ... ... ... ... ... ... ... ... ... ... ...
CC49     ... ... ... ... ... ..G ... ... ... ... ...
CC83     ... ... ... ... ... ... ... ... ... ... ...
CC92     ... ... ... ... ... ... ... ... ... ... ...
```

FIG. 2E

|       | | | | | | | | | | | |
|-------|---|---|---|---|---|---|---|---|---|---|---|
| VHαTAG | AAG | ATA | TCC | TGC | AAG | GCT | TCT | GGC | TAC | ACC | TTC |
| CC46  | . | .T. | . | . | . | . | . | . | . | . | . |
| CC49  | . | .T. | . | . | . | . | . | . | . | . | . |
| CC83  | . | .T. | . | . | . | . | . | . | . | . | . |
| CC92  | . | . | . | . | . | . | . | . | . | . | . |

<-------- CDR1 -------->

|       | | | | | | | | | | | |
|-------|---|---|---|---|---|---|---|---|---|---|---|
| VHαTAG | ACT | GAC | CAT | GCT | ATT | CAC | TGG | GTG | AAG | CAG | AAG |
| CC46  | . | . | . | . | .A. | . | . | . | . | . | ..C |
| CC49  | . | . | . | . | . | . | . | . | .A. | . | . |
| CC83  | . | . | . | . | . | . | . | . | . | . | . |
| CC92  | . | . | . | . | . | . | . | . | . | . | ..A |

|       | | | | | | | | | | | |
|-------|---|---|---|---|---|---|---|---|---|---|---|
| VHαTAG | CCT | GAA | CAG | GGC | CTG | GAA | TGG | ATT | GGA | TAT | ATT |
| CC46  | . | . | . | . | . | . | . | . | . | T.. | . |
| CC49  | . | . | . | . | . | . | . | . | . | T.. | . |
| CC83  | . | . | . | . | . | . | . | . | . | . | . |
| CC92  | . | . | . | . | . | . | . | . | . | . | . |

<-------- CDR2

|       | | | | | | | | | | | |
|-------|---|---|---|---|---|---|---|---|---|---|---|
| VHαTAG | TCT | CCC | GGA | AAT | GGT | GAT | ATT | AAG | TAC | AAT | GAG |
| CC46  | . | . | . | . | .A. | . | .T. | . | . | . | . |
| CC49  | . | . | . | . | .A. | . | . | . | ..A | . | . |
| CC83  | . | . | . | . | .A. | . | . | . | . | . | . |
| CC92  | . | . | . | . | . | . | . | . | . | . | . |

FIG. 2F

```
                ←——— CDR2 ———→
V_H αTAG    AAG TTC AAG GGC  AAG GCC ACA CTG ACT GCA GAC
CC46        .G. ... ... ...  ... ... ... ... ... ... ...
CC49        ... ... ... ...  ... ... ... ... ... ... ...
CC83        ... ... ... ..T  ... ... ... ... ... ... ...
CC92        ... ... ... ...  ... ... ... ... ... ... ...

V_H αTAG    AAA TCC TCC AGC ACT GCC TAC ATG CAG CTC AAC
CC46        ... ... ... ... ... ... ... ... ... ... ...
CC49        ... ... ... ..T ... ... ... .G. ... T.. ...
CC83        ... ..C .A. ... ... ..T ... ... ..A ... ...
CC92        ... ... ... ... ... ... ... ... ... ... ...

V_H αTAG    AGC CTG ACA TCT GAG GAT TCT GCA GTG TAT TTC
CC46        ... ... ... ... ... ..C ... ... ... ... ...
CC49        ... ... ... ... ... ... ... ... ... ... ...
CC83        ... ..C ... ... ... ... ... ... ... ... ...
CC92        ... ... ... ... ... ... ... ... ... ... ...
```

FIG. 2G

```
VHαTAG   TGT AAA AGA CACAGTGTTG TAACCACATC CTGAGTGTGT
CC46     ... .CG G.C GGC TAC GGG TTT GCT TTC TGG GGC
CC49     ... .C. ... TCC CTG AAT ATG GCC TAC TGG GGT
CC83     ... .G. ... |TCC TTC TAC GGC AAC ---|TGG GGC
CC92     ... .C. ... |TCT CTA TCC GGG AAC TCC|TGG GGC
                     |<---------CDR3-------->|

VHαTAG   CAGAAATCCT GGGGGAGCAG AAAGATACAC TGGGACTGAG
CC46     CAA GGG ACT CTG GTC ACT GTC TCT GCA G
CC49     CAA GGA ACC TCA GTC ACC GTC TCC TCA G
CC83     CAA GGC ACC ACC CTC ACA GTC TCC TCA G
CC92     CAG GGC ACC ACT CTC ACA GTC TCC TCA G

VHαTAG   AAGACAGAAA AATTAATCCT TAGACTTGCT CAGAAATCGT

VHαTAG   AATTTTGAAT GCCTATTTAT TTCATCTTGC TCACACACCT

VHαTAG   ATATTGCTTT TGTAAGCTT
```

FIG. 3A

```
         ←−19       LEADER PEPTIDE                         −10
         Met Glu Trp Ser Trp Val Phe Leu Phe Phe
VHαTAG    .   .   .   .   .   .   .   .   .   .
CC46      .   .   .   .   .   .   .   .   .   .
CC49      .   .   .   .   .   .   .   .   .   .
CC83      .   .   .   .   .   .   .   .   .   .
CC92      .   .   .   .   .   .   .   .   .   .

Leu Ser Val Thr Thr Gly Val His Ser│Gln
VHαTAG    .   .   .   .   .   .   .   .   .   .
CC46      .   .   .   .   .   .   .   .   .   .
CC49      .   .   .   .   .   .   .   .   .   .
CC83      .   .   .   .   .   .   .   .   .   .
CC92      .   .   .   .   .   .   .   .   .   .

10
         Val Gln Leu Gln Gln Ser Asp Ala Glu Leu
         Phe
VHαTAG    .   .   .   .   .   .   .   .   .   .
          .
CC46      .   .   .   .   .   .   .   .   .   .
CC49      .   .   .   .   .   .   .   .   .   .
CC83      .   .   .   .   .   .   .   .   .   .
CC92      .   .   .   .   .   .   .   .   .   .
```

FIG. 3B

```
                                    20
VHαTAG    Val Lys Pro Gly Ala Ser Val Lys Ile Ser  . . . .
CC46          Arg . . . . . . . . .                . . . .
CC49          . . . . . . . . . .                  . . . .
CC83          . . . . . . . . . .                  . . . .
CC92          . . . . . . . . . .                  . . . .

30
VHαTAG    Cys Lys Ala Ser Gly Tyr Thr Phe Thr Asp  . . . .
CC46          . . . . . . . . . .                  . . . .
CC49          . . . . . . . . . .                  . . . .
CC83          . . . . . . . . . .                  . . . .
CC92          . . . . . . . . . .                  . . . .

──CDR1──→
                                    40
VHαTAG    His Ala Ile His Trp Val Lys Gln Lys Pro  . . . .
CC46          . . . . . . . . . .                  . . . .
CC49          . . . . . Asn . . . .                . . . .
CC83          . . . . . . . . . .                  . . . .
CC92          . . . . . . . . . .                  . . . .

50
VHαTAG    Glu Gln Gly Leu Glu Trp Ile Gly Tyr Ile  . . . .
CC46          . . . . . . . . . Phe                . . . .
CC49          . . . . . . . . . Phe                . . . .
CC83          . . . . . . . . . .                  . . . .
CC92          . . . . . . . . . .                  . . . .
```

FIG. 3C

```
                            CDR2                    60
         Ser Pro Gly Asn Gly Asp Ile Lys Tyr Asn
VHαTAG    .   .   .   .   .   .   .   .   .   .
CC46      .   .   .   .   .  Asp  Phe  .   .   .
CC49      .   .   .   .   .  Asp  .    .   .   .
CC83      .   .   .   .   .  Asp  .    .   .   .
CC92      .   .   .   .   .   .   .    .   .   .

70
         Glu Lys Phe Lys Gly Lys Ala Thr Leu Thr
VHαTAG    .   .   .   .   .   .   .   .   .   .
CC46      .  Arg  .   .   .   .   .   .   .   .
CC49      .   .   .   .   .   .   .   .   .   .
CC83      .   .   .   .   .   .   .   .   .   .
CC92      .   .   .   .   .   .   .   .   .   .

80
         Ala Asp Lys Ser Ser Ser Thr Ala Tyr Met     Val
VHαTAG    .   .   .   .   .   .   .   .   .   .   .   .
CC46      .   .   .   .   .   .   .   .   .   .   .   .
CC49      .   .   .   .   .   .   .   .   .   .   .   .
CC83      .   .   .  Pro  .  Asn  .   .   .   .       Val
CC92      .   .   .   .   .   .   .   .   .   .
```

FIG.3E

```
                                    110
CC46  Gly Thr Leu Val Thr Val Ser Ala
CC49  Gly Thr Ser Val Thr Val Ser Ser
CC83  Gly Thr Thr Leu Thr Val Ser Ser
CC92  Gly Thr Thr Leu Thr Val Ser Ser
```

FIG.4A

```
               Met Glu Lys Leu Trp Phe
 1  5'-GAA TTC ATG GAA AAA CTT TGG TTC

7      Leu Leu Leu Leu Leu Thr Ile Pro
25      TTG CTT CTG CTG CTG ACC ATC CCT

15      Ser Trp Val Leu Ser Gln Ile Thr
49      TCA TGG GTC TTG TCC CAG ATC ACC

23      Leu Lys Glu Ser Gly Pro Thr Leu
73      TTG AAG GAG TCT GGT CCT ACN CTG

31      Val Lys Pro Thr Gln Thr Leu Thr
97      GTG AAA CCC ACA CAG ACC CTC ACG

37      Leu Thr Cys Thr Phe Ser Gly Phe
121     CTG ACC TGC ACC TTC TCT GGG TTC
                          ┌──────CDR1──────
47      Ser Leu Ser │Thr His Gly Val Gly
145     TCA CTC AGC │ACT CAT GGA GTG GGT
     ───────────────→│
55      Val Gly│Trp Ile Arg Xaa Xaa Pro
169     GTG GGC│TGG ATC CGT NNN NNC CCA

63      Gly Lys Ala Leu Glu Trp Leu Ala
193     GGA AAG GCC CTG GAG TGG CTT GCA
     ┌──────────────────CDR2──────────────
71     │Leu Ile Tyr Trp Asp Asp Asp Lys
217    │CTC ATT TAT TGG GAT GAT GAT AAG
                                         ─┐
79      Arg Tyr Ser Pro Ser Leu Lys Ser│
241     CGC TAC AGC CCA TCT CTG AAG AGC│
```

FIG.4B

| | | | | | | | |
|---|---|---|---|---|---|---|---|
| 87 | Arg | Leu | Thr | Ile | Thr | Lys | Asp | Thr |
| 265 | AGG | CTC | ACC | ATC | ACC | AAG | GAC | ACC |
| 95 | Ser | Lys | Asn | Gln | Val | Ile | Leu | Thr |
| 289 | TCC | AAA | AAC | CAG | GTG | ATC | CTT | ACA |
| 103 | Met | Thr | Asn | Met | Asp | Pro | Val | Asp |
| 313 | ATG | ACC | AAC | ATG | GAC | CCT | GTG | GAC |
| 111 | Thr | Ala | Thr | Tyr | Tyr | Cys | Ala | His |
| 337 | ACA | GCC | ACA | TAT | TAT | TGT | GCA | CAC |

|←——————— CDR3 ———————→|

| 119 | Gly | Leu | Pro | Ser | Met | Val | Lys | Asn |
| 361 | GGG | CTG | CCA | TCT | ATG | GTT | AAG | AAC |

| 127 | Trp | Gly | Gln | Gly | Thr | Thr | Val | Thr |
| 385 | TGG | GGC | CAA | GGG | ACC | ACG | GTC | ACC |

| 135 | Val | Ser | Ser | Gly | Ser |
| 409 | GTC | TCC | TCA | GGG | AGT-3' |

FIG.5A

MOUSE GERMLINE J-H GENES
FROM pNP9

```
5'-GGATCCTGGC CAGCATTGCC GCTAGGTCCC
   TCTCTTCTAT GCTTTCTTTG TCCCTCACTG
   GCCTCCATCT GAGATAATCC TGGAGCCCTA
   GCCAAGGATC ATTTATTGTC AGGGGTCTAA
   TCATTGTTGT CACAATGTGC CTGGTTTGCT
   TACTGGGGCC AAGGACTCT GGTCACTGTC
   TCTGCAGGTG AGTCCTAACT TCTCCCATTC
   TAAATGCATG TTGGGGGAT TCTGAGCCTT
   CAGGACCAAG ATTCTCTGCA AACGGGAATC
   AAGATTCAAC CCCTTTGTCC CAAAGTTGAG
   ACATGGGTCT GGGTCAGGGA CTCTCTGCCT
   GCTGGTCTGT GGTGACATTA GAACTGAAGT
   ATGATGAAGG ATCTGCCAGA ACTGAAGCTT
   GAAGTCTGAG GCAGAATCTT GTCCAGGGTC
   TATCGGACTC TTGTGAGAAT TAGGGGCTGA
   CAGTTGATGG TGACAATTTC AGGGTCAGTG
   ACTGTCAGGT TTCTCTGAGG TGAGGCTGGA
   ATATAGGTCA CCTTGAAGAC TAAAGAGGGG
   TCCAGGGGCT TTTCTGCACA GGCAGGGAAC
   AGAATGTGGA ACAATGACTT GAATGGTTGA
   TTCTTGTGTG ACACCAAGAA TTGGCATAAT
   GTCTGAGTTG CCCAAGGGTG ATCTTAGCTA
   AAAACCCACT ATTGTGATTA CTATGCTATG
   GACTACTGGG GTCAAGGAAC CTCAGTCACC
   GTCTCCTCAG GTAAGAATGG CCTCTCCAGG
   TCTTTATTTT TAACCTTTGT TATGGAGTTT
   TCTGAGCATT GCAGACTAAT CTTGGATATT
   TGCCCTGAGG GAGCCGGCTG AGAGAAGTTG
   GGAAATAAAT CTGTCTAGGG ATCTCAGAGC
   CTTTAGGACA GATTATCTCC ACATCTTTGA
   AAAACTAAGA ATCTGTGTGA TGGTGTTGGT
   GGAGTCCCTG GATGATGGGA TAGGGACTTT
```

FIG.5B

```
GGAGGCTCAT TTGAGGGAGA TGCTAAAACA
ATCCTATGGC TGGAGGGATA GTTGGGGCTG
TAGTTGGAGA TTTTCAGTTT TTAGAATGAA
GTATTAGCTG CAATACTTCA AGGACCACCT
CTGTGACAAC CATTTTATAC AGTATCCAGG
CATAGGGACA AAAAGTGGAG TGGGGCACTT
TCTTTAGATT TGTGAGGAAT GTTCCACACT
AGATTGTTTA AAACTTCATT TGTTGGAAGG
AGCTGTCTTA GTGATTGAGT CAAGGGAGAA
AGGCATCTAG CCTCGGTCTC AAAAGGGTAG
TTGCTGTCTA GAGAGGTCTG GTGGAGCCTG
CAAAAGTCCA GCTTTCAAAG GAACACAGAA
GTATGTGTAT GGAATATTAG AAGATGTTGC
TTTTACTCTT AAGTTGGTTC CTAGGAAAAA
TAGTTAAATA CTGTGACTTT AAAATGTGAG
AGGGTTTTCA AGTACTCATT TTTTTAAATG
TCCAAAATTT TTGTCAATCA ATTTGAGGTC
TTGTTTGTGT AGAACTGACA TTACTTAAAG
TTTAACCGAG GAATGGGAGT GAGGCTCTCT
CATACCCTAT TCAGAACTGA CTTTTAACAA
TAATAAATTA AGTTTAAAAT ATTTTTAAAT
GAATTGAGCA ATGTTGAGTT GAGTCAAGAT
GGCCGATCAG AACCGGAACA CCTGCAGCAG
CTGGCAGGAA GCAGGTCATG TGGCAAGGCT
ATTTGGGGAA GGGAAAATAA AACCACTAGG
TAAACTTGTA GCTGTGGTTT GAAGAAGTGG
TTTTGAAACA CTCTGTCCAG CCCCACCAAA
CCGAAAGTCC AGGCTGAGCA AAACACCACC
TGGGTAATTT GCATTTCTAA AATAAGTTGA
GGATTCAGCC GAAACTGGAG AGGTCCTCTT
TTAACTTATT GAGTTCAACC TTTTAATTTT
AGCTTGAGTA GTTCTAGTTT CCCCAAACTT
AAGTTTATCG ACTTCTAAAA TGTATTTAGA
ATTC-3'
```

FIG.8A

HUMVL (+), 26-MER:
(Cla I)
5'- GAAGAGTATC GATAAAATTT ATTGAG-3'

FIG.8B

HUMVL(-), 98-MER:

(SPLICE SITE)
(Hind III)
5'-CATTAAGCTT AGAAAAGTGT ACTTACGTTT
GATCACCACC TTGGTCCCTC CGCCGAAAGT
GAGAGGATAA CTATAATATT GCTGACAGTA
ATAAACTG-3'

Leu Thr Phe Gly Gly Gly Thr Lys
CTC ACT TTC GGC GGA GGG ACC AAG

Val Glu Ile Lys A(rg)
GTG GAG ATC AAA C GTAAGTGCAC

TTTCCTAA

FIG.10A

```
     Cla I
5' ATCGATAAAA TTTATTGAGA ATTTGTTTAT TATGATTAAC  3418
3' TAGCTATTTT AAATAACTCT TAAACAAATA ATACTAATTG

AGAGGTAAAA GCCAGTATAT TACTGATTAA TATAGGTAAA  3458
   TCTCCATTTT CGGTCATATA ATGACTAATT ATATCCATTT
            *
   AGGCAGTTAA GAAATTGGGA ATGCTTTCTC TTCTGCTTTC  3498
   TCCGTCAATT CTTTAACCCT TACGAAAGAG AAGACGAAAG

TTCTACGATG CACAAGGCGT TTCACATTTA TGCCCCTATG  3538
   AAGATGCTAC GTGTTCCGCA AAGTGTAAAT ACGGGGATAC

AAAATTACTA GGCTGTCCTA GTCATTAGAT CTTTCAGCAG  3578
   TTTTAATGAT CCGACAGGAT CAGTAATCTA GAAAGTCGTC

TTTGTAGTTT TAGAGCTTCT AAGTTGACTT CTGTCTTTTC  3618
   AAACATCAAA ATCTCGAAGA TTCAACTGAA GACAGAAAAG

TATTCATACA ATTACACATT CTGTGATGAT ATTTTTGGCT  3658
   ATAAGTATGT TAATGTGTAA GACACTACTA TAAAAACCGA
                        ─────────────
                           HUMLIN1(-)
```

FIG. 10B

```
CTTGATTTAC ATTGGGTACT TTCACAACCC ACTGCTCATG  3698
GAACTAAATG TAACCCATGA AAGTGTTGGG TGACGAGTAC

AAATTTGCTT TTGTACTACT GGTTGTTTTT GCATAGGCCC  3738
TTTAAACGAA AACATGATGA CCAACAAAAA CGTATCCGGG

CTCCAGGCCA CGACCAGGTG TTTGGATTTT ATAAACGGGC  3778
GAGGTCCGGT GCTGGTCCAC AAACCTAAAA TATTTGCCCG

CGTTTGCATT GTGAACTGAG CTACAACAGG CAGGCAGGGG  3818
GCAAACGTAA CACTTGACTC GATGTTGTCC GTCCGTCCCC

Met Val Leu Gln Thr Gln Val Phe Ile  -10
CAGCAAG ATG GTG CTG CAG ACC CAG GTC TTC ATT     3852
GTCGTTC TAC CAC GAC GTC TGG GTC CAG AAG TAA

Ser Leu Leu Trp Ile Ser G Intron
TCT CTG TTG CTC TGG ATC TCT G GTGA GGAATTAAAA   -4
AGA GAC AAC GAG ACC TAG AGA C CACT CCTTAATTTT   3888

AGTGCCACAG TCTTTTCAGA GTAATATCTG TGTAGAAATA
TCACGGTGTC AGAAAGTCT CATTATAGAC ACATCTTTAT

HUMLIN2(-)
```

FIG.10C

```
                                                                      7
                                                                   4125
AAAAAATTA  AGATATAGTT  GGAAATAATG  ACTATTCCA
TTTTTTAAT  TCTATATCAA  CCTTTATTAC  TGATAAAGGT
     BamHI
ATATGGATCC  AATTATCTGC  TGACTTATAA  TACTACTAGA
TATACCTAGG  TTAATAGACG  ACTGAATATT  ATGATGATCT

AAGCAAATTT  AAATGACATA  TTTCAATTAT  ATCTGAGACA
TTCGTTTAAA  TTTACTGTAT  AAAGTTAATA  TAGACTCTGT

GCGTGTATAA  GTTTATGTAT  AATCATTGTC  CATTACTGAC
CGCACATATT  CAAATACATA  TTAGTAACAG  GTAATGACTG

TACAG
ATGTC
                                   +1
ly  Ala  Tyr  Gly  Asp  Ile  Val  Met  Thr  Gln  Ser
GT  GCC  TAC  GGG  GAC  ATC  GTG  ATG  ACC  CAG  TCT
CA  CGG  ATG  CCC  CTG  TAG  CAC  TAC  TGG  GTC  AGA
```

FIG. 10D

```
Pro Asp Ser Leu Ala Val Ser Leu Gly Glu Arg Ala Thr 20
CCA GAC TCC CTG GCT GTG TCT CTG GGC GAG AGG GCC ACC4164
GGT CTG AGG GAC CGA CAC AGA GAC CCG CTC TCC CGG TGG
                                          ┌─── CDR1
Ile Asn Cys│Lys Ser Ser Gln Ser Val Leu Tyr Ser Ser 27F
ATC AAC TGC AAG TCC AGC CAG AGT GTT TTA TAC AGC TCC4203
TAG TTG ACG TTC AGG TCG GTC TCA CAA AAT ATG TCG AGG

Asn Asn Lys Asn Tyr Leu Ala│Trp Tyr Gln Gln Lys Pro 40
AAC AAT AAG AAC TAC TTA GCT TGG TAC CAG CAG AAA CCA4242
TTG TTA TTC TTG ATG AAT CGA ACC ATG GTC GTC TTT GGT
     HUM1CDR1(-)                                 ┌── CDR2 ──
Gly Gln Pro Pro Lys Leu Leu Ile Tyr│Trp Ala Ser Thr 53
GGA CAG CCT CCT AAG CTG CTC ATT TAC TGG GCA TCT ACC4281
CCT GTC GGA GGA TTC GAC GAG TAA ATG ACC CGT AGA TGG
     ┌──
Arg Glu Ser│Gly Val Pro Asp Arg Phe Ser Gly Ser Gly 66
CGG GAA TCC GGG GTC CCT GAC CGA TTC AGT GGC AGT GGG4320
GCC CTT AGG CCC CAG GGA CTG GCT AAG TCA CCG TCA CCC

Ser Gly Thr Asp Phe Thr│Leu Thr Ile Ser Ser Leu Gln Ala
TCT GGG ACA GAT TTC ACT CTC ACC ATC AGC AGC CTG CAG GCT
AGA CCC TGT CTA AAG TGA GAG TGG TAG TCG TCG GAC GTC CGA
```

FIG. 10E

```
                                                   ┌─── CDR3 ─────────────
Glu Asp Val Ala Val Tyr Tyr Cys  Gln Gln Tyr Tyr Ser 93
GAA GAT GTG GCA GTT TAT TAC TGT  CAG CAA TAT TAT AGT 4400
CTT CTA CAC CGT CAA ATA ATG ACA  GTC GTT ATA ATA TCA
                              ↑
     ┌───────────────────────┘
Tyr Pro Leu Thr  Phe Gly Gly Gly Thr Lys Val Val Ile 106
TAT CCT CTC ACT  TTC GGC GGA GGG ACC AAG GTG GTG ATC 4439
ATA GGA GAG TGA  AAG CCG CCT CCC TGG TTC CAC CAC TAG

Hind III                    107
Lys A(rg)                                     4466
AAA C GTAAGTACAC TTTTCTAAG CTT-3'
TTT G CATTCATGTG AAAAGATTC GAA 5'
```

FIG.15

(A portion of the DNA
Sequence of pSV2neo)

←——TOWARDS Eco RI SITE 5'-GAG<u>GAGGTTA</u>

<u>GGGTTTATGA</u> <u>GGAC</u>ACAGAG GAGCTTCCTG

G|GGATCC|AGA CATGATAAGA TACATTGATG
  Bam H1

AGTTTGGACA AACCACAACT AGA-3'

FIG. 17

```
LOST Bam HI
SITE IN
pSV2neo
                    Cla I       Eco RV  Spe I
5'-CTTCCTGGGG  ATCATCGATT  GATATCAACT   3394
                         |    FROM HUMAN C
                         | Hind III-Bam HI INSERT
           Hind III
      AGTTGAAGCT  TTTTTTTTTT  CAGTGCTATT  3423

TAATTATTTC  AATATCCTCT  CATCAAATGT  3453

ATTTAAATAA  CAAAAGCTCA  ACCAAAAAGA  3483

AAGAAATATG  TAATTCTTTC  AGAGTAAAAA  3513

TCACACCCAT  GACCTGGCCA  CTGAGGGCTT  3543

GATCAATTCA  CTTTGAATTT  GGCATTAAAT  3573

ACCATTAAGG  TATATTAACT  GATTTTAAAA  3603
                                 TOWARDS
      TAAGATATAT  TCGTGACC-3'   Bam HI   3621
```

DNA SEQUENCING — pRL1001

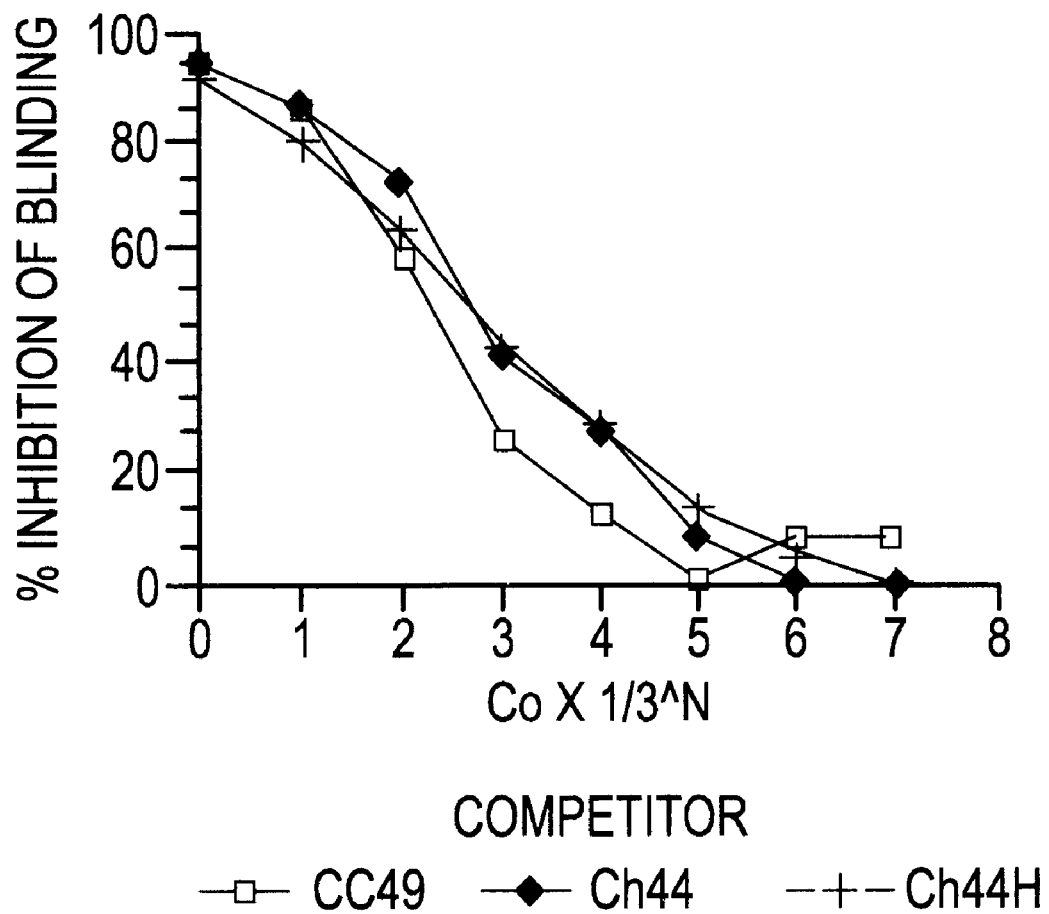

FIG. 22A

```
                                            Met Leu
AAAAACTAT AAGCTCCATG ATG CTT

Leu Gln Ala Phe Leu Phe Leu Leu Ala
TTG CAA GCT TTC CTT TTC CTT TTG GCT

Gly Phe Ala Ala Lys Ile Ser Ala Asp
GGT TTT GCA GCC AAA ATA TCT GCA GAC

Ile Val Met Thr Gln Ser Pro Asp Ser
ATC GTG ATG ACC CAG TCT CCA GAC TCC

Leu Ala Val Ser Leu Gly Glu Arg Ala
CTG GCT GTG TCT CTG GGC GAG AGG GCC
                                  ←———————— CDR1L ——
Thr Ile Asn Cys Lys Ser Ser Gln Ser
ACC ATC AAC TGC AAG TCC AGC TGC AAG

Val Leu Tyr Ser Ser Asn Asn Lys Asn
GTT TTA TAC AGC TCC AAC AAT AAG AAC
————————————→
Tyr Leu Ala Trp Tyr Gln Gln Lys Pro
TAC TTA GCT TGG TAC CAG CAG AAA CCA

Gly Gln Pro Pro Lys Leu Leu Ile Tyr
GGA CAG CCT CCT AAG CTG CTC ATT TAC
           ——— CDR2L ————————→
Trp Ala Ser Thr Arg Glu Ser Gly Val
TGG GCA TCT ACC CGG GAA TCC GGG GTC

Pro Asp Arg Phe Ser Gly Ser Gly Ser
CCT GAC CGA TTC AGT GGC AGC GGG TCT
```

FIG. 22B

```
Gly Thr Asp Phe Thr Leu Thr Ile Ser
GGG ACA GAT TTC ACT CTC ACC ATC AGC

Ser Leu Gln Ala Glu Asp Val Ala Val
AGC CTG CAG GCT GAA GAT GTG GCA GTT
                         |─────────CDR3L──────
Tyr Tyr Cys|Gln Gln Tyr Tyr Ser Tyr
TAT TAC TGT|CAG CAA TAT TAT AGT TAT

─────────────────────|
Pro Leu Thr|Phe Gly Gly Gly Thr Lys
CCT CTC ACT|TTC GGC GGA GGG ACC AAG

|
Val|Lys Glu Ser Gly Ser Val Ser Ser
GTG|AAG GAG TCA GGT TCG GTC TCC TCA
    ──── LINKER ───────────────────
Glu Gln Leu Ala Gln Phe Arg Ser Leu
GAA CAA TTG GCC CAA TTT CGT TCC TTA

──────|
Asp|Val Gln Leu Gln Gln Ser Asp Ala
GAC|GTC CAG TTG CAG CAG TCT GAC GCT

Glu Leu Val Lys Pro Gly Ala Ser Val
GAG TTG GTG AAA CCT GGG GCT TCA GTG

Lys Ile Ser Cys Lys Ala Ser Gly Tyr
AAG ATT TCC TGC AAG GCT TCT GGC TAC
                     |──────CDR1H──────|
Thr Phe Thr|Asp His Ala Ile His|Trp
ACC TTC ACT|GAC CAT GCA ATT CAC|TGG

Val Lys Gln Asn Pro Glu Gln Gly Leu
GTG AAA CAG AAC CCT GAA CAG GGC CTG
```

FIG. 22C

| Glu | Trp | Ile | Gly | Tyr | Phe | Ser | Pro | Gly |
|-----|-----|-----|-----|-----|-----|-----|-----|-----|
| GAA | TGG | ATT | GGA | TAT | TTT | TCT | CCC | GGA |

———————————————— CDR2H ————————

| Asn | Asp | Asp | Phe | Lys | Tyr | Asn | Glu | Arg |
|-----|-----|-----|-----|-----|-----|-----|-----|-----|
| AAT | GAT | GAT | TTT | AAA | TAC | AAT | GAG | AGG |

| Phe | Lys | Gly | Lys | Ala | Thr | Leu | Thr | Ala |
|-----|-----|-----|-----|-----|-----|-----|-----|-----|
| TTC | AAG | GGC | AAG | GCC | ACA | CTG | ACT | GCA |

| Asp | Lys | Ser | Ser | Ser | Thr | Ala | Tyr | Val |
|-----|-----|-----|-----|-----|-----|-----|-----|-----|
| GAC | AAA | TCC | TCC | AGC | ACT | GCC | TAC | GTG |

| Gln | Leu | Asn | Ser | Leu | Thr | Ser | Glu | Asp |
|-----|-----|-----|-----|-----|-----|-----|-----|-----|
| CAG | CTC | AAC | AGC | CTG | ACA | TCT | GAG | GAT |

| Ser | Ala | Val | Tyr | Phe | Cys | Thr | Arg | Ser |
|-----|-----|-----|-----|-----|-----|-----|-----|-----|
| TCT | GCA | GTG | TAT | TTC | TGT | ACA | AGA | TCC |

———— CDR3H ————————

| Leu | Asn | Met | Ala | Tyr | Trp | Gly | Gln | Gly |
|-----|-----|-----|-----|-----|-----|-----|-----|-----|
| CTG | AAT | ATG | GCC | TAC | TGG | GGT | CAA | GGA |

| Thr | Ser | Val | Thr | Val | Ser |     |     |     |
|-----|-----|-----|-----|-----|-----|-----|-----|-----|
| ACC | TCA | GTC | ACC | GTC | TCC | TAG | TGA |     |

AGCTTGGAAC ACCACACAAA CCATATCCAA A

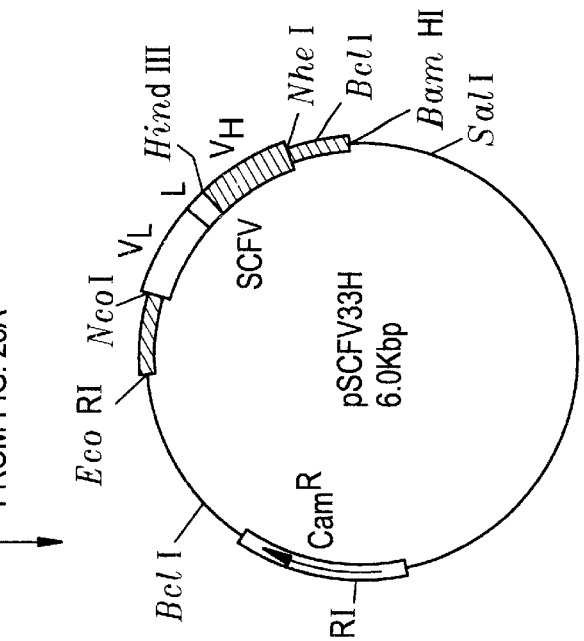
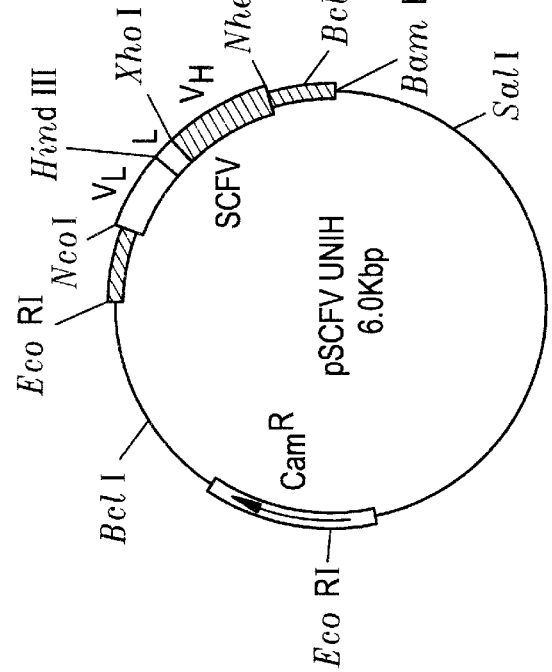
FIG. 25B

FIG.26A

```
                                         Eco RI
CTCATGTTTG  ACAGCTTATC  ATCGATGAAT

TCCATCACTT  CCCTCCGTTC  ATTTGTCCCC

GGTGGAAACG  AGGTCATCAT  TTCCTTCCGA

AAAAACGGTT  GCATTTAAAT  CTTACATATG

TAATACTTTC  AAAGACTACA  TTTGTAAGAT

TTGATGTTTG  AGTCGGCTGA  AAGATCGTAC

GTACCAATTA  TTGTTTCGTG  ATTGTTCAAG

CCATAACACT  GTAGGGATAG  TGGAAAGAGT

GCTTCATCTG  GTTACGATCA  ATCAAATATT
```

|  |  |  | pelB Signal |  |  |
|---|---|---|---|---|---|

```
                                         Met  Lys  Tyr  Leu
CAAACGGAGG  GAGACGATTT  TG  ATG  AAA  TAC  CTA
Sequence
Leu  Pro  Thr  Ala  Ala  Ala  Gly  Leu  Leu  Leu
TTG  CCT  ACG  GCA  GCC  GCT  GGA  TTG  TTA  TTA
                              Nco I →  ← H4V_L
Leu  Ala  Ala  Gln  Pro  Ala  Met  Ala  Asp  Ile
CTC  GCT  GCC  CAA  CCA  GCC  ATG  GCC  GAC  ATC Val  Met  Thr  Gln  Ser  Pro  Asp  Ser  Leu  Ala
GTG  ATG  ACC  CAG  TCT  CCA  GAC  TCC  CTG  GCT Val  Ser  Leu  Gly  Glu  Arg  Ala  Thr  Ile  Asn
GTG  TCT  CTG  GGC  GAG  AGG  GCC  ACC  ATC  AAC Cys  Lys  Ser  Ser  Gln  Ser  Val  Leu  Tyr  Ser
TGC  AAG  TCC  AGC  CAG  AGT  GTT  TTA  TAC  AGC
```

FIG. 26B

| | | | | | | | | | |
|---|---|---|---|---|---|---|---|---|---|
| Ser | Asn | Asn | Lys | Asn | Tyr | Leu | Ala | Trp | Tyr |
| TCC | AAC | AAT | AAG | AAC | TAC | TTA | GCT | TGG | TAC |

| | | | | | | | | | |
|---|---|---|---|---|---|---|---|---|---|
| Gln | Gln | Lys | Pro | Gly | Gln | Pro | Pro | Lys | Leu |
| CAG | CAG | AAA | CCA | GGA | CAG | CCT | CCT | AAG | CTG |

| | | | | | | | | | |
|---|---|---|---|---|---|---|---|---|---|
| Leu | Ile | Tyr | Trp | Ala | Ser | Thr | Arg | Glu | Ser |
| CTC | ATT | TAC | TGG | GCA | TCT | ACC | CGG | GAA | TCC |

| | | | | | | | | | |
|---|---|---|---|---|---|---|---|---|---|
| Gly | Val | Pro | Asp | Arg | Phe | Ser | Gly | Ser | Gly |
| GGG | GTC | CCT | GAC | CGA | TTC | AGT | GGC | AGC | GGG |

| | | | | | | | | | |
|---|---|---|---|---|---|---|---|---|---|
| Ser | Gly | Thr | Asp | Phe | Thr | Leu | Thr | Ile | Ser |
| TCT | GGG | ACA | GAT | TTC | ACT | CTC | ACC | ATC | AGC |

| | | | | | | | | | |
|---|---|---|---|---|---|---|---|---|---|
| Ser | Leu | Gln | Ala | Glu | Asp | Val | Ala | Val | Tyr |
| AGC | CTG | CAG | GCT | GAA | GAT | GTG | GCA | GTT | TAT |

| | | | | | | | | | |
|---|---|---|---|---|---|---|---|---|---|
| Tyr | Cys | Gln | Gln | Tyr | Tyr | Ser | Tyr | Pro | Leu |
| TAC | TGT | CAG | CAA | TAT | TAT | AGT | TAT | CCT | CTC |

H4$V_L$

| | | | | | | | | | |
|---|---|---|---|---|---|---|---|---|---|
| Thr | Phe | Gly | Gly | Gly | Thr | Lys | Val | Val | Ile |
| ACT | TTC | GGC | GGA | GGG | ACC | AAG | GTG | GTG | ATC |

*Hind* III LINKER

| | | | | | | | | | |
|---|---|---|---|---|---|---|---|---|---|
| Lys | Leu | Ser | Ala | Asp | Asp | Ala | Lys | Lys | Asp |
| AAG | CTT | AGT | GCG | GAC | GAT | GCG | AAA | AAG | GAT |

| | | | | | | | | | |
|---|---|---|---|---|---|---|---|---|---|
| Ala | Ala | Lys | Lys | Asp | Asp | Ala | Lys | Lys | Asp |
| GCT | GCG | AAG | AAG | GAT | GAC | GCT | AAG | AAA | GAC |

LINKER    *Xho* I    CC49 $V_H$

| | | | | | | | | | |
|---|---|---|---|---|---|---|---|---|---|
| Asp | Ala | Lys | Lys | Asp | Leu | Gln | Val | Gln | Leu |
| GAT | GCT | AAA | AAG | GAC | CTC | CAG | GTT | CAG | TTG |

FIG. 26C

| | | | | | | | | | |
|---|---|---|---|---|---|---|---|---|---|
| Gln | Gln | Ser | Ala | Glu | Leu | Val | Lys | Pro | Gly |
| CAG | CAG | TCT | GCT | GAG | TTG | GTG | AAA | CCT | GGG |
| Ala | Ser | Val | Lys | Ile | Ser | Cys | Lys | Ala | Ser |
| GCT | TCA | GTG | AAG | ATT | TCC | TGC | AAG | GCT | TCT |
| Gly | Tyr | Thr | Phe | Thr | Asp | His | Ala | Ile | His |
| GGC | TAC | ACC | TTC | ACT | GAC | CAT | GCA | ATT | CAC |
| Trp | Val | Lys | Gln | Asn | Pro | Glu | Gln | Gly | Leu |
| TGG | GTG | AAA | CAG | AAC | CCT | GAA | CAG | GGC | CTG |
| Glu | Trp | Ile | Gly | Tyr | Phe | Ser | Pro | Gly | Asn |
| GAA | TGG | ATT | GGA | TAT | TTT | TCT | CCC | GGA | AAT |
| Asp | Asp | Phe | Lys | Tyr | Asn | Glu | Arg | Phe | Lys |
| GAT | GAT | TTT | AAA | TAC | AAT | GAG | AGG | TTC | AAG |
| Gly | Lys | Ala | Thr | Leu | Thr | Ala | Asp | Lys | Ser |
| GGC | AAG | GCC | ACA | CTG | ACT | GCA | GAC | AAA | TCC |
| Ser | Ser | Thr | Ala | Tyr | Val | Gln | Leu | Asn | Ser |
| TCC | AGC | ACT | GCC | TAC | GTG | CAG | CTC | AAC | AGC |
| Leu | Thr | Ser | Glu | Asp | Ser | Ala | Val | Tyr | Phe |
| CTG | ACA | TCT | GAG | GAT | TCT | GCA | GTG | TAT | TTC |
| Cys | Thr | Arg | Ser | Leu | Asn | Met | Ala | Tyr | Trp |
| TGT | ACA | AGA | TCC | CTG | AAT | ATG | GCC | TAC | TGG |
| Gly | Gln | Gly | Thr | Ser | Val | Thr | Val | Ser | Ser |
| GGT | CAA | GGA | ACC | TCA | GTC | ACC | GTC | TCC | TCA |

```
       Nhe I
TAA AAAGCTAGCG ATGAATCCGT CAAAACATCA
                            Bcl I
TCTTACATAA AGTCACTTGG TGATCAAGCT

CATATCATTG TCCGGCAATG GTGTGGGCTT

TTTTTGTTTT CTATCTTTAA AGATCATGTG

AAGGAAAAAA CGGGAAAATC GGTCTGCGGG

AAAGGACCGG GTTTTTGTCG AAATCATAGG
                                  Bam HI
CGAATGGGTT GGATTGTGAC AAAATTCGGA TCC
```

FIG. 28A

```
                                                Eco RI
CTCATGTTTG  ACAGCTTATC  ATCGATGAAT

TCCATCACTT  CCCTCCGTTC  ATTTGTCCCC

GGTGGAAACG  AGGTCATCAT  TTCCTTCCGA

AAAAACGGTT  GCATTTAAAT  CTTACATATG

TAATACTTTC  AAAGACTACA  TTTGTAAGAT

TTGATGTTTG  AGTCGGCTGA  AAGATCGTAC

GTACCAATTA  TTGTTTCGTG  ATTGTTCAAG

CCATAACACT  GTAGGGATAG  TGGAAAGAGT

GCTTCATCTG  GTTACGATCA  ATCAAATATT
```

```
                                      ┌── pelB Signal
                                      │ Met  Lys  Tyr  Leu
CAAACGGAGG  GAGACGATTT  TG│ATG  AAA  TAC  CTA
```
Sequence
```
Leu  Pro  Thr  Ala  Ala  Ala  Gly  Leu  Leu  Leu
TTG  CCT  ACG  GCA  GCC  GCT  GGA  TTG  TTA  TTA
                              Nco I ──►│◄── H4V_L
Leu  Ala  Ala  Gln  Pro  Ala   Met  Ala│Asp  Ile
CTC  GCT  GCC  CAA  CCA  GCC   ATG  GCC│GAC  ATC Val  Met  Thr  Gln  Ser  Pro  Asp  Ser  Leu  Ala
GTG  ATG  ACC  CAG  TCT  CCA  GAC  TCC  CTG  GCT Val  Ser  Leu  Gly  Glu  Arg  Ala  Thr  Ile  Asn
GTG  TCT  CTG  GGC  GAG  AGG  GCC  ACC  ATC  AAC Cys  Lys  Ser  Ser  Gln  Ser  Val  Leu  Tyr  Ser
TGC  AAG  TCC  AGC  CAG  AGT  GTT  TTA  TAC  AGC
```

FIG. 28B

```
Ser Asn Asn Lys Asn Tyr Leu Ala Trp Tyr
TCC AAC AAT AAG AAC TAC TTA GCT TGG TAC

Gln Gln Lys Pro Gly Gln Pro Pro Lys Leu
CAG CAG AAA CCA GGA CAG CCT CCT AAG CTG

Leu Ile Tyr Trp Ala Ser Thr Arg Glu Ser
CTC ATT TAC TGG GCA TCT ACC CGG GAA TCC

Gly Val Pro Asp Arg Phe Ser Gly Ser Gly
GGG GTC CCT GAC CGA TTC AGT GGC AGC GGG

Ser Gly Thr Asp Phe Thr Leu Thr Ile Ser
TCT GGG ACA GAT TTC ACT CTC ACC ATC AGC

Ser Leu Gln Ala Glu Asp Val Ala Val Tyr
AGC CTG CAG GCT GAA GAT GTG GCA GTT TAT

Tyr Cys Gln Gln Tyr Tyr Ser Tyr Pro Leu
TAC TGT CAG CAA TAT TAT AGT TAT CCT CTC
                                                    H4V_L
Thr Phe Gly Gly Gly Thr Lys Val Val Ile
ACT TTC GGC GGA GGG ACC AAG GTG GTG ATC
Hind III LINKER
Lys│Leu Ser Ala Asp Asp Ala Lys Lys Asp
AAG│CTT AGT GCG GAC GAT GCG AAA AAG GAT Ala Ala Lys Lys Asp Asp Ala Lys Lys Asp
GCT GCG AAG AAG GAT GAC GCT AAG AAA GAC
              LINKER   Xho I
Asp Ala Lys Lys Asp Leu│Gln
GAT GCT AAA AAG GAC CTC│CAG
```

FIG. 28C

```
              Nhe I    ┌─ Flag Peptide
           Ala   Ser  │ Asp Tyr Lys Asp
ACAATGTC   GCT   AGC  │GAC TAC AAG GAC
                 ──────→│
Asp Asp Asp Lys│
GAT GAT GAC AAA│TAA   AAACCTAGC GATGAATCCG   TCAAAACATC   ATCTTACATA
              Bcl I
AAGTCACTT    GGTGATCAAG   CTCATATCAT

TGTCCGGCA    ATGGTGTGGG   CTTTTTTTGT

TTTCATCTT    TAAAGATCAT   GTGAAGGAAA

AAACGGGAA    AATCGGTCTG   CGGGAAGGA

CCGGGTTTT    TGTCGAAATC   ATAGGCGAAT
                                    Bam HI
GGGTTGGAT    TGTGACAAAA   TTCGGATCC
```

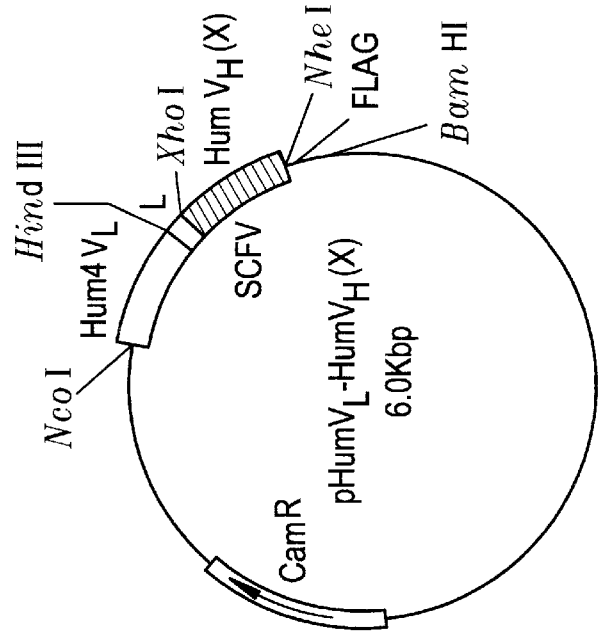
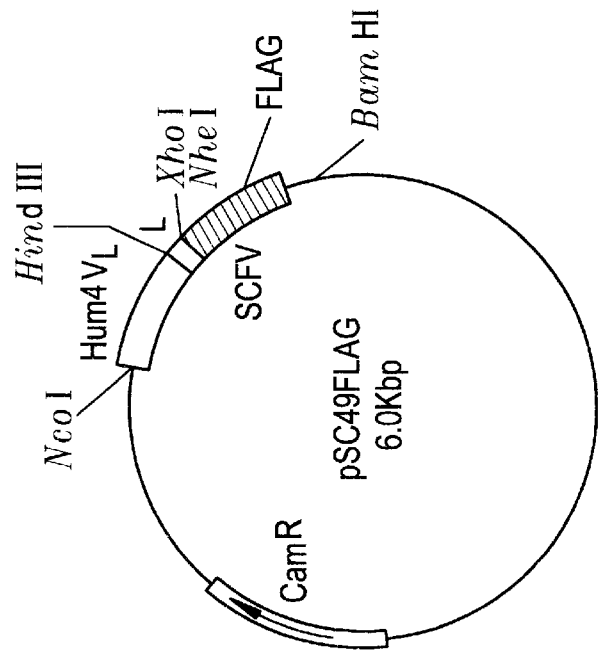
FIG. 29B

FIG. 30A

```
                                               Eco RI
CTCATGTTTG  ACAGCTTATC  ATCGATGAAT

TCCATCACTT  CCCTCCGTTC  ATTTGTCCCC

GGTGGAAACG  AGGTCATCAT  TTCCTTCCGA

AAAAACGGTT  GCATTTAAAT  CTTACATATG

TAATACTTTC  AAAGACTACA  TTTGTAAGAT

TTGATGTTTG  AGTCGGCTGA  AAGATCGTAC

GTACCAATTA  TTGTTTCGTG  ATTGTTCAAG

CCATAACACT  GTAGGGATAG  TGGAAAGAGT

GCTTCATCTG  GTTACGATCA  ATCAAATATT
```

```
                                         |←—————
                                         |   pelB Signal
                                         | Met Lys Tyr Leu
CAAACGGAGG  GAGACGATTT  TG| ATG AAA TAC CTA
```

Sequence

```
Leu Pro Thr Ala Ala Ala Gly Leu Leu Leu
TTG CCT ACG GCA GCC GCT GGA TTG TTA TTA
                        Nco I —→|←—— H4V_L
Leu Ala Ala Gln Pro Ala   Met Ala| Asp Ile
CTC GCT GCC CAA CCA GCC   ATG GCC| GAC ATC

Val Met Thr Gln Ser Pro Asp Ser Leu Ala
GTG ATG ACC CAG TCT CCA GAC TCC CTG GCT

Val Ser Leu Gly Glu Arg Ala Thr Ile Asn
GTG TCT CTG GGC GAG AGG GCC ACC ATC AAC

Cys Lys Ser Ser Gln Ser Val Leu Tyr Ser
TGC AAG TCC AGC CAG AGT GTT TTA TAC AGC
```

FIG. 30B

```
Ser Asn Asn Lys Asn Tyr Leu Ala Trp Tyr
TCC AAC AAT AAG AAC TAC TTA GCT TGG TAC

Gln Gln Lys Pro Gly Gln Pro Pro Lys Leu
CAG CAG AAA CCA GGA CAG CCT CCT AAG CTG

Leu Ile Tyr Trp Ala Ser Thr Arg Glu Ser
CTC ATT TAC TGG GCA TCT ACC CGG GAA TCC

Gly Val Pro Asp Arg Phe Ser Gly Ser Gly
GGG GTC CCT GAC CGA TTC AGT GGC AGC GGG

Ser Gly Thr Asp Phe Thr Leu Thr Ile Ser
TCT GGG ACA GAT TTC ACT CTC ACC ATC AGC

Ser Leu Gln Ala Glu Asp Val Ala Val Tyr
AGC CTG CAG GCT GAA GAT GTG GCA GTT TAT

Tyr Cys Gln Gln Tyr Tyr Ser Tyr Pro Leu
TAC TGT CAG CAA TAT TAT AGT TAT CCT CTC
                                       H4V_L
Thr Phe Gly Gly Gly Thr Lys Val Val Ile
ACT TTC GGC GGA GGG ACC AAG GTG GTG ATC
Hind III LINKER
Lys|Leu  Ser Ala Asp Asp Ala Lys Lys Asp
AAG|CTT  AGT GCG GAC GAT GCG AAA AAG GAT Ala Ala Lys Lys Asp Asp Ala Lys Lys Asp
GCT GCG AAG AAG GAT GAC GCT AAG AAA GAC
             LINKER     Xho I   CC49 V_H
Asp Ala Lys Lys Asp Leu|Gln Val Gln Leu
GAT GCT AAA AAG GAC CTC|CAG GTT CAG TTG
```

FIG. 30C

| | | | | | | | | |
|---|---|---|---|---|---|---|---|---|
| Gln | Gln | Ser | Ala | Glu | Leu | Val | Lys | Pro | Gly |
| CAG | CAG | TCT | GCT | GAG | TTG | GTG | AAA | CCT | GGG |

| Ala | Ser | Val | Lys | Ile | Ser | Cys | Lys | Ala | Ser |
|---|---|---|---|---|---|---|---|---|---|
| GCT | TCA | GTG | AAG | ATT | TCC | TGC | AAG | GCT | TCT |

| Gly | Tyr | Thr | Phe | Thr | Asp | His | Ala | Ile | His |
|---|---|---|---|---|---|---|---|---|---|
| GGC | TAC | ACC | TTC | ACT | GAC | CAT | GCA | ATT | CAC |

| Trp | Val | Lys | Gln | Asn | Pro | Glu | Gln | Gly | Leu |
|---|---|---|---|---|---|---|---|---|---|
| TGG | GTG | AAA | CAG | AAC | CCT | GAA | CAG | GGC | CTG |

| Glu | Trp | Ile | Gly | Tyr | Phe | Ser | Pro | Gly | Asn |
|---|---|---|---|---|---|---|---|---|---|
| GAA | TGG | ATT | GGA | TAT | TTT | TCT | CCC | GGA | AAT |

| Asp | Asp | Phe | Lys | Tyr | Asn | Glu | Arg | Phe | Lys |
|---|---|---|---|---|---|---|---|---|---|
| GAT | GAT | TTT | AAA | TAC | AAT | GAG | AGG | TTC | AAG |

| Gly | Lys | Ala | Thr | Leu | Thr | Ala | Asp | Lys | Ser |
|---|---|---|---|---|---|---|---|---|---|
| GGC | AAG | GCC | ACA | CTG | ACT | GCA | GAC | AAA | TCC |

| Ser | Ser | Thr | Ala | Tyr | Val | Gln | Leu | Asn | Ser |
|---|---|---|---|---|---|---|---|---|---|
| TCC | AGC | ACT | GCC | TAC | GTG | CAG | CTC | AAC | AGC |

| Leu | Thr | Ser | Glu | Asp | Ser | Ala | Val | Tyr | Phe |
|---|---|---|---|---|---|---|---|---|---|
| CTG | ACA | TCT | GAG | GAT | TCT | GCA | GTG | TAT | TTC |

| Cys | Thr | Arg | Ser | Leu | Asn | Met | Ala | Tyr | Trp |
|---|---|---|---|---|---|---|---|---|---|
| TGT | ACA | AGA | TCC | CTG | AAT | ATG | GCC | TAC | TGG |

CC49 V$_H$ ────▶

| Gly | Gln | Gly | Thr | Ser | Val | Thr | Val | Ser | Ser |
|---|---|---|---|---|---|---|---|---|---|
| GGT | CAA | GGA | ACC | TCA | GTC | ACC | GTC | TCC | TCA |

FIG.30D

```
         Nhe I    | Flag Peptide
      Ala   Ser  | Asp  Tyr  Lys  Asp
      GCT   AGC  | GAC  TAC  AAG  GAC Asp  Asp  Asp  Lys|
GAT  GAT  GAC  AAA| TAA    AAACCTAGC GATGAATCCG   TCAAAACATC   ATCTTACATA
                 Bcl I
AAGTCACTT    GGTGATCAAG   CTCATATCAT

TGTCCGGCA    ATGGTGTGGG   CTTTTTTTGT

TTTCATCTT    TAAAGATCAT   GTGAAGGAAA

AAACGGGAA    AATCGGTCTG   CGGGAAGGA

CCGGGTTTT    TGTCGAAATC   ATAGGCGAAT
                                  Bam HI
GGGTTGGAT    TGTGACAAAA   TTCGGATCC
```

FIG. 31B

FROM FIG. 31A

Plate transformation mix onto hydrophilic membranes (137 mm) which are placed on LB CAM 20 agar plates (150 mm) with a colony density of ≤ 50,000 per plate. Grow for 8-16 hours at 37°C.

SCFV is secreted by *E. coli* and may bind to TAG.

Transfer hydrophilic membrane onto fresh LB CAM 20 plate having a TAG-72-coated hydrophobic membrane (137 mm) already placed on the agar surface. Incubate for 24-96 hours.

assay

Process hydrophobic membrane using a prototype biotinylated TAG-competing antibody, e.g. B72.3, CC49, CC83 or biotinylated competing peptide or mimetic. Use streptavidin conjugated with alkaline phosphatase to bind to biotin and suitable substrate for alkaline phosphatase to develop a color reaction.

Co-relate clear zones on membrane assay with colony (ies) on hydrophilic membrane. Isolate/purify correct clone as necessary. Characterize DNA (sequence) and determine binding affinity of SCFV to TAG-72. Purify SCFV and perform *in vivo* animal biodistribution studies.

Determine normal : tumor tissue binding profile by immunohistochemistry.

Utilize Ecm4 $V_L$ and $V_E$ in preferred antibody formats e.g. whole Ig (IgGl. IgE, IgM etc.) Fab or $F(ab')_2$ fragment, or SCFV.

COMPOSITE ANTIBODIES OF HUMAN SUBGROUP IV LIGHT CHAIN CAPABLE OF BINDING TO TAG-72

CROSS-REFERENCE TO RELATED APPLICATION

The present application is a divisional application from copending U.S. Ser. No. 08/261,354, filed Jun. 16, 1994 (now pending), which is a continuation-in-part application of U.S. Ser. No. 07/964,536, filed Oct. 20, 1992 (now abandoned), and a continuation-in-part application of U.S. Ser. No. 07/510,697, filed Jul. 17, 1990 (now abandoned).

FIELD OF THE INVENTION

The present invention is directed to the fields of immunology and genetic engineering.

BACKGROUND OF THE INVENTION

The following information is provided for the purpose of making known information believed by the applicants to be of possible relevance to the present invention. No admission is necessarily intended, nor should be construed, that any of the following information constitutes prior art against the present invention.

Antibodies are specific immunoglobulin (Ig) polypeptides produced by the vertebrate immune system in response to challenges by foreign proteins, glyco-proteins, cells, or other antigenic foreign substances. The binding specificity of such polypeptides to a particular antigen is highly refined, with each antibody being almost exclusively directed to the particular antigen which elicited it.

Two major methods of generating vertebrate antibodies are presently utilized: generation in situ by the mammalian B lymphocytes and generation in cell culture by B cell hybrids. Antibodies are generated in situ as a result of the differentiation of immature B lymphocytes into plasma cells (see Gough (1981), *Trends in Biochem Sci,* 6:203). Even when only a single antigen is introduced into the immune system of a particular mammal, a uniform population of antibodies does not result, i.e., the response is polyclonal.

The limited but inherent heterogeneity of polyclonal antibodies is overcome by the use of hybridoma technology to create "monoclonal" antibodies in cell cultures by B cell hybridomas (see Kohler and Milstein (1975), *Nature,* 256:495–497). In this process, a mammal is injected with an antigen, and its relatively short-lived, or mortal, splenocytes or lymphocytes are fused with an immortal tumor cell line. The fusion produces hybrid cells or "hybridomas" which are both immortal and capable of producing the genetically-coded antibody of the B cell.

In many applications, the use of monoclonal antibodies produced in non-human animals is severely restricted where the monoclonal antibodies are to be used in humans. Repeated injections in humans of a "foreign" antibody, such as a mouse antibody, may lead to harmful hypersensitivity reactions, i.e., an anti-idiotypic, or anti-mouse antibody (HAMA), response (see Shawler et al. (1985), *Journal of Immunology,* 135:1530–1535; and Sear et al., *J. Biol. Resp. Modifiers,* 3:138–150).

Various attempts have already been made to manufacture human-derived monoclonal antibodies by using human hybridomas (see Olsson et al. (1980), *Proc. Natl. Acad. Sci. USA,* 77:5429; and Roder et al. (1986), *Methods in Enzymology,* 121:140–167). Unfortunately, yields of monoclonal antibodies from human hybridoma cell lines are relatively low compared to mouse hybridomas. In addition, human cell lines expressing immunoglobulins are relatively unstable compared to mouse cell lines, and the antibody producing capability of these human cell lines is transient. Thus, while human immunoglobulins are highly desirable, human hybridoma techniques have not yet reached the stage where human monoclonal antibodies with required antigenic specificities can be easily obtained.

Thus, antibodies of nonhuman origin have been genetically engineered, or "humanized". Humanized antibodies reduce the HAMA response compared to that expected after injection of a human patient with a mouse antibody. Humanization of antibodies derived from nonhumans, for example, has taken two principal forms, i.e., chimerization where non-human regions of immunoglobulin constant sequences are replaced by corresponding human ones (see U.S. Pat. No. 4,816,567 to Cabilly et al., Genentech) and grafting of complementarity determining regions (CDR) into human framework regions (FR) (see European Patent Office Application (EPO) 0 239 400 to Winter). Some researchers have produced Fv antibodies (see U.S. Pat. No. 4,642,334 to Moore, DNAX) and single chain Fv (SCFV) antibodies (see U.S. Pat. No. 4,946,778 to Ladner, Genex).

The above patent publications only show the production of antibody fragments in which some portion of the variable domains is coded for by nonhuman V gene regions. Humanized antibodies to date still retain various portions of light and heavy chain variable regions of nonhuman origin: the chimeric, Fv and single chain Fv antibodies retain the entire variable region of nonhuman origin and CDR-grafted antibodies retain CDR of nonhuman origin.

Such non-human-derived regions are expected to elicit an immunogenic reaction when administered into a human patient (see Brüggemann et al. (1989), *J. Exp. Med.,* 170:2153–2157; and Lo Buglio (1991), Sixth International Conference on Monoclonal Antibody Immunoconjugates for Cancer, San Diego, Calif.). Thus, it is most desirable to obtain a human variable region which is capable of binding to a selected antigen.

One known human carcinoma tumor antigen is tumor-associated glycoprotein-72 (TAG-72), as defined by monoclonal antibody B72.3 (see Thor et al. (1986) *Cancer Res.,* 46:3118–3124; and Johnson, et al. (1986), *Cancer Res.,* 46:850–857). TAG-72 is associated with the surface of certain tumor cells of human origin, specifically the LS174T tumor cell line (American Type Culture Collection (ATCC) No. CL 188), which is a variant of the LS180 (ATCC No. CL 187) colon adenocarcinoma line.

Numerous murine monoclonal antibodies have been developed which have binding specificity for TAG-72. Exemplary murine monoclonal antibodies include the "CC" (colon cancer) monoclonal antibodies, which are a library of murine monoclonal antibodies developed using TAG-72 purified on an immunoaffinity column with an immobilized anti-TAG-72 antibody, B72.3 (ATCC HB-8108) (see EP 394277, to Schlom et al., National Cancer Institute). Certain CC antibodies were deposited with the ATCC: CC49 (ATCC No. HB 9459); CC83 (ATCC No. HB 9453); CC46 (ATCC No. HB 9458); CC92 (ATCC No. HB 9454); CC30 (ATCC NO. HB 9457); CC11 (ATCC No. 9455) and CC15 (ATCC No. HB 9460). Various antibodies of the CC series have been chimerized (see, for example, EPO 0 365 997 to Mezes et al., The Dow Chemical Company).

It is thus of great interest to develop antibodies against TAG-72 containing a light and/or heavy chain variable region(s) derived from human antibodies. However, the prior art simply does not teach recombinant and immunologic techniques capable of routinely producing an anti-TAG-72 antibody in which the light chain and/or the heavy chain variable regions have specificity and affinity for TAG-72 and which are derived from human sequences so as to elicit expectedly low or no HAMA response. It is known that the function of an immunoglobulin molecule is dependent on its three dimensional structure, which in turn is dependent on its primary amino acid sequence. A change of a few or even one amino acid can drastically affect the binding function of the antibody, i.e., the resultant antibodies are generally presumed to be a non-specific immunoglobulin (NSI), i.e., lacking in antibody character, (see, for example, U.S. Pat. No. 4,816,567 to Cabilly et al., Genentech).

SUMMARY OF THE INVENTION

Surprisingly, the present invention is capable of meeting many of these above-mentioned needs and provides a method for supplying the desired antibodies. For example, in one aspect, the present invention provides a cell capable of expressing a composite antibody having binding specificity for TAG-72, said cell being transformed with (a) a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) capable of combining with the $V_L$ into a three dimensional structure having the ability to bind to TAG-72. As is customary in the art, the term "Hum4 $V_L$" which is itself derived from the designation of a protein—i.e. the light chain belonging to Subgroup IV of the class of human K light chains—can indicate this protein and/or the gene(s) of DNA sequence(s) which encode it.

In one aspect, the present invention concerns a composite antibody or antibody fragment comprising a DNA sequence encoding at least one chain which comprises a variable region having a heavy chain ($V_H$) and a light chain ($V_L$), (A) said $V_H$ being encoded by a DNA sequence comprising a subsegment effectively homologous to the $V_H\alpha$TAG germline gene ($V_H\alpha$TAG), and (B) said $V_L$ being encoded by a DNA sequence comprising a subsegment effectively homologous to the human Subgroup IV germline gene (Hum$_k$IV).

In another aspect, the present invention provides a composite antibody or antibody fragment having binding specificity for TAG-72, comprising (a) a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) capable of combining with the $V_L$ into a three dimensional structure having the ability to bind TAG-72.

The invention further includes the aforementioned antibody alone or conjugated to an imaging marker or therapeutic agent. The invention also includes a composition comprising the aforementioned antibody in unconjugated or conjugated form in a pharmaceutically acceptable, non-toxic, sterile carrier.

The invention is also directed to a method for in vivo diagnosis of cancer which comprises administering to an animal containing a tumor expressing TAG-72 a pharmaceutically effective amount of the aforementioned composition for the in situ detection of carcinoma lesions.

The invention is also directed to a method for intraoperative therapy which comprises (a) administering to a patient containing a tumor expressing TAG-72 a pharmaceutically effective amount of the aforementioned composition, whereby the tumor is localized, and (b) excising the localized tumors.

Additionally, the invention also concerns a process for preparing and expressing a composite antibody. Some of these processes are as follows. A process which comprises transforming a cell with a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) which is capable of combining with the $V_L$ to form a three dimensional structure having the ability to bind to TAG-72. A process for preparing a composite antibody or antibody which comprises culturing a cell containing a DNA sequence encoding at least a portion of a light chain variable region ($V_L$) effectively homologous to the human Subgroup IV germline gene (Hum4 $V_L$); and a DNA sequence segment encoding at least a portion of a heavy chain variable region ($V_H$) capable of combining with the $V_L$ into a three dimensional structure having the ability to bind to TAG-72 under sufficient conditions for the cell to express the immunoglobulin light chain and immunoglobulin heavy chain. A process for preparing an antibody conjugate comprising contacting the aforementioned antibody or antibody with an imaging marker or therapeutic agent.

BRIEF DESCRIPTION OF THE DRAWINGS

FIG. 2, i.e. FIGS. 2A–2G, illustrate the nucleotide sequences of $V_H\alpha$TAG, CC46 $V_H$, CC49 $V_H$, CC83 $V_H$ and CC92 $V_H$.

FIG. 3, i.e. FIGS. 3A–3E illustrate the amino acid sequences of $V_H\alpha$TAG, CC46 $V_H$, CC49 $V_H$, CC83 $V_H$ and CC92 $V_H$.

FIG. 4, i.e. FIGS. 4A and 4B illustrate the $V_H$ nucleotide and amino acid sequences of antibody B17X2.

FIG. 5, i.e. FIGS. 5A and 5B illustrate the mouse germline J-H genes from pNP9.

FIG. 8, i.e. FIGS. 8A and 8B illustrate the entire sequence of HUMVL(+) and HUMVL(−).

FIG. 9 illustrates the human J4 (HJ4) nucleotide sequence and amino acid sequence.

FIG. 10, i.e. FIGS. 10A–10E illustrate the nucleotide sequences, and the amino acid sequences of Hum4 $V_L$, ClaI-HindIII segment.

FIG. 15 illustrates a primer, NE0102SEQ, used for sequencing plasmid DNA from several clones of pSV2neo-102.

FIG. 17 illustrates a partial nucleotide sequence segment of pRL1000.

FIGS. 20-1, 20-2, and 20-3 illustrate a competition assay for binding to TAG using a composite Hum4 $V_L$, $V_H \alpha$TAG antibody.

FIG. 22, i.e. FIGS. 22A–22C illustrate the nucleotide sequence and amino acid sequence of SCFV1.

FIG. 24, i.e.

FIG. 26, i.e. FIGS. 26A–26D show the DNA sequence and amino acid sequence of Hum4 $V_L$-CC49$V_H$ SCFV present in pSCFVUHH.

FIG. 28, i.e. FIGS. 28A–28C illustrate the nucleotide sequence of FLAG peptide adapter in pATDFLAG.

FIG. 30, i.e. FIGS. 30A–30D illustrate the nucleotide and amino acid sequences of pSC49FLAG.

FIG. 31, i.e. FIGS. 31A–31B show the flow diagram for the discovery of Hum4 $V_L$-$V_H$ combinations that compete with prototype TAG-binding antibodies or mimetics.

DETAILED DESCRIPTION OF THE INVENTION

Nucleic acids, amino acids, peptides, protective groups, active groups and so on, when abbreviated, are abbreviated according to the IUPAC IUB (Commission on Biological Nomenclature) or the practice in the fields concerned.

The basic immunoglobulin structural unit is set forth in FIG. 1. The terms "constant" and "variable" are used functionally. The variable regions of both light ($V_L$) and heavy ($V_H$) chains determine binding recognition and specificity to the antigen. The constant region domains of light ($C_L$) and heavy ($C_H$) chains confer important biological properties such as antibody chain association, secretion, transplacental mobility, complement binding, binding to Fc receptors and the like.

The immunoglobulins of this invention have been developed to address the problems of the prior art. The methods of this invention produce, and the invention is directed to, composite antibodies. By "composite antibodies" is meant immunoglobulins comprising variable regions not hitherto found associated with each other in nature. By "composite Hum4 $V_L$, $V_H$ antibody" means an antibody or immunoreactive fragment thereof which is characterized by having at least a portion of the $V_L$ region encoded by DNA derived from the Hum4 $V_L$ germline gene and at least a portion of a $V_H$ region capable of combining with the $V_L$ to form a three dimensional structure having the ability to bind to TAG-72.

The composite Hum4 $V_L$, $V_H$ antibodies of the present invention assume a conformation having an antigen binding site which binds specifically and with sufficient strength to TAG-72 to form a complex capable of being isolated by using standard assay techniques (e.g., enzyme-linked immunosorbent assay (ELISA), radioimmunoassay (RIA), or fluorescence-activated cell sorter analysis (FACS), immunohistochemistry and the like). Preferably, the composite Hum4 $V_L$, $V_H$ antibodies of the present invention have an antigen binding affinity or avidity greater than $10^5$ $M^{-1}$, more preferably greater than $10^6$ $M^{-1}$ and most preferably greater than $10^8$ $M^{-1}$. For a discussion of the techniques for generating and reviewing immunoglobulin binding affinities see Munson (1983), *Methods Enzymol.,* 92:543–577 and Scatchard (1949), *Ann. N.Y. Acad. Sci.,* 51:660–672.

Human antibody kappa chains have been classified into four subgroups on the basis of invariant amino acid sequences (see, for example, Kabat et al. (1991), *Sequences of Proteins of Immunological Interest* (4th ed.), published by The U.S. Department of Health and Human Services). There appear to be approximately 80 human $V_K$ genes, but only one Subgroup IV $V_K$ gene has been identified in the human genome (see Klobeck, et al. (1985), *Nucleic Acids Research,* 13:6516–6528). The nucleotide sequence of Hum4 $V_L$ is set forth in Kabat et al. (1991), supra.

It has been found, quite surprisingly, that an immunoglobulin having a light chain with at least a portion of the $V_L$ encoded by a gene derived from Hum4 $V_L$ may, if combined with a suitable $V_H$, have binding specificity for TAG-72.

The type of $J_L$ gene segment selected is not critical to the invention, in that it is expected that any $J_L$, if present, can associate with the Hum4 $V_L$. The present invention obviously contemplates the Hum4 $V_L$ in association with a human $J_K$ sequence. The five human $J_K$ sequences are set forth in Heiter et al. (1982), *The Journal of Biological Chemistry,* 357:1516–1522. However, the present invention is not intended to be limited to the human $J_K$. The present invention specifically contemplates the Hum4 $V_L$ in association with any of the at least six human $J_\lambda$ genes (see Hollis et al. (1982), *Nature,* 296:321–325).

An exemplary technique for engineering the Hum4 $V_L$ with selected $J_L$ segments includes synthesizing a primer having a so-called "wagging tail", that does not hybridize with the target DNA; thereafter, the sequences are amplified and spliced together by overlap extension (see Horton et al. (1989), *Gene,* 77:61–68).

The $C_L$ of the composite Hum4 $V_L$, $V_H$ antibodies is not critical to the invention. To date, the Hum4 $V_L$ has only been reported as having been naturally rearranged with the single $C_k$ gene (see Heiter et al. (1980), Cell, 22:197–207). However, the present invention is not intended to be limited to the $C_K$ light chain constant domain. That is, the $C_L$ gene segment may also be any of the at least six $C_\lambda$ genes (see Hollis et al., supra).

The DNA encoding the heavy chain variable region consists roughly of a heavy chain variable ($V_H$) gene sequence, a heavy chain diversity ($D_H$) gene sequence, and a heavy chain joining ($J_H$) gene sequence.

The present invention is directed to any $V_H$ capable of combining with a light chain variable region effectively homologous to the light chain variable region encoded by the human Subgroup IV germline gene, to form a three dimensional structure having the ability to bind to TAG-72.

The choice of $D_H$ and $J_H$ segment of the composite Hum4 $V_L$, $V_H$ antibody is not critical to the present invention. Obviously, human and murine $D_H$ and $J_H$ gene segments are contemplated, provided that a given combination does not significantly decrease binding to TAG-72. Specifically, when utilizing CC46 $V_H$, CC49 $V_H$, CC83 $V_H$ and CC92 $V_H$, the composite Hum4 $V_L$, $V_H$ antibody will be designed to utilize the $D_H$ and $J_H$ segments which naturally associated with those $V_H$ of the respective hybridomas (see FIGS. 2 and 3). Exemplary murine and human $D_H$ and $J_H$ sequences are set forth in Kabat et al. (1991), supra. An exemplary technique for engineering such selected $D_H$ and $J_H$ segments with a $V_H$ sequence of choice includes synthesizing selected oligonucleotides, annealing and ligating in a cloning procedure (see, Horton et al., supra).

Figure 1:
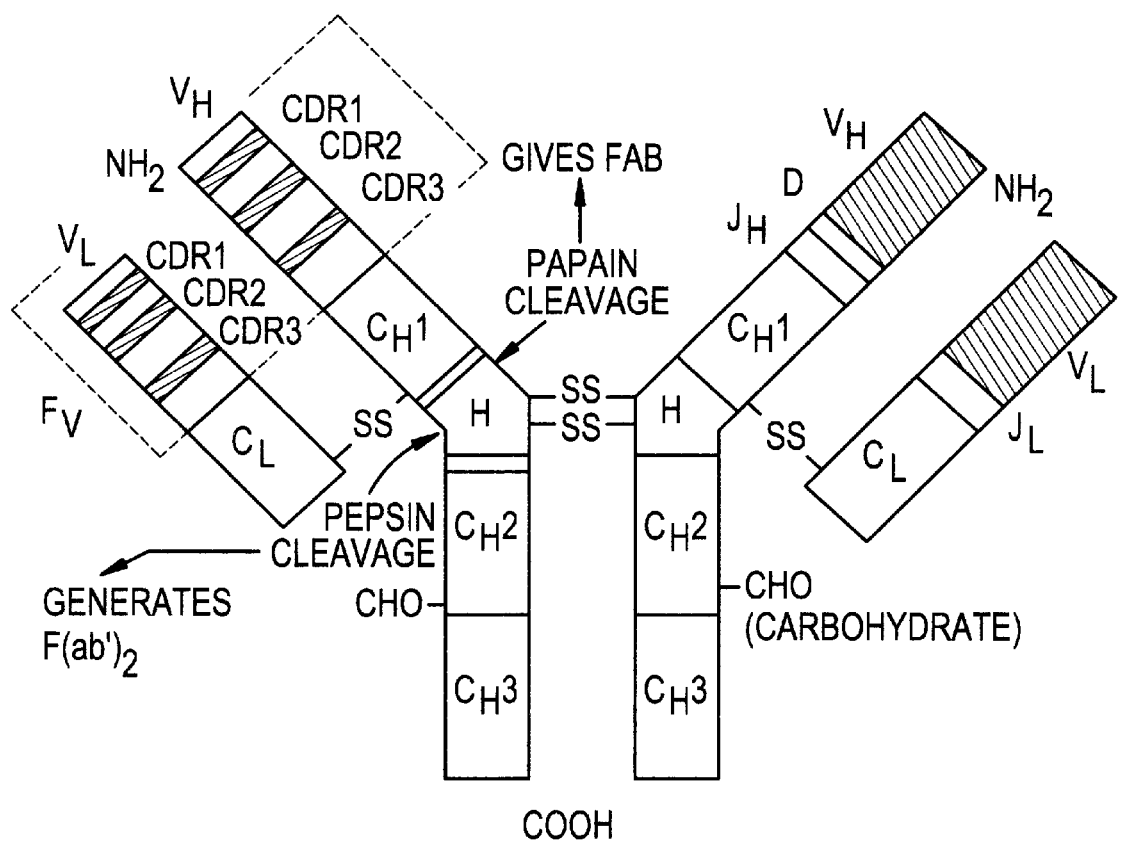
FIG. 1 illustrates a basic immunoglobulin structure.
Figure 3D:
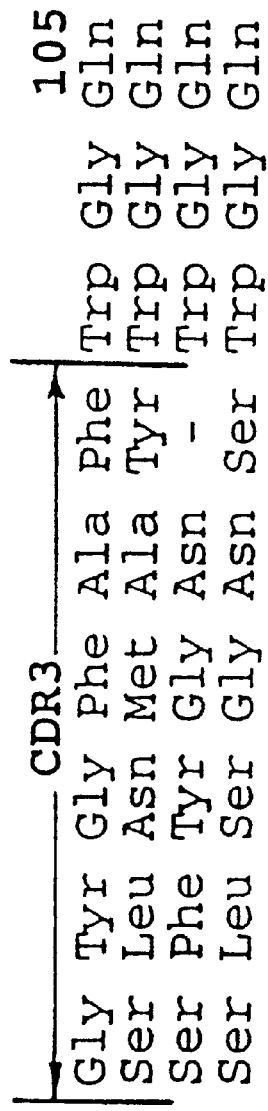

In a specific embodiment the composite Hum4 $V_L$, $V_H$ antibody will be a "composite Hum4 $V_L$, $V_H\alpha$TAG antibody", means an antibody or immunoreactive fragment thereof which is characterized by having at least a portion of the $V_L$ region encoded by DNA derived from the Hum4 $V_L$ germline gene and at least a portion of the $V_H$ region encoded by DNA derived from the $V_H\alpha$TAG germline gene, which is known in the art (see, for example, EPO 0 365 997 to Mezes et al., The Dow Chemical Company). FIG. 2 shows the nucleotide sequence of $V_H\alpha$TAG, and the nucleotide sequences encoding the $V_H$ of the CC46, CC49, CC83 and CC92 antibodies, respectively. FIG. 3 shows the corresponding amino acid sequences of $V_H\alpha$TAG, CC46 $V_H$, CC49 $V_H$, CC83 $V_H$ and CC92 $V_H$.

A comparison of the nucleotide and amino acid sequences of $V_H\alpha$TAG, CC46 $V_H$, CC49 $V_H$, CC83 $V_H$ and CC92 $V_H$ shows that those CC antibodies are derived from $V_H\alpha$TAG. Somatic mutations occurring during productive rearrangement of the $V_H$ derived from $V_H\alpha$TAG in a B cell gave rise to some nucleotide changes that may or may not result in a homologous amino acid change between the productively rearranged hybridomas (see, EPO 0 365 997).

Because the nucleotide sequences of the $V_H\alpha$TAG and Hum4 $V_L$ germline genes have been provided herein, the present invention is intended to include other antibody genes which are productively rearranged from the $V_H\alpha$TAG germline gene. Other antibodies encoded by DNA derived from $V_H\alpha$TAG may be identified by using a hybridization probe made from the DNA or RNA of the $V_H\alpha$TAG or rearranged genes containing the recombined $V_H\alpha$TAG. Specifically, the probe will include of all or a part of the $V_H\alpha$TAG germline gene and its flanking regions. By "flanking regions" is meant to include those DNA sequences from the 5' end of the $V_H\alpha$TAG to the 3' end of the upstream gene, and from 3' end of the $V_H\alpha$TAG to the 5' end of the downstream gene.

The CDR from the variable region of antibodies derived from $V_H\alpha$TAG may be grafted onto the FR of selected $V_H$, i.e., FR of a human antibody (see EPO 0 239 400 to Winter). For example, the cell line, B17X2, expresses an antibody utilizing a variable light chain encoded by a gene derived from Hum4 $V_L$ and a variable heavy chain which makes a stable $V_L$ and $V_H$ combination (see Marsh et al. (1985), Nucleic Acids Research, 13:6531–6544; and Polke et al. (1982), Immunobiol. 163:95–109. The nucleotide sequence of the $V_H$ chain for B17X2 is shown in FIG. 4. The B17X2 cell line is publicly available from Dr. Christine Polke, Universitäts-Kinderklinik, Josef-Schneider-Str. 2, 8700 Würzburg, FRG). B17X2 is directed to N-Acetyl-D-Glucosamine and is not specific for TAG-72.

However, consensus sequences of antibody derived from the CDR1 of $V_H\alpha$TAG (amino acid residues 31 to 35 of FIG. 3) may be inserted into B17X2 (amino acid residues 31 to 37 of FIG. 4) and the CDR2 of $V_H\alpha$TAG (amino residues 50 to 65 of FIG. 3) may be inserted into B17X2 (amino acid residues 52 to 67 of FIG. 4). The CDR3 may be replaced by any $D_H$ and $J_H$ sequence which does not affect the binding of the antibody for TAG-72 but, specifically, may be replaced by the CDR3 of an antibody having its $V_H$ derived from $V_H\alpha$TAG, e.g., CC46, CC49, CC83 and CC92. Exemplary techniques for such replacement are set forth in Horton et al., supra.

The $C_H$ domains of immunoglobulin heavy chain derived from $V_H\alpha$TAG genes, for example, may be changed to a human sequence by known techniques (see, U.S. Pat. No. 4,816,567 to Cabilly, Genentech). $C_H$ domains may be of various complete or shortened human isotypes, i.e., IgG (e.g., $IgG_1$, $IgG_2$, $IgG_3$, and $IgG_4$), IgA (e.g., IgA1 and IgA2), IgD, IgE, IgM, as well as the various allotypes of the individual groups (see Kabat et al. (1991), supra).

Given the teachings of the present invention, it should be apparent to the skilled artisan that human $V_H$ genes can be tested for their ability to produce an anti-TAG-72 immunoglobulin combination with the Hum4 $V_L$ gene. The $V_L$ may be used to isolate a gene encoding for a $V_H$ having the ability to bind to TAG-72 to test myriad combinations of Hum4 $V_L$ and $V_H$ that may not naturally occur in nature, e.g., by generating a combinatorial library using the Hum4 $V_L$ gene to select a suitable $V_H$. Examples of these enabling technologies include screening of combinatorial libraries of $V_L$-$V_H$ combinations using an Fab or single chain antibody (SCFV) format expressed on the surfaces of fd phage (Clackson, et al. (1991), Nature, 352:624–628), or using a λ phage system for expression of Fv's or Fabs (Huse, et al. (1989), Science, 246:1275–1281). However, according to the teachings set forth herein, it is now possible to clone SCFV antibodies in E. coli, and express the SCFVs as secreted soluble proteins. SCFV proteins produced in E. coli that contain a Hum4 $V_L$ gene can be screened for binding to TAG-72 using, for example, a two-membrane filter screening system (Skerra, et al. (1991), Analytical Biochemistry, 196:151–155).

The desired gene repertoire can be isolated from human genetic material obtained from any suitable source, e.g., peripheral blood lymphocytes, spleen cells and lymph nodes of a patient with tumor expressing TAG-72. In some cases, it is desirable to bias the repertoire for a preselected activity, such as by using as a source of nucleic acid, cells (source cells) from vertebrates in any one of various stages of age, health and immune response.

Cells coding for the desired sequence may be isolated, and genomic DNA fragmented by one or more restriction enzymes. Tissue (e.g., primary and secondary lymph organs, neoplastic tissue, white blood cells from peripheral blood and hybridomas) from an animal exposed to TAG-72 may be probed for selected antibody producing B cells. Variability among B cells derived from a common germline gene may result from somatic mutations occurring during productive rearrangement.

Generally, a probe made from the genomic DNA of a germline gene or rearranged gene can be used by those skilled in the art to find homologous sequences from unknown cells. For example, sequence information obtained from Hum4 $V_L$ and $V_H\alpha$TAG may be used to generate hybridization probes for naturally-occurring rearranged V regions, including the 5' and 3' nontranslated flanking regions. The genomic DNA may include naturally-occurring introns for portions thereof, provided that functional splice donor and splice acceptor regions had been present in the case of mammalian cell sources.

Additionally, the DNA may also be obtained from a cDNA library. mRNA coding for heavy or light chain variable domain may be isolated from a suitable source, either mature B cells or a hybridoma culture, employing standard techniques of RNA isolation. The DNA or amino acids also may be synthetically synthesized and constructed by standard techniques of annealing and ligating fragments (see Jones, et al. (1986), *Nature,* 321:522–525; Reichmann et al., (1988), Nature, 332:323–327; Sambrook et al. (1989), supra and Merrifield et al. (1963), *J. Amer. Chem. Soc.,* 85:2149–2154). Heavy and light chains may be combined in vitro to gain antibody activity (see Edelman, et al. (1963), *Proc. Natl. Acad. Sci. USA,* 50:753).

The present invention also contemplates a gene library of $V_H\alpha TAG$ homologs, preferably human homologs of $V_H\alpha TAG$. By "homolog" is meant a gene coding for a $V_H$ region (not necessarily derived from, or even effectively homologous to, the $V_H\alpha TAG$ germline gene) capable of combining with a light chain variable region effectively homologous to the light chain variable region encoded by the human Subgroup IV germline gene, to form a three dimensional structure having the ability to bind to TAG-72.

Preferably, the gene library is produced by a primer extension reaction or combination of primer extension reactions as described herein. The $V_H\alpha TAG$ homologs are preferably in an isolated form, i.e., substantially free of materials such as, for example, primer extension reaction agents and/or substrates, genomic DNA segments, and the like. The present invention thus is directed to cloning the $V_H\alpha TAG$-coding DNA homologs from a repertoire comprised of polynucleotide coding strands, such as genomic material containing the gene expressing the variable region or the messenger RNA (mRNA) which represents a transcript of the variable region. Nucleic acids coding for $V_H\alpha TAG$-coding homologs can be derived from cells producing IgA, IgD, IgE, IgG or IgM, most preferably from IgM and IgG, producing cells.

The $V_H\alpha TAG$-coding DNA homologs may be produced by primer extension. The term "primer" as used herein refers to a polynucleotide whether purified from a nucleic acid restriction digest or produced synthetically, which is capable of acting as a point of initiation of synthesis when placed under conditions in which synthesis of a primer extension product which is complimentary to a nucleic acid strand is induced, i.e., in the presence of nucleotides and an agent for polymerization such as DNA polymerase, reverse transcriptase and the like, and at a suitable temperature and pH.

Preferably, the $V_H\alpha TAG$-coding DNA homologs may be produced by polymerase chain reaction (PCR) amplification of double stranded genomic or cDNA, wherein two primers are used for each coding strand of nucleic acid to be exponentially amplified. The first primer becomes part of the nonsense (minus or complementary) strand and hybridizes to a nucleotide sequence conserved among $V_H$ (plus) strands within the repertoire. PCR is described in Mullis et al. (1987), *Meth. Enz.,* 155:335–350; and *PCR Technology,* Erlich (ed.) (1989). PCR amplification of the mRNA from antibody-producing cells is set forth in Orlandi et al. (1989), *Proc. Natl. Acad. Sci., USA,* 86:3387–3837.

According to a preferred method, the $V_H\alpha TAG$-coding DNA homologs are connected via linker to form a SCFV having a three dimensional structure capable of binding TAG-72. The SCFV construct can be in a $V_L$-L-$V_H$ or $V_H$-L-$V_L$ configuration. For a discussion of SCFV see Bird et al. (1988), *Science,* 242:423–426. The design of suitable peptide linker regions is described in U.S. Pat. No. 4,704,692 to Ladner et al., Genex.

The nucleotide sequence of a primer is selected to hybridize with a plurality of immunoglobulin heavy chain genes at a site substantially adjacent to the $V_H\alpha TAG$-coding DNA homolog so that a nucleotide sequence coding for a functional (capable of binding) polypeptide is obtained. The choice of a primer's nucleotide sequence depends on factors such as the distance on the nucleic acid from the region coding for the desired receptor, its hybridization site on the nucleic acid relative to any second primer to be used, the number of genes in the repertoire it is to hybridize to, and the like. To hybridize to a plurality of different nucleic acid strands of $V_H\alpha TAG$-coding DNA homolog, the primer must be a substantial complement of a nucleotide sequence conserved among the different strands.

The peptide linker may be coded for by the nucleic acid sequences that are part of the polynucleotide primers used to prepare the various gene libraries. The nucleic acid sequence coding for the peptide linker can be made up of nucleic acids attached to one of the primers or the nucleic acid sequence coding for the peptide linker may be derived from nucleic acid sequences that are attached to several polynucleotide primers used to create the gene libraries. Additionally, noncomplementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions (see Horton et al. (1989), *Gene,* 77:61–68).

Exemplary human $V_H$ sequences from which complementary primers may be synthesized are set forth in Kabat et al. (1991), supra; Humphries et al. (1988), *Nature,* 331:446–449; Schroeder et al. (1990), *Proc. Natl. Acad. Sci. USA,* 87:6146–6150; Berman et al. (1988), *EMBO Journal,* 7:727–738; Lee et al. (1987), *J. Mol. Biol.,* 195:761–768); Marks et al. (1991), *Eur. J. Immunol.,* 21:985–991; Willems, et al. (1991), *J. Immunol.,* 146:3646–3651; and Person et al. (1991), *Proc. Natl. Acad. Sci. USA,* 88:2432–2436. To produce $V_H$ coding DNA homologs, first primers are therefore chosen to hybridize to (i.e. be complementary to) conserved regions within the J region, CH1 region, hinge region, CH2 region, or CH3 region of immunoglobulin genes and the like. Second primers are therefore chosen to hydribidize with a conserved nucleotide sequence at the 5' end of the $V_H\alpha TAG$-coding DNA homolog such as in that area coding for the leader or first framework region.

Alternatively, the nucleic acid sequences coding for the peptide linker may be designed as part of a suitable vector. As used herein, the term "expression vector" refers to a nucleic acid molecule capable of directing the expression of genes to which they are operatively linked. The choice of vector to which a $V_H\alpha TAG$-coding DNA homologs is operatively linked depends directly, as is well known in the art, on the functional properties desired, e.g., replication or protein expression, and the host cell (either prokaryotic or eukaryotic) to be transformed, these being limitations inherent in the art of constructing recombinant DNA molecules. In preferred embodiments, the eukaryotic cell expression vectors used include a selection marker that is effective in an eukaryotic cell, preferably a drug resistant selection marker.

Expression vectors compatible with prokaryotic cells are well known in the art and are available from several commercial sources. Typical of vector plasmids suitable for prokaryotic cells are pUC8, pUC9, pBR322, and pBR329 available from BioRad Laboratories, (Richmond, Calif.), and pPL and pKK223 available from Pharmacia, (Piscataway, N.J.).

Expression vectors compatible with eukaryotic cells, preferably those compatible with vertebrate cells, can also be used. Eukaryotic cell expression vectors are well known in the art and are available from several commercial sources. Typically, such vectors are provided containing convenient restriction sites for insertion of the desired DNA homolog. Typical of vector plasmids suitable for eukaryotic cells are pSV2neo and pSv2gpt (ATCC), $pSV_L$ and pKSV-10 (Pharmacia), pBPV-1/PML2d (International Biotechnologies, Inc.), and pTDT1 (ATCC).

The use of viral expression vectors to express the genes of the $V_H\alpha$TAG-coding DNA homologs is also contemplated. As used herein, the term "viral expression vector" refers to a DNA molecule that includes a promoter sequence derived from the long terminal repeat (LTR) region of a viral genome. Exemplary phage include λ phage and fd phage (see, Sambrook, et al. (1989), *Molecular Cloning: A Laboratory Manual*, (2nd ed.), and McCafferty et al. (1990), *Nature*, 6301:552–554.

The population of $V_H\alpha$TAG-coding DNA homologs and vectors are then cleaved with an endonuclease at shared restriction sites. A variety of methods have been developed to operatively link DNA to vectors via complementary cohesive termini. For instance, complementary cohesive termini can be engineered into the $V_H\alpha$TAG-coding DNA homologs during the primer extension reaction by use of an appropriately designed polynucleotide synthesis primer, as previously discussed. The complementary cohesive termini of the vector and the DNA homolog are then operatively linked (ligated) to produce a unitary double stranded DNA molecule.

The restriction fragments of Hum4 $V_L$-coding DNA and the $V_H\alpha$TAG-coding DNA homologs population are randomly ligated to the cleaved vector. A diverse, random population is produced with each vector having a $V_H\alpha$TAG-coding DNA homolog and Hum4 $V_L$-coding DNA located in the same reading frame and under the control of the vector's promoter.

The resulting single chain construct is then introduced into an appropriate host to provide amplification and/or expression of a composite Hum4 $V_L$, $V_H\alpha$TAG homolog single chain antibody. Transformation of appropriate cell hosts with a recombinant DNA molecule of the present invention is accomplished by methods that typically depend on the type of vector used. With regard to transformation of prokaryotic host cells, see, for example, Cohen et al. (1972), *Proceedings National Academy of Science, USA*, 69:2110; and Sambrook, et al. (1989), supra. With regard to the transformation of vertebrate cells with retroviral vectors containing rDNAs, see, for example, Sorge et al. (1984), *Mol. Cell. Biol.*, 4:1730–1737; Graham et al. (1973), *Virol.*, 52:456; and Wigler et al. (1979), *Proceedings National Academy of Sciences, USA*, 76:1373–1376.

Exemplary prokaryotic strains that may be used as hosts include *E. coli*, Bacilli, and other entero-bacteriaceae such as *Salmonella typhimurium*, and various Pseudomonas. Common eukaryotic microbes include *S. cerevisiae* and *Pichia pastoris*. Common higher eukaryotic host cells include Sp2/0, VERO and HeLa cells, Chinese hamster ovary (CHO) cell lines, and W138, BHK, COS-7 and MDCK cell lines. Furthermore, it is now also evident that any cell line producing Hum4 $V_L$, e.g., the B17X2 human cell line, can be used as a recipient human cell line for introduction of a $V_H$ gene complementary to the Hum4 $V_L$ which allows binding to TAG-72. For example, the B17X2 heavy chain may be genetically modified to not produce the endogenous heavy chain by well known methods; in this way, glycosylation patterns of the antibody produced would be human and not non-human derived.

Successfully transformed cells, i.e., cells containing a gene encoding a composite Hum4 $V_L$, $V_H\alpha$TAG homolog single chain antibody operatively linked to a vector, can be identified by any suitable well known technique for detecting the binding of a receptor to a ligand. Preferred screening assays are those where the binding of the composite Hum4 $V_L$, $V_H\alpha$TAG homolog single chain antibody to TAG-72 produces a detectable signal, either directly or indirectly. Screening for productive Hum4 $V_L$ and $V_H\alpha$TAG homolog combinations, or in other words, testing for effective antigen binding sites to TAG-72 is possible by using, for example, a radiolabeled or biotinylated screening agent, e.g., antigens, antibodies (e.g., B72.3, CC49, CC83, CC46, CC92, CC30, CC11 and CC15) or anti-idiotypic antibodies (see Huse et al., supra, and Sambrook et al., supra); or the use of marker peptides to the $NH_2$- or COOH-terminus of the SCFV construct (see Hopp et al. (1988), *Biotechnology*, 6:1204–1210).

Of course, the Hum4 $V_L$-coding DNA and the $V_H\alpha$TAG-coding DNA homologs may be expressed as individual polypeptide chains (e.g., Fv) or with whole or fragmented constant regions (e.g., Fab, and $F(ab')_2$). Accordingly, the Hum4 $V_L$-coding DNA and the $V_H\alpha$TAG-coding DNA homologs may be individually inserted into a vector containing a $C_L$ or $C_H$ or fragment thereof, respectively. For a teaching of how to prepare suitable vectors see EPO 0 365 997 to Mezes et al., The Dow Chemical Company.

DNA sequences encoding the light chain and heavy chain of the composite Hum4 $V_L$, $V_H$ antibody may be inserted into separate expression vehicles, or into the same expression vehicle. When coexpressed within the same organism, either on the same or the different vectors, a functionally active Fv is produced. When the $V_H\alpha$TAG-coding DNA homolog and Hum4 $V_L$ polypeptides are expressed in different organisms, the respective polypeptides are isolated and then combined in an appropriate medium to form a Fv. See Greene et al, *Methods in Molecular Biology*, Vol. 9, Wickner et al. (ed.); and Sambrook et al., supra).

Subsequent recombinations can be effected through cleavage and removal of the Hum4 $V_L$-coding DNA sequence to use the $V_H\alpha$TAG-coding DNA homologs to produce Hum4 $V_L$-coding DNA homologs. To produce a Hum4 $V_L$-coding DNA homolog, first primers are chosen to hybridize with (i.e. be complementary to) a conserved region within the J region or constant region of immunoglobulin light chain genes and the like. Second primers become part of the coding (plus) strand and hybridize to a nucleotide sequence conserved among minus strands. Hum4 $V_L$-coding DNA homologs are ligated into the vector containing the $V_H\alpha$TAG-coding DNA homolog, thereby creating a second population of expression vectors. The present invention thus is directed to cloning the Hum4 $V_L$-coding DNA homologs from a repertoire comprised of polynucleotide coding strands, such as genomic material containing the gene expressing the variable region or the messenger RNA (mRNA) which represents a transcript of the variable region. It is thus possible to use an iterative process to define yet further, composite antibodies, using later generation $V_H\alpha$TAG-coding DNA homologs and Hum4 $V_L$-coding DNA homologs.

The present invention further contemplates genetically modifying the antibody variable and constant regions to include effectively homologous variable region and constant region amino acid sequences. Generally, changes in the variable region will be made in order to improve or otherwise modify antigen binding properties of the receptor. Changes in the constant region of the antibody will, in general, be made in order to improve or otherwise modify biological properties, such as complement fixation, interaction with membranes, and other effector functions.

"Effectively homologous" refers to the concept that differences in the primary structure of the variable region may not alter the binding characteristics of the antibody. Normally, a DNA sequence is effectively homologous to a second DNA sequence if at least 70 percent, preferably at least 80 percent, and most preferably at least 90 percent of the active portions of the DNA sequence are homologous. Such changes are permissible in effectively homologous amino acid sequences so long as the resultant antibody retains its desired property.

If there is only a conservative difference between homologous positions of sequences, they can be regarded as equivalents under certain circumstances. General categories of potentially equivalent amino acids are set forth below, wherein amino acids within a group may be substituted for other amino acids in that group: (1) glutamic acid and aspartic acid; (2) hydrophobic amino acids such as alanine, valine, leucine and isoleucine; (3) asparagine and glutamine; (4) lysine and arginine and (5) threonine and serine.

Exemplary techniques for nucleotide replacement include the addition, deletion or substitution of various nucleotides, provided that the proper reading frame is maintained. Exemplary techniques include using polynucleotide-mediated, site-directed mutagenesis, i.e., using a single strand as a template for extension of the oligonucleotide to produce a strand containing the mutation (see Zoller et al. (1982), *Nuc. Acids Res.*, 10:6487–6500; Norris et al. (1983), *Nuc. Acids Res.*, 11:5103–5112; Zoller et al. (1984), *DNA*, 3:479–488; and Kramer et al. (1982), *Nuc. Acids Res.*, 10:6475–6485) and polymerase chain reaction exponentially amplifying DNA in vitro using sequence specified oligonucleotides to incorporate selected changes (see *PCR Technology: Principles and Applications for DNA Amplification*, Erlich, (ed.) (1989); and Horton et al., supra).

Further, the antibodies may have their constant region domain modified, i.e., the $C_L$, $CH_1$, hinge, $CH_2$, $CH_3$ and/or $CH_4$ domains of an antibody polypeptide chain may be deleted, inserted or changed (see EPO 327 378 A1 to Morrison et al., the Trustees of Columbia University; U.S. Pat. No. 4,642,334 to Moore et al., DNAX; and U.S. Pat. No. 4,704,692 to Ladner et al., Genex).

Once a final construct is obtained, the composite Hum4 $V_L$, $V_H$ antibodies may be produced in large quantities by injecting the host cell into the peritoneal cavity of pristane-primed mice, and after an appropriate time (about 1–2 weeks), harvesting ascites fluid from the mice, which yields a very high titer of homogeneous composite Hum4 $V_L$, $V_H$ antibodies, and isolating the composite Hum4 $V_L$, $V_H$ antibodies by methods well known in the art (see Stramignoni et al. (1983), *Intl. J. Cancer*, 31:543–552). The host cell is grown in vivo, as tumors in animals, the serum or ascites fluid of which can provide up to about 50 mg/mL of composite Hum4 $V_L$, $V_H$ antibodies. Usually, injection (preferably intraperitoneal) of about $10^6$ to $10^7$ histocompatible host cells into mice or rats will result in tumor formation after a few weeks. It is possible to obtain the composite Hum4 $V_L$, $V_H$ antibodies from a fermentation culture broth of prokaryotic and eukaryotic cells, or from inclusion bodies of *E. coli* cells (see Buckholz and Gleeson (1991), BIO/TECHNOLOGY, 9:1067–1072. The composite Hum4 $V_L$, $V_H$ antibodies can then be collected and processed by well-known methods (see generally, *Immunological Methods*, vols. I & II, eds. Lefkovits, I. and Pernis, B., (1979 & 1981) Academic Press, New York, N.Y.; and *Handbook of Experimental Immunology*, ed. Weir, D., (1978) Blackwell Scientific Publications, St. Louis, Mo.).

The composite Hum4 $V_L$, $V_H$ antibodies can then be stored in various buffer solutions such as phosphate buffered saline (PBS), which gives a generally stable antibody solution for further use.

Uses

The composite Hum4 $V_L$, $V_H$ antibodies provide unique benefits for use in a variety of cancer treatments. In addition to the ability to bind specifically to malignant cells and to localize tumors and not bind to normal cells such as fibroblasts, endothelial cells, or epithelial cells in the major organs, the composite Hum4 $V_L$, $V_H$ antibodies may be used to greatly minimize or eliminate HAMA responses thereto. Moreover, TAG-72 contains a variety of epitopes and thus it may be desirable to administer several different composite Hum4 $V_L$, $V_H$ antibodies which utilize a variety of $V_H$ in combination with Hum4 $V_L$.

Specifically, the composite Hum4 $V_L$, $V_H$ antibodies are useful for, but not limited to, in vivo and in vitro uses in diagnostics, therapy, imaging and biosensors.

The composite Hum4 $V_L$, $V_H$ antibodies may be incorporated into a pharmaceutically acceptable, non-toxic, sterile carrier. Injectable compositions of the present invention may be either in suspension or solution form. In solution form the complex (or when desired the separate components) is dissolved in a pharmaceutically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions generally contain no more than 50 percent of the organic solvent by volume.

Injectable suspensions require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically-acceptable adjuvants, if necessary to keep the complex in suspension, may be chosen from among thickeners such as carboxymethylcellulose, polyvinylpyrrolidone, gelatin and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters. Many substances which effect the hydrophobicity, density, and surface tension of the liquid suspension medium can assist in making injectable suspensions in individual cases. For example, silicone antifoams, sorbitol, and sugars are all useful suspending agents.

Methods of preparing and administering conjugates of the composite Hum4 $V_L$, $V_H$ antibody, and a therapeutic agent are well known or readily determined. Moreover, suitable dosages will depend on the age and weight of the patient and the therapeutic agent employed and are well known or readily determined.

Conjugates of a composite Hum4 $V_L$, $V_H$ antibody and an imaging marker may be administered in a pharmaceutically effective amount for the in vivo diagnostic assays of human carcinomas, or metastases thereof, in a patient having a tumor that expresses TAG-72 and then detecting the presence of the imaging marker by appropriate detection means.

Administration and detection of the conjugates of the composite Hum4 $V_L$, $V_H$ antibody and an imaging marker, as well as methods of conjugating the composite Hum4 $V_L$, $V_H$ antibody to the imaging marker are accomplished by methods readily known or readily determined. The dosage of such conjugate will vary depending upon the age and weight of the patient. Generally, the dosage should be effective to visualize or detect tumor sites, distinct from normal tissues. Preferably, a one-time dosage will be between 0.1 mg to 200 mg of the conjugate of the composite Hum4 $V_L$, $V_H$ antibody and imaging marker per patient.

Examples of imaging markers which can be conjugated to the composite Hum4 $V_L$, $V_H$ antibody are well known and include substances which can be detected by diagnostic imaging using a gamma scanner or hand held gamma probe, and substances which can be detected by nuclear magnetic resonance imaging using a nuclear magnetic resonance spectrometer.

Suitable, but not limiting, examples of substances which can be detected using a gamma scanner include $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re, $^{188}$Re and $^{99m}$Tc. An example of a substance which can be detected using a nuclear magnetic resonance spectrometer is gadolinium.

Conjugates of a composite Hum4 $V_L$, $V_H$ antibodies and a therapeutic agent may be administered in a pharmaceutically effective amount for the in vivo treatment of human carcinomas, or metastases thereof, in a patient having a tumor that expresses TAG-72. A "pharmaceutically effective amount" of the composite Hum4 $V_L$ antibody means the amount of said antibody (whether unconjugated, i.e., a naked antibody, or conjugated to a therapeutic agent) in the pharmaceutical composition should be sufficient to achieve effective binding to TAG-72.

Exemplary naked antibody therapy includes, for example, administering heterobifunctional composite Hum4 $V_L$, $V_H$ antibodies coupled or combined with another antibody so that the complex binds both to the carcinoma and effector cells, e.g., killer cells such as T cells, or monocytes. In this method, the composite Hum4 $V_L$ antibody-therapeutic agent conjugate can be delivered to the carcinoma site thereby directly exposing the carcinoma tissue to the therapeutic agent. Alternatively, naked antibody therapy is possible in which antibody dependent cellular cytoxicity or complement dependent cytotoxicity is mediated by the composite Hum4 $V_L$ antibody.

Examples of the antibody-therapeutic agent conjugates which can be used in therapy include antibodies coupled to radionuclides, such as $^{131}$I, $^{90}$Y, $^{105}$Rh, $^{47}$Sc, $^{67}$Cu, $^{212}$Bi, $^{211}$At, $^{67}$Ga, $^{125}$I, $^{186}$Re, $^{188}$Re, $^{177}$Lu, $^{99m}$Tc, $^{153}$Sm, $^{123}$I and $^{111}$In; to drugs, such as methotrexate, adriamycin; to biological response modifiers, such as interferon and to toxins, such as ricin.

Methods of preparing and administering conjugates of the composite Hum4 $V_L$, $V_H$ antibodies and a therapeutic agent are well known or readily determined. The pharmaceutical composition may be administered in a single dosage or multiple dosage form. Moreover, suitable dosages will depend on the age and weight of the patient and the therapeutic agent employed and are well known or readily determined.

Composite Hum4 $V_L$, $V_H$ antibodies, and particularly composite Hum4 $V_L$, $V_H$ single chain antibodies thereof, are particularly suitable for radioimmunoguided surgery (RIGS). In RIGS, an antibody labeled with an imaging marker is injected into a patient having a tumor that expresses TAG-72. The antibody localizes to the tumor and is detected by a hand-held gamma detecting probe (GDP). The tumor is then excised (see Martin et al. (1988), *Amer. J. Surg.*, 156:386–392; and Martin et al. (1986), *Hybridoma*, 5:S97–S108). An exemplary GDP is the Neoprobe™ scanner, commercially available from Neoprobe Corporation, Columbus, Ohio. The relatively small size and human character of the composite Hum4 $V_L$, $V_H$ single chain antibodies will accelerate whole body clearance and thus reduce the waiting period after injection before surgery can be effectively initiated.

Administration and detection of the composite Hum4 $V_L$, $V_H$ antibody-imaging marker conjugate may be accomplished by methods well known or readily determined.

The dosage will vary depending upon the age and weight of the patient, but generally a one-time dosage of 0.1 mg to 200 mg of the composite Hum4 $V_L$, $V_H$ antibody-marker conjugate per patient is administered.

EXAMPLES

The following non-limiting examples are merely for illustration of the construction and expression of composite Hum4 $V_L$, $V_H$ antibodies. All temperatures not otherwise indicated are Centigrade. All percents not otherwise indicated are by weight.

Example 1

Figure 6:
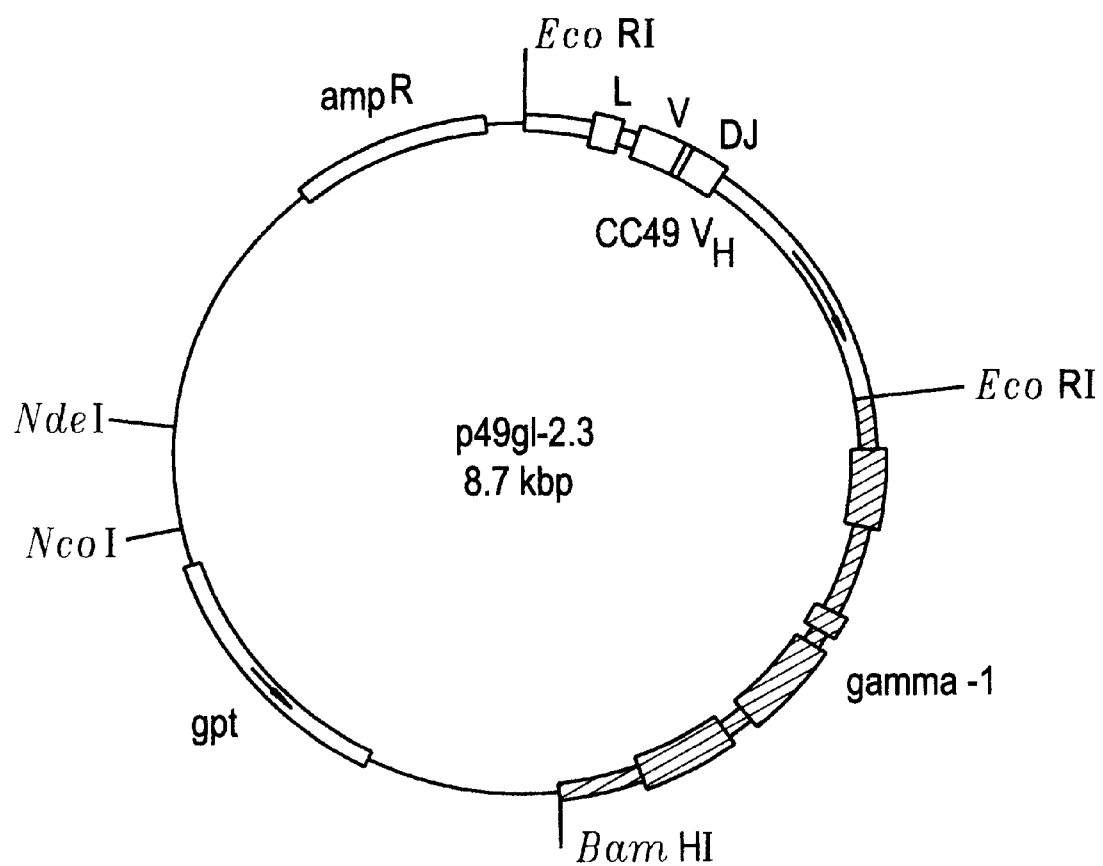
FIG. 6 illustrates the plasmid map of p49 g1-2.3.
Figure 7:
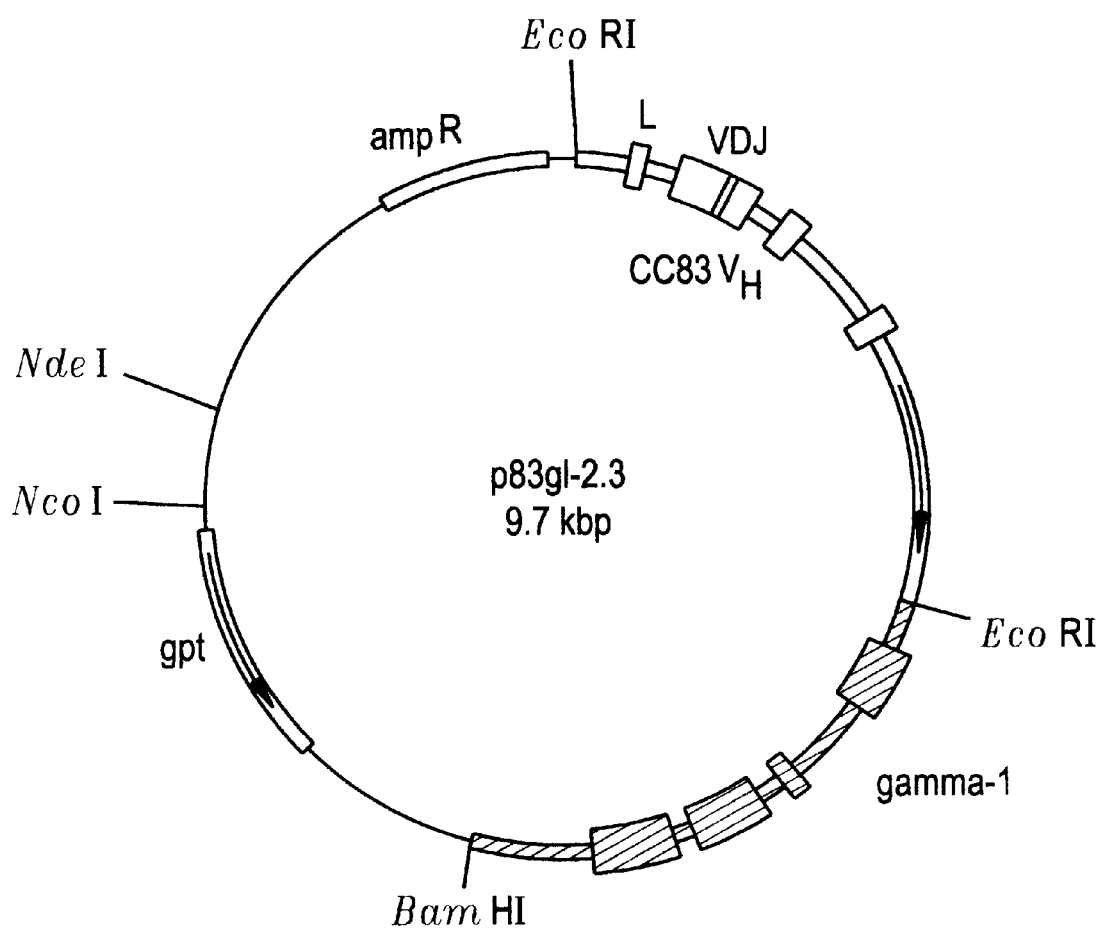
FIG. 7 illustrates the plasmid map of p83 g1-2.3.

CC49 and CC83 were isolated from their respective hybridomas using pNP9 as a probe (see FIG. 5). CC49 $V_H$ was obtained from p49 g1-2.3 (see FIG. 6) and CC83 $V_H$ was obtained from p83 g1-2.3 (see FIG. 7), following the procedures set forth in EPO 0 365 997.

DNA encoding an antibody light chain was isolated from a sample of blood from a human following the protocol of Madisen et. al. (1987), *Am. J. Med. Genet.*, 27:379–390), with several modifications. Two 5 mL purple-cap Vacutainer tubes (containing EDTA as an anticoagulant) were filled with blood and stored at ambient temperature for 2 hours. The samples were transferred to two 4.5 mL centrifuge tubes. To each tube was added 22.5 mL of filter-sterilized erythrocycte lysate buffer (0.155 M NH$_4$Cl and 0.17 M Tris, pH 7.65, in a volume ratio of 9:1), and incubated at 37° C. for 6.5 minutes. The tubes became dark red due to the lysed red blood cells. The samples were centrifuged at 9° C. for 10 minutes, using an SS-34 rotor and a Sorvall centrifuge at 5,300 revolutions per minute (rpm) (~3,400×g). The resulting white cell pellets were resuspended in 25 mL of 0.15 M NaCl solution. The white blood cells were then centrifuged as before. The pellets were resuspended in 500 µL of 0.15 M NaCl and transferred to 1.5 mL microcentrifuge tubes. The cells were pelleted again for 3 minutes, this time in the microcentrifuge at 3,000 rpm. Very few red blood cells remained on the pellet. After the supernatants were decanted from the 2 microcentrifuge tubes, 0.6 mL high TE buffer (100 mM Tris, pH 8.0) was added. The tubes were hand-shaken for between 10 and 15 minutes. The resulting viscous solution was extracted with phenol, phenol-chloroform and finally with just chloroform as described in Sambrook et al., supra. To 3.9 mL of pooled extracted DNA solution were added 0.4 mL NaOAc (3 M, pH 5), and 10 mL 100 percent ethanol. A white stringy precipitate was recovered with a yellow pipette tip, transferred into a new Eppendorf tube, washed once with 70 percent ethanol, and finally washed with 100 percent ethanol. The DNA was dried in vacuo for 1 minute and dissolved in 0.75 mL deionized water. A 20 μL aliquot was diluted to 1.0 mL and the OD 260 nm value was measured and recorded. The concentration of DNA in the original solution was calculated to be 0.30 mg/mL.

Oligonucleotides (oligos) were synthesized using phosphoramidite chemistry on a 380A DNA synthesizer (Applied Biosystems, Foster, Calif.) starting on 0.2 μM solid support columns. Protecting groups on the final products were removed by heating in concentrated ammonia solution at 55° C. for 12 hours. Crude mixtures of oligonucleotides (approximately 12 OD 260 nm units) were applied to 16 percent polyacrylamide-urea gels and electrophoresed. DNA in the gels was visualized by short wave UV light. Bands were cut out and the DNA eluted by heating the gel pieces to 65° C. for 2 hours. Final purification was achieved by application of the eluted DNA solution onto C-18 Sep-Pac™ columns (Millipore) and elution of the bound oligonucleotide with a 60 percent methanol solution. The pure DNA was dissolved in deionized, distilled water (ddH$_2$O) and quantitated by measuring OD 260 nm.

A GeneAmp™ DNA amplification kit (Cetus Corp., Emeryville, Calif.) was used to clone the Hum4 V$_L$ germline gene by the polymerase chain reaction (PCR), which was set up according to the manufacturer's directions. A thermal cycler was used for the denaturation (94° C.), annealing (45° C.) and elongation (72° C.) steps. Each of the three steps in a cycle was carried out for 4 minutes; there was a total of 30 cycles.

Upstream of the regulatory sequences in the Hum4 V$_L$ germline gene, there is a unique Cla I restriction enzyme site. Therefore, the 5' end oligonucleotide for the PCR, called HUMVL(+) (FIG. 8), was designed to include this Cla I site.

FIG. 9 shows the human J4 (HJ4) amino acid and DNA sequences. The first two amino acids (Leu-Thr) complete the CDR3 region, the remainder make up the FR4 region. Glu is underlined in HJ4 because in CC49 J5 a somatic mutation had occurred in this codon converting GAG (for Glu) to GTG (for Val). The (↓) indicates the slice site and the beginning of the intron between the J and C$_K$ exons. DNA sequences underlined in HJ4 represent parts of the sequence used for the 3' end PCR oligo.

FIG. 10 is the DNA and amino acid sequence of Hum4 V$_L$ in human/chimeric CC49H and CC83H. Specifically, the figure shows the entire DNA sequence of the Hum4 V$_L$ gene Cla I-Hind III segment in pRL1001, clone #2. A single base difference occurred at position 3461 and is marked by an asterisk (*). The corresponding amino acid sequences in the coding exons are shown. The site of the Leu Pro mutation in clone #7 is boxed. An arrow (↑) indicates the site of the single base deletion in clone #11. The coding strand is underlined to designate the sites used for hybridization of complementary oligonucleotide primers. In order the primers occur from the 5' end as follows: HUMLIN1(-); HUMLIN2(-); HUMLCDR1(-) and Hind III C$_K$(-) (not shown).

Figure 11:
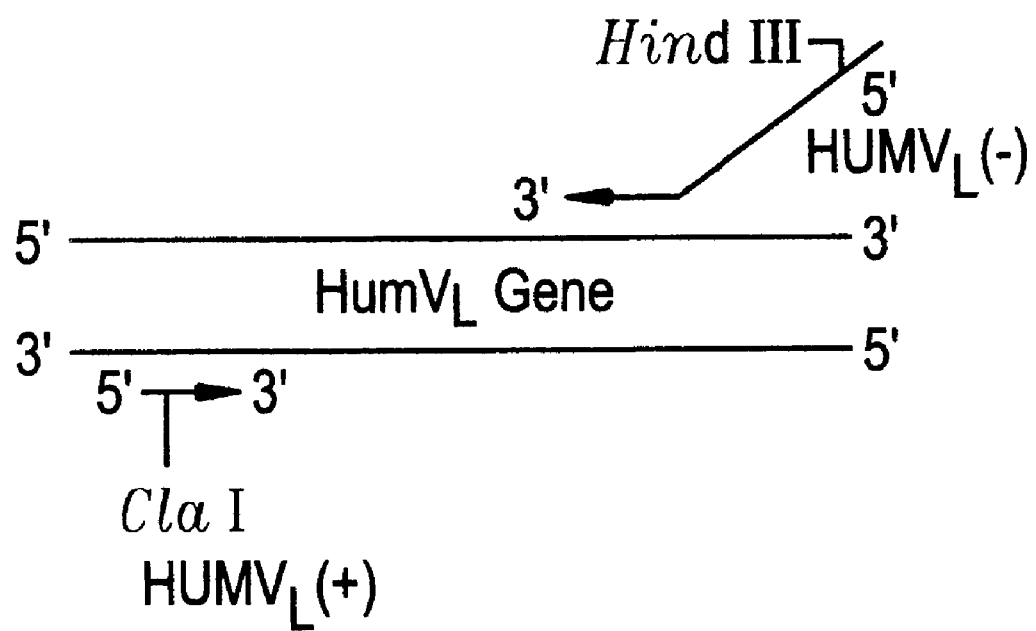
FIG. 11 illustrates a schematic representation of the human germline Subgroup IV $V_L$ gene (Hum4 $V_L$), as the target for the PCR, referring to this gene as the "human germline Subgroup IV gene (Hum $V_L$)".

The 3' end oligonucleotide, called HUMVL(-) (FIG. 8), contained a unique Hind III site; sufficient mouse intron sequence past the splicing site to permit an effective splice donor function; a human J4 sequence contiguous with the 3' end of the V$_L$ exon of Hum4 V$_L$ to complete the CDR3 and FR4 sequences of the V$_L$ domain (see FIGS. 9 and 10); nucleotides to encode a tyrosine residue at position 94 in CDR3; and 29 nucleotides close to the 3' end of the V$_L$ exon of Hum4 V$_L$ (shown underlined in the oligonucleotide HUMVL(-) in FIG. 8) to anneal with the human DNA target. In total, this 3' end oligonucleotide for the PCR was 98 bases long with a non-annealing segment (a "wagging tail") of 69 nucleotides. A schematic of the Hum4 V$_L$ gene target and the oligonucleotides used for the PCR are shown in FIG. 11. A 5'-end oligo (HUMV$_L$(+)) and the 3'-end oligo (HUMV$_L$(-)) used to prime the elongation reactions for Taq polymerase and the target Hum4 V$_L$ gene are shown.

A PCR reaction was set up with 1 μg of total human DNA in a reaction volume of 100 μL. Primers HUMVL(-) and HUMVL(+) were each present at an initial concentration of 100 pmol. Prior to the addition of Taq polymerase (2.5 units/reaction) 100 μLs of mineral oil were used to overlay the samples. Control samples were set up as outlined below. The samples were heated to 95° C. for 3 minutes. When the PCR was complete, 20 μL samples were removed for analysis by agarose gel electrophoresis.

Figure 12:
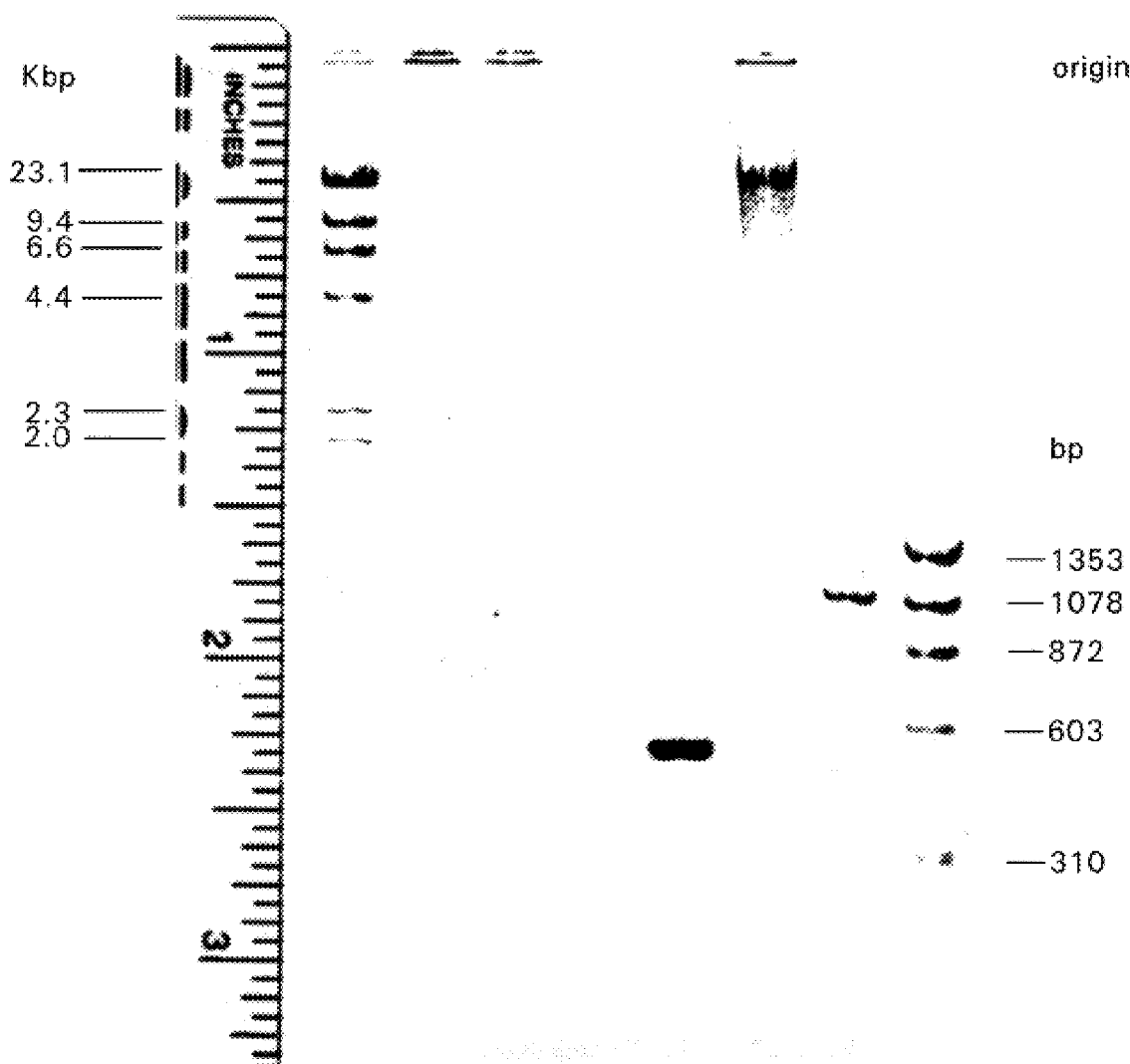
FIG. 12 shows the results of an agarose gel electrophoresis of a PCR reaction to obtain the Hum4 $V_L$ gene.

Based on the known size of the Hum4 V$_L$ DNA fragment to be cloned, and the size of the oligonucleotides used to target the gene, a product of 1099 bp was expected. A band corresponding to this size was obtained in the reaction (shown in lane 7, FIG. 12). Agarose gel electrophoresis of Hum4V$_L$PCR reactions. Lane 1: λHind III standard; lane 2:P no Taq polymerase control; lane 3: no primers added; lane 4: no human DNA template; lane 5: Gene Ampkit positive control; lane 6: 3 μg human DNA with primers and Taq polymerase; lane 7: same as lane 6, but with lug human DNA and lane 8: φX174-Hae III DNA standard. Ethidium bromide was added to the gel and buffer. Bands were visualized by long wavelength UV light.

Figure 13A:
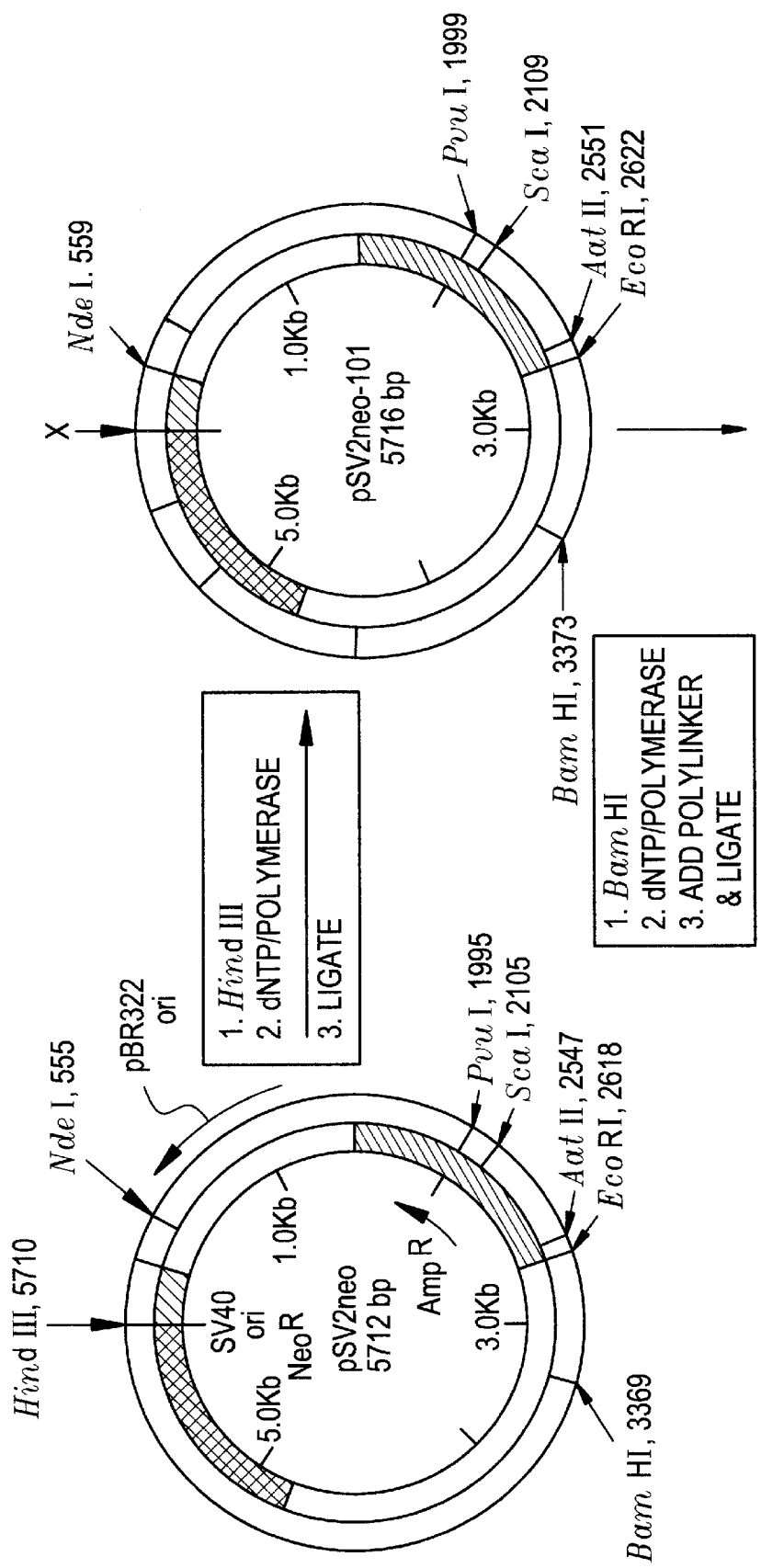
FIG. 13 illustrates the restriction enzyme maps of pRL1000, and precursor plasmids pSV2neo, pSV2neo-101 and pSV2neo-102. "X" indicates where the HindIII site of pSV2neo has been destroyed.
Figure 13B:
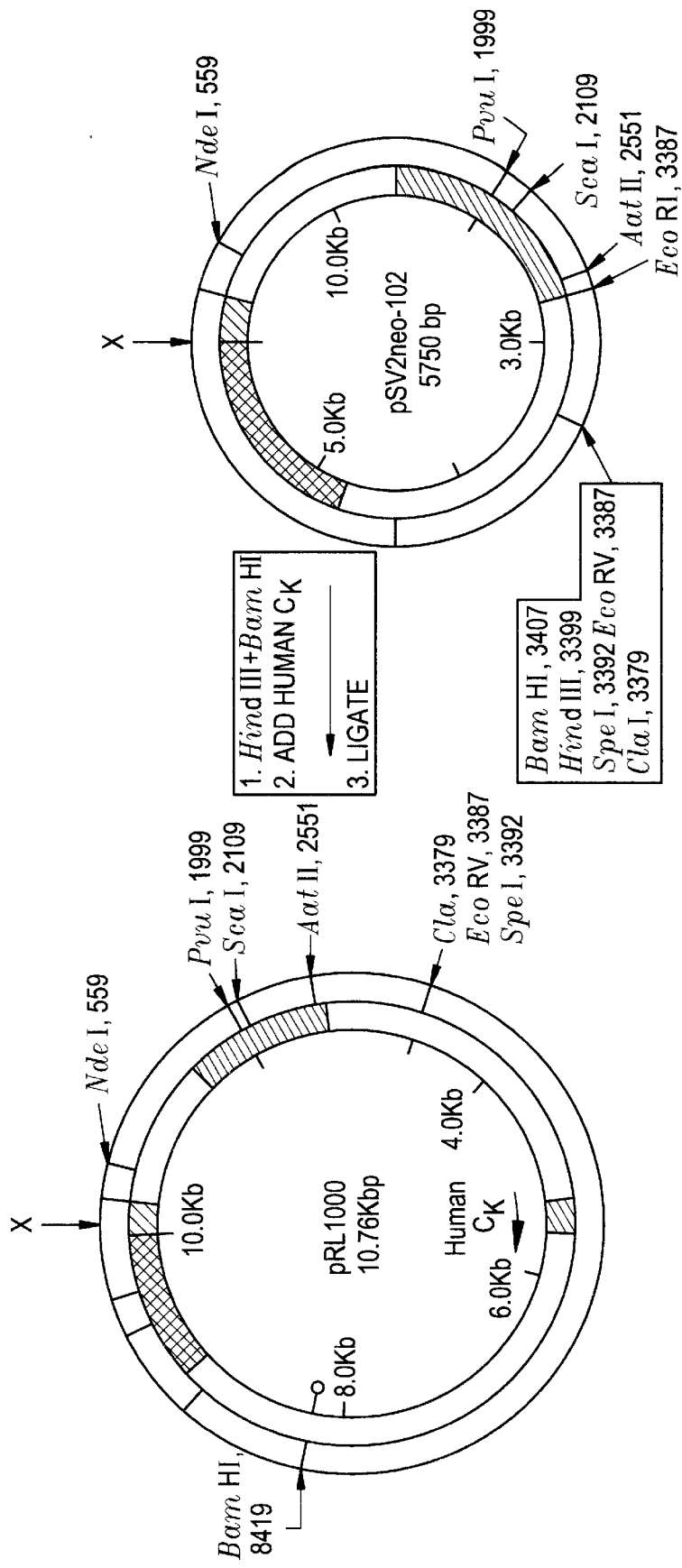

To prepare a plasmid suitable for cloning and subsequently expressing the Hum4 V$_L$ gene, the plasmid pSV2neo was obtained from ATCC and subsequently modified. pSV2neo was modified as set forth below (see FIG. 13).

The preparation of pSV2neo-101 was as follows. Ten micrograms of purified pSV2neo were digested with 40 units of Hind III at 37° C. for 1 hour. The linearized plasmid DNA was precipitated with ethanol, washed, dried and dissolved in 10 μL of water. Two microliters each of 10 mM dATP, dCTP, dGTP and dTTP were added, as well as 2 μL of 10×ligase buffer (Stratagene, La Jolla, Calif.). Five units (1 μL) of DNA polymerase I were added to make blunt the Hind III sticky ends. The reaction mixture was incubated at room temperature for 30 minutes. The enzyme was inactivated by heating the mixture to 65° C. for 15 minutes. The reaction mixture was then phenol extracted and ethanol precipitated into a pellet. The pellet was dissolved in 20 μL deionized, distilled water. A 2 μL aliquot (ca. 1 μg) was then added to a standard 20 μL ligation reaction, and incubated overnight at 4° C.

Competent E. coli DH1 cells (Invitrogen) were transformed with 1 μL and 10 μL aliquots of a ligation mix (Invitrogen, San Diego, Calif.) according to the manufacturer's directions. Ampicillin resistant colonies were obtained on LB plates containing 100 μg/mL ampicillin. Selected clones grown in 2.0 mL overnight cultures were prepared, samples of plasmid DNA were digested with Hind III and Bam HI separately, and a correct representative clone selected.

The resulting plasmid pSV2neo-101 was verified by size mapping and the lack of digestion with Hind III.

A sample of DNA (10 μg) from pSV2neo-101 mini-lysate was prepared by digesting with 50 units of Bam HI at 37° C. for 2 hours. The linearized plasmid was purified from a 4 percent polyacrylamide gel by electroelution. The DNA ends were made blunt by filling in the Bam HI site using dNTPs and Klenow fragment, as described earlier for the Hind III site of pSV2 neo-101.

Figure 14:
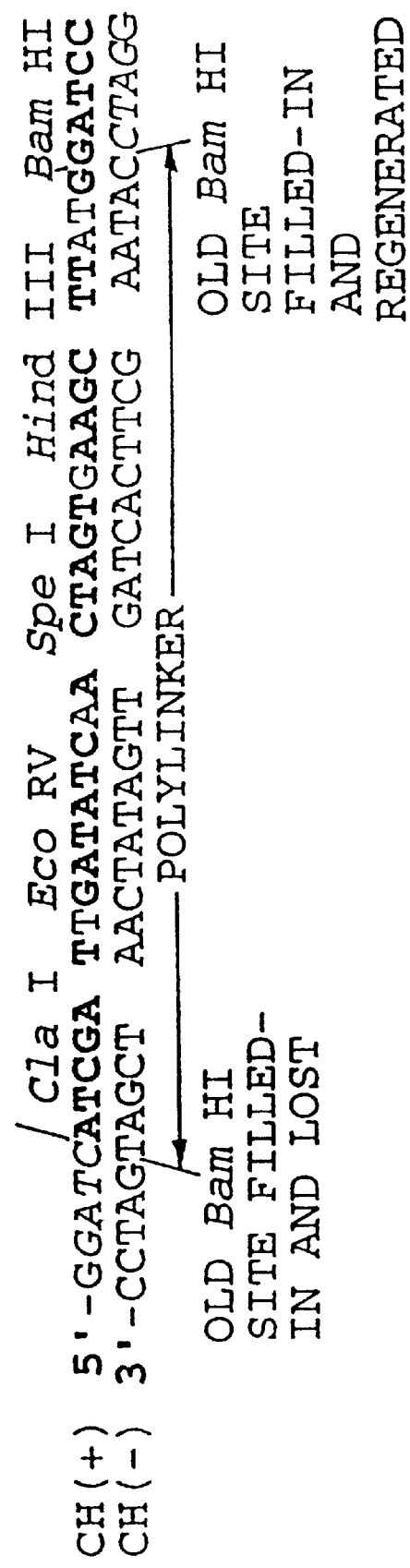
FIG. 14 illustrates a polylinker segment made by synthesizing two oligonucleotides: CH(+) and CH(−).

A polylinker segment containing multiple cloning sites was incorporated at the Bam HI site of pSV2neo-101 to create pSV2neo-102, as shown in FIG. 14. The arrow (←) indicates the direction of the Eco RI site in the vector. Note that the polylinker could be inserted in both orientations such that the Bam HI site on the left side could also be regenerated. The nucleotides used to fill-in the Bam HI site are shown in italics. The top synthetic oligo was called (CH(+) while the complimentary strand was CH(−). Equimolar amounts of two oligonucleotides, CH(+) and CH(−) (shown in FIG. 14) were annealed by heating for 3 minutes at 90° C. and cooling to 50° C. Annealed linker DNA and blunt ended pSV2neo-101 were added, in a 40:1 molar volume, to a standard 20 µL ligation reaction. $E.$ $coli$ DH1 (Invitrogen) was transformed with 0.5 µL and 5 82 L aliquots of the ligation mixture (Invitrogen). Twelve ampicillin resistant colonies were selected for analysis of plasmid DNA to determine whether the linker had been incorporated.

A Hind III digest of mini-lysate plasmid DNA revealed linker incorporation in six of the clones. The plasmid DNA from several clones was sequenced, to determine the number of linker units that were blunt-end ligated to pSV2neo-101 as well as the relative orientation(s) with the linker. Clones for sequencing were selected on the basis of positive digestion with Hind III.

A Sequenase™ sequencing kit (United States Biochemical Corp, Cleveland, Ohio) was used to sequence the DNA. A primer, NE0102SEQ, was used for sequencing and is shown in FIG. 15. It is complementary to a sequence located upstream from the BamHI site in the vector. The Bam HI site where the polylinker was inserted in pSV2neo-101 is boxed. Between 3 µg and 5 µg of plasmid DNA isolated from $E.$ $coli$ mini-lysates were used for sequencing. The DNA was denatured and precipitated prior to annealing, as according to the manufacturer's instructions. Electrophoresis was carried out at 1500 volts; gels were dried prior to exposure to Kodak X-ray film. Data was processed using a DNASIS™ computer program (Hitachi).

Figure 16:
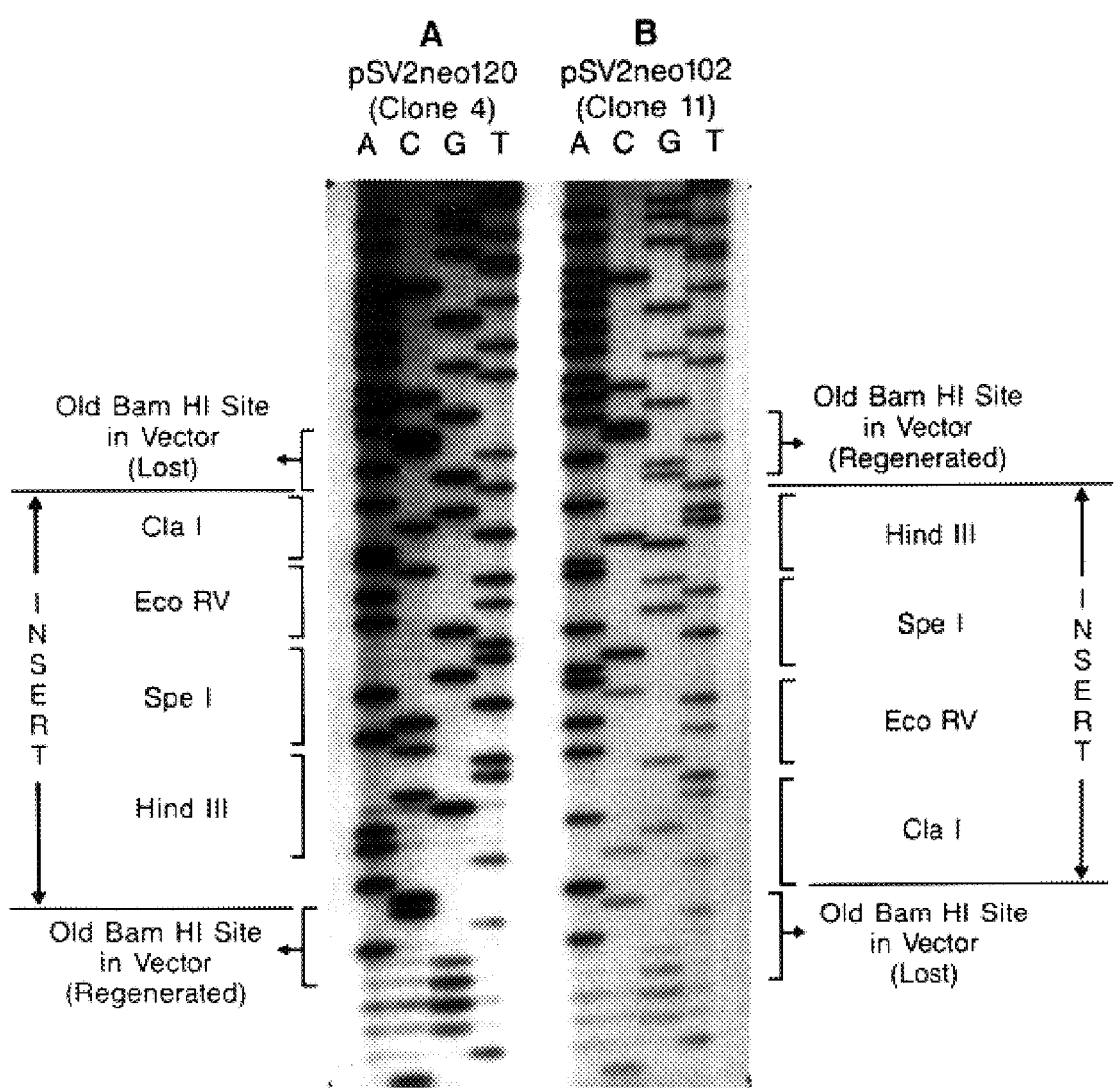
FIG. 16 illustrates an autoradiogram depicting the DNA sequence of the polylinker region both in pSV2neo-102, where the (+) strand of the polylinker DNA is inserted in the plasmid's sense strand, and in pSV2neo-120, where the (−) strand of the polylinker DNA is inserted in the plasmid's anti-sense strand.

From the DNA sequence data of 4 clones analyzed (see photograph of autoradiogram representing the sequence data of 2 of these clones- FIG. 16, reading the sequence (going up) is in the 5' to 3' direction of the (+) strand), compared to the expected sequence in FIG. 14, two clones having the desired orientation were obtained. In both cases of FIG. 16, a single 30-base linker unit was incorporated, but in opposite orientations. Panel A-Sequence resulting in pSV2neo-120; Panel B-sequencing resulting in pSVneo-102. Reading the sequence (going up) is in the 5' to 3' direction of the (+) strand. In both cases a single 30-base linker unit was incorporated, but in opposite orientations. The panel A-sequence resulted in pSV2neo-120; and the panel B sequence resulted in pSV2neo-102. A representative clone was selected and designated pSV2neo-102.

A human $C_K$ gene was inserted into pSV2neo-102 to form pRL1000. The human $C_K$ DNA was contained in a 5.0 kb Hind III-Bam HI fragment (see Hieter et al. (1980), $Cell$, 22:197–207).

A 3 µg sample of DNA from a mini-lysate of pSV2neo-102 was digested with Bam HI and Hind III. The vector DNA was separated from the small Bam HI-Hind III linker fragment, generated in the reaction, by electrophoresis on a 3.75 percent DNA polyacrylamide gel. The desired DNA fragment was recovered by electroelution. A pBR322 clone containing the 5.0 kb Hind III-Bam HI fragment of the human $C_K$ gene (see Hieter et al., supra) was designated phum$C_K$. The 5.0 kb Hind III-Bam HI fragment was ligated with pSV2neo-102 and introduced into $E.$ $coli$ DH1 (Invitrogen). Ampicillin resistant colonies were screened and a clone containing the human $C_k$ gene was designated pRL1000.

Finally, pRL1000 clones were screened by testing mini-lysate plasmid DNA from $E.$ $coli$ with Hind III and Bam HI. A clone producing a plasmid which gave 2 bands, one at 5.8 kb (representing the vector) and the other at 5.0 kb (representing the human $C_K$ insert) was selected. Further characterization of pRL1000 was achieved by sequencing downstream from the Hind III site in the intron region of the human $C_K$ insert. The oligonucleotide used to prime the sequencing reaction was NE0102SEQ (see FIG. 15). Oligonucleotide synthesized (21-mer, called NE0102SEQ) to sequence putative pSV2neo-102 clones is the underlined sequence shown above. The Bam HI site where the polylinker was inserted in pSVneo-101 is boxed.

Two hundred and seventeen bases were determined (see FIG. 17). FIG. 17 shows a DNA sequence form pRL1000, reading the (+) strand from the primer NE0102SEQ (FIG. 15). Sequence data past the Hind III site is from the human $C_K$ (−), was synthesized as a primer for sequencing in the upstream 3' direction. A new oligonucleotide corresponding to the (−) strand near the Hind III site (shown in FIG. 17) was synthesized so that clones, containing the Hum4 $V_L$ gene that were cloned into the Cla I and Hind III sites in pRL1000 (see FIG. 13), could be sequenced.

A Cla I-Hind III DNA fragment containing Hum4 $V_L$ obtained by PCR was cloned into the plasmid vector pRL1000. DNA of pRL1000 and the Hum4 $V_L$ were treated with Cla I and Hind III and the fragments were gel purified by electrophoresis, as described earlier.

Figure 18:
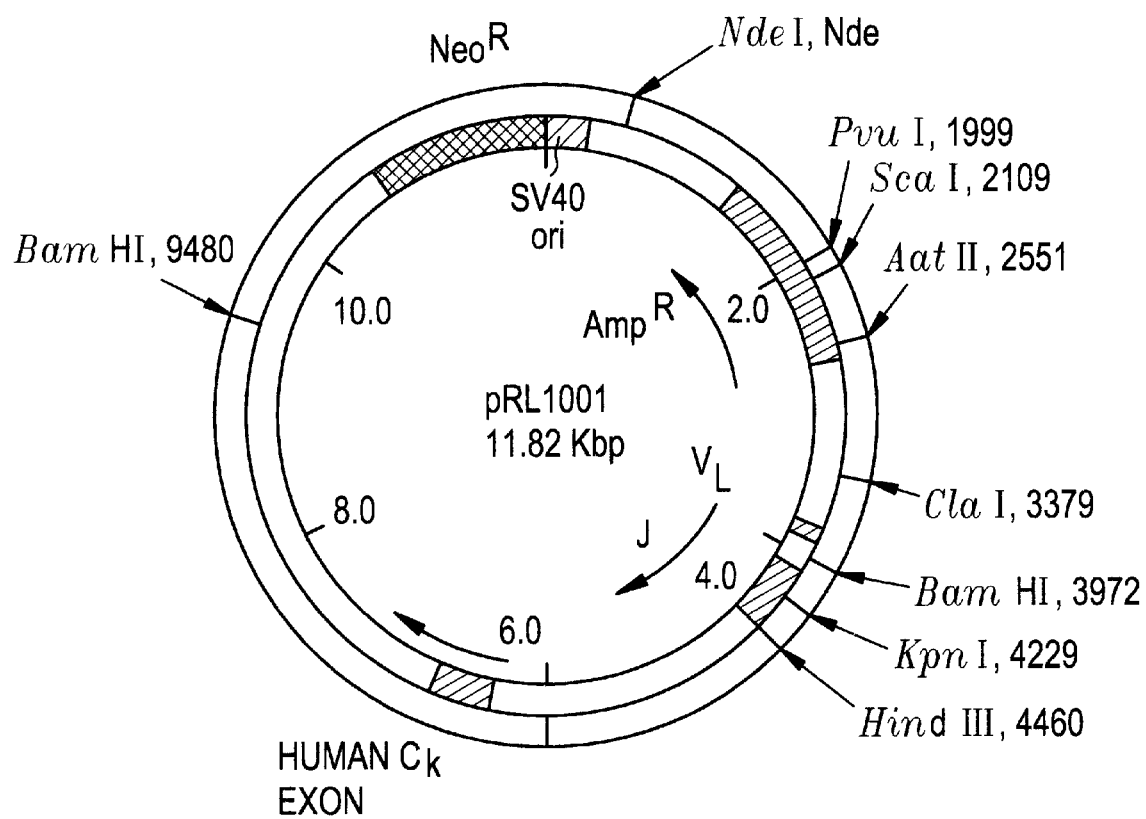
FIG. 18 illustrates the restriction enzyme map of pRL1001.

The pRL1000 DNA fragment and fragment containing Hum4 $V_L$ gene were ligated, and the ligation mixture used to transform $E.$ $coli$ DH1 (Invitrogen), following the manufacturer's protocol. Ampicillin resistant clones were screened for the presence of the Hum4 $V_L$ gene by restriction enzyme analysis and a representative clone designated pRL1001 (shown in FIG. 18). FIG. 18 shows a partial restriction map of the plasmid pRL1001. This is the expression vector to introduce the human anti-tumor L chain gene in Sp2/0 cells. This is the expression vector to introduce the human anti-tumor L chain gene in Sp2/0 cells.

Figure 19:
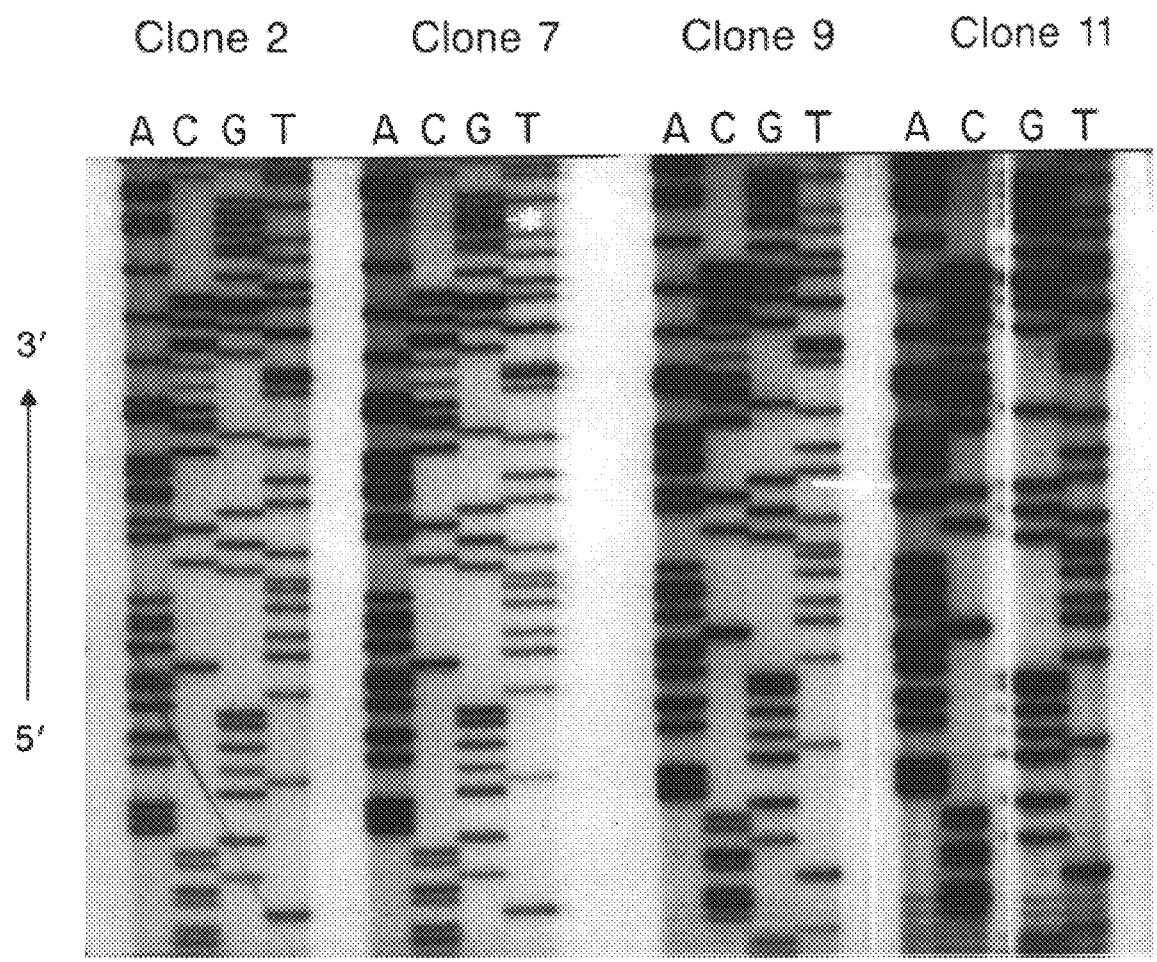
FIG. 19 illustrates an autoradiogram of DNA sequence for pRL1001 clones.
Figure 20A:
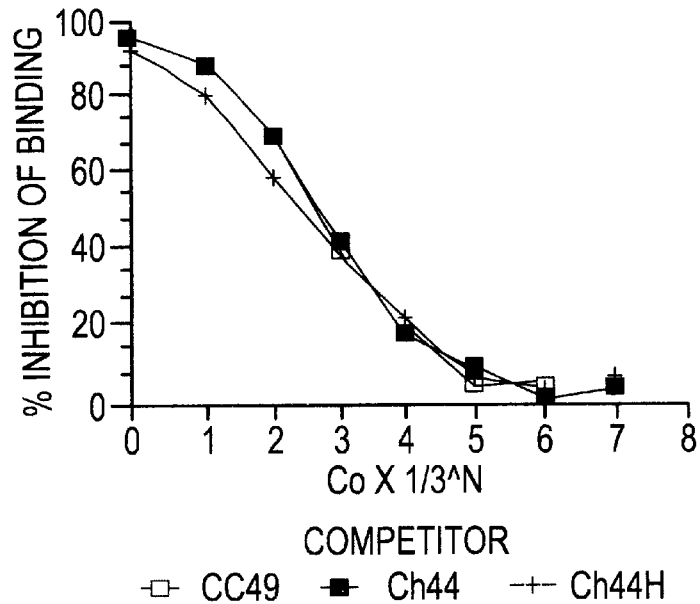
Figure 20B:
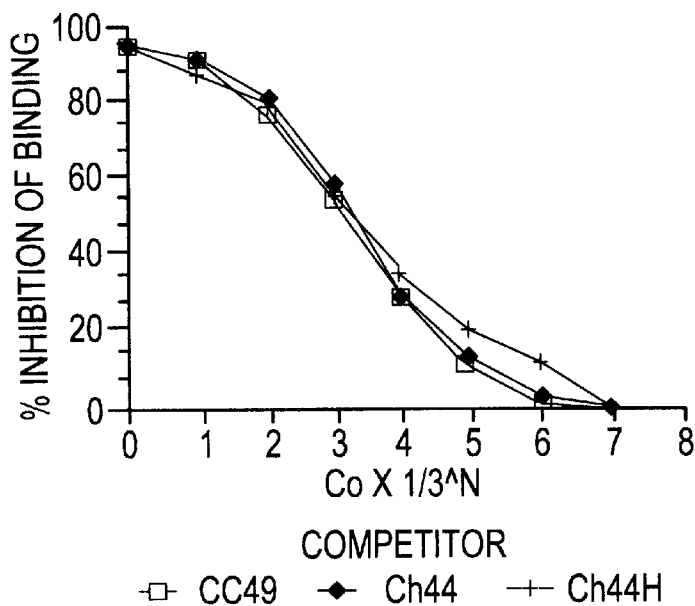

Four plasmids having the correct Cla I-Hind III restriction pattern were analyzed further by DNA sequencing of the insert region (see FIG. 19). FIG. 19 shows a DNA sequence autoradiogram of pRL1001 clones. Reading the gel is in the 5' to 3' direction on the (−) strand, from the Hind III $C_K$ (−) primer. Clones 2 and 9 were equivalent to the expected sequence, clone 7 had a single base substitution (marked by *) and clone 11 had a single base deletion (marked by −). Hind III $C_K$(−) (shown by underlining on the plus strand to which it hybridizes in FIG. 17), HUMLIN1(−) (shown by underlining on the plus strand to which it hybridizes in FIG. 10), HUMLIN2(−) (shown by underlining on the plus strand to which it hybridizes in FIG. 10) and HUMLCDR1(−) (shown by underlining on the plus strand to which it hybridizes in FIG. 10) were used as the sequencing primers. Two out of the four plasmids analyzed had the expected sequence in the coding regions (FIG. 19, clones 2 and 9). The gel is read in the 5' to 3' direction on the (−) strand, from the Hind III $C_K$ (−) primer. Clones 2 and 9 were equivalent to the expected sequence, clone 7 had a single base substitution (marked by *) and clone 11 had a single base deletion (marked by →).

Clone 2 was chosen and used for generating sufficient plasmid DNA for cell transformations and other analysis. This plasmid was used for sequencing through the Hum4 $V_L$, and the upstream region to the Cla I site. Only one change at nucleotide position 83 from a C to a G (FIG. 10) was observed, compared to a published sequence (Klobeck et al. (1985), supra). The DNA sequence data also indicates that the oligonucleotides used for PCR had been correctly incorporated into the target sequence.

A Biorad Gene Pulser™ apparatus was used to transfect Sp2/0 cells with linearized plasmid DNAs containing the light or heavy chain constructs. The Hum4 $V_L$ was introduced into Sp2/0 cells along with corresponding heavy chains by the co-transfection scheme indicated in Table 1.

TABLE 1

| | DNA Added | | |
|---|---|---|---|
| Cell Line Designation | L Chain pRL1001 | H Chain p49 gl-2.3 | H Chain p83 gl-2.3 |
| MP1-44H | 20 µg | 15 µg | 0 µg |
| MP1-84H | 20 µg | 0 µg | 15 ug |

A total of $8.0 \times 10^6$ Sp2/0 cells were washed in sterile PBS buffer (0.8 mL at $1 \times 10^7$ viable cells/mL) and held on ice for 10 minutes. DNA of pRL1001, linearized at the Cla I site, and DNA of either p49 gl-2.3 or p83 gl-2.3, linearized at their respective Nde I sites, were added, in sterile PBS, to the cells (see protocol—Table 2) and held at 0° C. for a further 10 minutes. A single 200 volt, 960 µF electrical pulse lasting between 20 and 30 milliseconds was used for the electroporation. After holding the perturbed cells on ice for 5 minutes, 25 mL of RPMI medium with 10 percent fetal calf serum were introduced, and 1.0 mL samples aliquoted in a 24 well tissue culture plate. The cells were incubated at 37° C. in a 5 percent $CO_2$ atmosphere. After 48 hours, the media was exchanged with fresh selection media, now containing both 1 mg/mL Geneticin (G418) (Difco) and 0.3 µg/ml mycophenolic acid/gpt medium. Resistant cells were cultured for between 7 and 10 days.

Supernatants from wells having drug resistant colonies were tested on ELISA plates for activity against TAG-72. A roughly 10 percent pure TAG-72 solution prepared from LSI74T tumor xenograft cells was diluted 1:40 and used to coat flexible polyvinyl chloride microtitration plates (Dynatech Laboratories, Inc.). Wells were air-dried overnight, and blocked the next day with 1 percent BSA. Supernatant samples to be tested for anti-TAG-72 antibody were added to the washed wells and incubated for between 1 and 2 hours at 37° C. Alkaline phosphatase labeled goat anti-human IgG (diluted 1:250) (Southern Biotech Associates, Birmingham, Ala.) was used as the probe antibody. Incubation was for 1 hour. The substrate used was p-nitrophenylphosphate. Color development was terminated by the addition of 1.0 N NaOH. The plates were read spectrophotometrically at 405 nm and 450 nm, and the values obtained were 405 nm–450 nm.

Those samples producing high values in the assay were subcloned from the original 24 well plate onto 96 well plates. Plating was done at a cell density of half a cell per well (nominally 50 cells) to get pure monoclonal cell lines. Antibody producing cell lines were frozen down in media containing 10 percent DMSO.

Two cell lines were procured having the designations: MP1-44H and MP1-84H. MP1-44H has the chimeric CC49 γ1 heavy chain with the Hum4 $V_L$ light chain; and MP1-84H has the chimeric CC83 γ1 heavy chain with the Hum4 $V_L$ light chain.

A 1.0 L spinner culture of the cell line MP1-44H was grown at 37° C. for 5 days for antibody production. The culture supernatant was obtained free of cells by centrifugation and filtration through a 0.22 micron filter apparatus. The clarified supernatant was passed over a Protein A cartridge (Nygene, N.Y.). Immunoglobulin was eluted using 0.1 M sodium citrate buffer, pH 3.0. The pH of the eluting fractions containing the antibody was raised to neutrality by the addition of Tris base, pH 9.0. The antibody-containing fractions were concentrated and passed over a Pharmacia Superose 12 HR 10/30 gel filtration column. A protein was judged to be homogeneous by SDS polyacrylamide gel electrophoresis. Isoelectric focusing further demonstrated the purity of MP1-44H.

The biological performance of the human composite antibody, MP1-44H, was evaluated by comparing immunohistochemistry results with two other anti-TAG-72 antibodies CC49 (ATCC No. HB 9459) and Ch44 (ATCC No. HB 9884). Sections of human colorectal tumor embedded in paraffin were tested with the three antibodies by methods familiar to those skilled in this art. All three antibodies gave roughly equivalent binding recognition of the tumor antigen present on the tumor tissue sample.

A further test of the affinity and biological integrity of the human composite antibody MP1-44H was a competition assay, based on cross-competing radioiodine-labeled versions of the antibody with CC49 and Ch44 in all combinations. From the data shown in FIGS. 20-1, 20-2, and 20-3, it is apparent that the affinity of all 3 antibodies is equivalent and can bind effectively to tumor antigen.

MP1-44H (ATCC HB 10426) and MP1-84H (ATCC HB 10427) were deposited at the American Type Culture Collection (ATCC). The contract with ATCC provides for permanent availability of the cell lines to the public on the issuance of the U.S. patent describing and identifying the deposit or the publications or upon the laying open to the public of any U.S. or foreign patent application, whichever comes first, and for availability of the cell line to one determined by the U.S. Commissioner of Patents and Trademarks to be entitled thereto according to 35 CFR §122 and the Commissioner's rules pursuant thereto (including 37 CFR §1.14 with particular reference to 886 0G 638). The assignee of the present application has agreed that if the cell lines on deposit should die or be lost or destroyed when cultivated under suitable conditions for a period of thirty (30) years or five (5) years after the last request, it will be promptly replaced on notification with viable replacement cell lines.

Example 2

Figure 21:
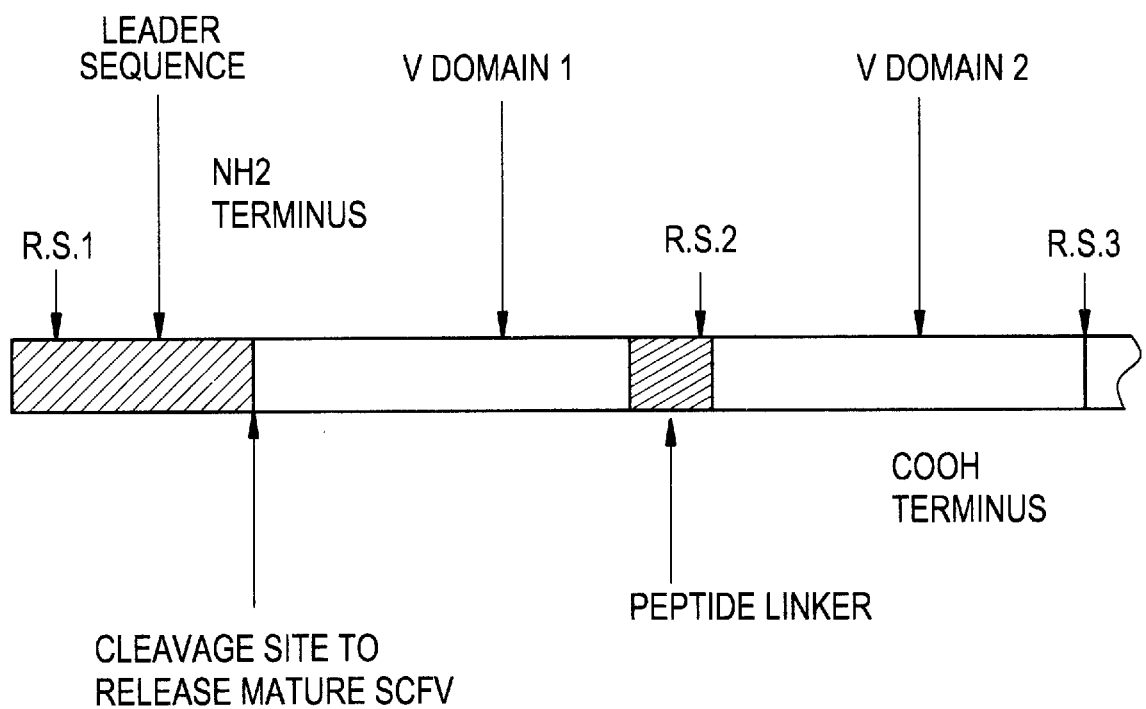
FIG. 21 illustrates a general DNA construction of a single chain, composite Hum4 $V_L$, $V_H \alpha$TAG antibody.

Single-chain antibodies consist of a $V_L$, $V_H$ and a peptide linker joining the $V_L$ and $V_H$ domains to produce SCFVs. A single chain antibody, SCFV1, was constructed to have the Hum4 $V_L$ as V Domain 1 and CC49 $V_H$ as V Domain 2 (see FIG. 21).

The polypeptide linker which joins the two V domains was encoded by DNA introduced at the 3' end of the Hum4 $V_L$ DNA during a PCR. The oligonucleotides SCFV1a and SCFV2 were designed to obtain the DNA segment incorporating part of the yeast invertase leader sequence, the Hum4 $V_L$ and the SCFV linker.

The polypeptide linker for SCFV1 was encoded in oligonucleotide SCFV1b (see below). The underlined portions of the oligonucleotides SCFV1a and SCFV1b are complementary to sequences in the Hum4 $V_L$ and linker respectively. The sequences of SCFV1a and SCFV1b are as follows, with the hybridizing sequences underlined: SCFV1a with the Hind III in bold:

5'-CTGCAAGCTTCCTTTTCCTTTTGGCTGGTTTTG

CAGCCAAAATATCTGCA<u>GACATCGTGATGACCCAGTC</u>-3'

SCFV1b with the Aat II site in bold:

5'-CGTAAGACGTC<u>TAAGGAACGAAATTGGGCCAATTGTTCTGAGGA</u>

<u>GACCGAACCTGACTCCTT</u>CACCTTGGTCCCTCCGCCG-3'

The target DNA in the PCR was pRL1001 (shown in FIG. 18). The PCR was performed pursuant to the teachings of Mullis et al., supra. A DNA fragment containing the Hum4 $V_L$-linker DNA component for the construction of SCFV1 was obtained and purified by polyacrylamide gel electrophoresis according to the teachings of Sambrook et al., supra.

p49 g1-2.3, containing CC49 $V_H$, was the target DNA in the PCR. PCR was performed according to the methods of Mullis et al., supra. The oligonucleotides used for the PCR of CC49 $V_H$ are as follows, with the hybridizing sequences underlined:

SCFV1c, with the Aat II site in bold:

5'-<u>CCTTAGACGTCCAGTTGCAGCAGTCTGACGC</u>-3'

SCFV1d, with the Hind III site in bold:

5'-GATCAAGCTTCACTAGGAGACGGTGACTGAGGTTCC-3'

The purified Hum4 $V_L$-linker and $V_H$ DNA fragments were treated with Aat II (New England Biolabs, Beverly, Mass.) according to the manufacturer's protocol, and purified from a 5 percent polyacrylamide gel after electrophoresis. An equimolar mixture of the Aat II fragments was ligated overnight. The T4 DNA ligase was heat inactivated by heating the ligation reaction mixture at 65° C. for 10 minutes. Sodium chloride was added to the mixture to give a final concentration of 50 mM and the mixture was further treated with Hind III. A Hind III DNA fragment was isolated and purified from a 4.5 percent polyacrylamide gel and cloned into a yeast expression vector (see Carter et al. (1987), In: *DNA Cloning, A Practical Approach*, Glover (ed.) Vol III: 141–161). The sequence of the fragment, containing the contiguous SCFV1 construct, is set forth in FIG. 22.

The anti-TAG-72 SCFV1 described herein utilized the yeast invertase leader sequence (shown as positions -19 to -1 of FIG. 22), the Hum4 $V_L$ (shown as positions 1 to 113 of FIG. 22), an 18 amino acid linker (shown as positions 114 to 132 of FIG. 22) and CC49 $V_H$ (shown as positions 133 to 248 of FIG. 22).

The complete DNA and amino acid sequence of SCFV1 is given in FIG. 22. The oligonucleotides used to sequence the SCFV1 are set forth below.

TPI:
5'-CAATTTTTTGTTTGTATTCTTTTC-3'.

HUVKF3:
5'-CCTGACCGATTCAGTGGCAG-3'.

DC113:
5'-TCCAATCCATTCCAGGCCCTGTTCAGG-3'.

-continued

SUC2T:
5'-CTTGAACAAAGTGATAAGTC-3'.

Example 3

A plasmid, pCGS517 (FIG. 23), containing a prorennin gene was digested with Hind III and a 6.5 kb fragment was isolated. The plasmid pCGS517 has a triosephosphate isomerase promoter, invertase [SUC2] signal sequence, the prorennin gene and a [SUC2] terminator. The Hind III-digested SCFV1 insert obtained above (see FIG. 23) was ligated overnight with the Hind III fragment of pCGS517 using T4 DNA ligase (Stratagene, La Jolla, Calif.).

The correct orientation existed when the Hind III site of the insert containing part of the invertase signal sequence ligated to the vector DNA to form a gene with a contiguous signal sequence. *E. coli* DHI (Invitrogen) cells were transformed and colonies screened using a filter-microwave technique (see Buluwela, et al. (1989), *Nucleic Acids Research*, 17:452). From a transformation plate having several hundred colonies, 3 positive clones were obtained. Digesting the candidate plasmids with Sal I and Kpn I, each a single cutter, differentiated between orientations by the size of the DNA fragments produced. A single clone, pDYS-CFV1 (FIG. 23), had the correct orientation and was used for further experimentation and cloning. The probe used was derived from pRL1001, which had been digested with Kpn I and Cla I (see FIG. 18). The probe DNA was labeled with $^{32}$p a-dCTP using a random oligonucleotide primer labeling kit (Pharmacia LKB Biotechnology, Piscataway, N.J.).

The next step was to introduce the Bgl II-Sal 1 fragment from pDYSCFV1 into the same restriction sites of another vector (ca. 9 kb), which was derived from PCGS515 (FIG. 23), to give an autonomously replicating plasmid in *S. cerevisiae*.

Figure 23A:
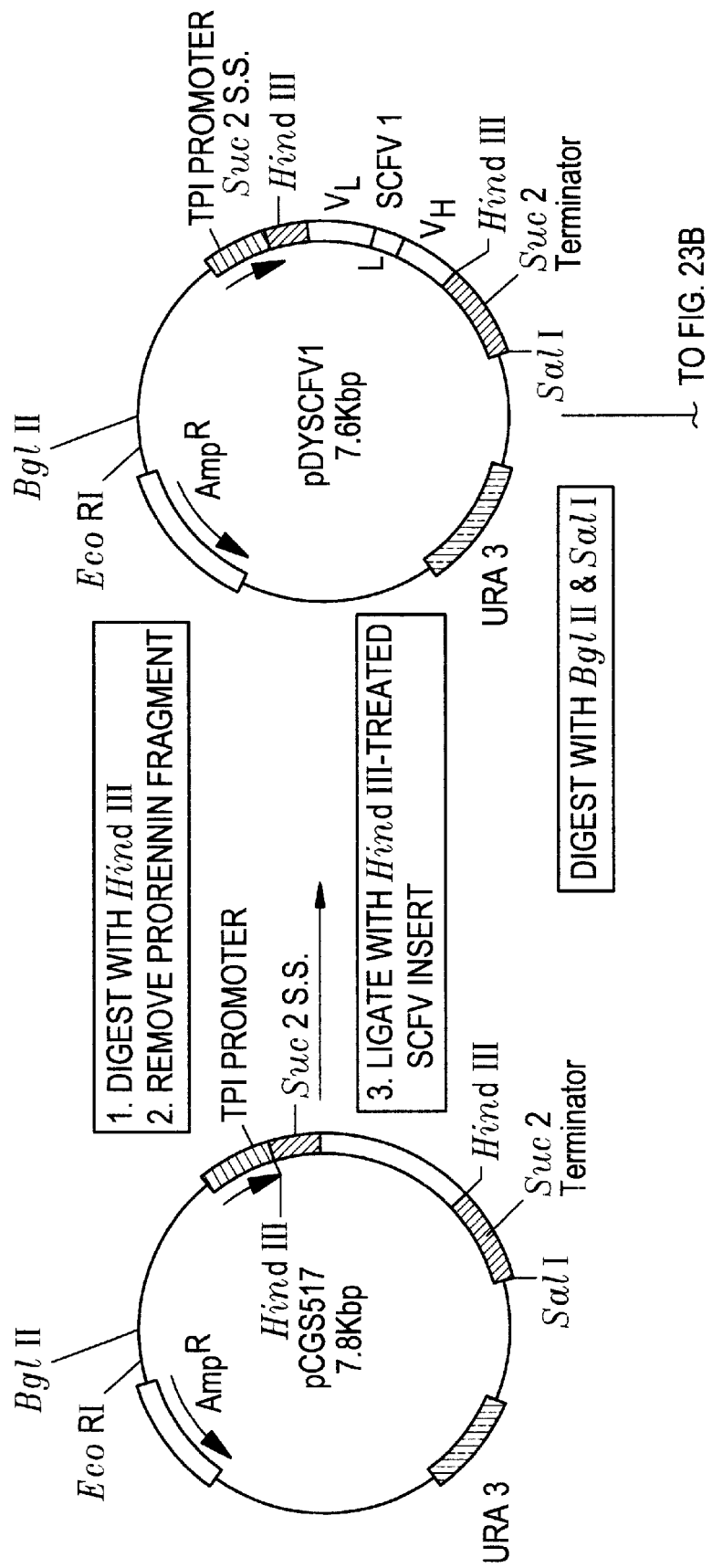
FIG. 23 shows the construction of plasmid pCGS515/SCFV1.
Figure 23B:
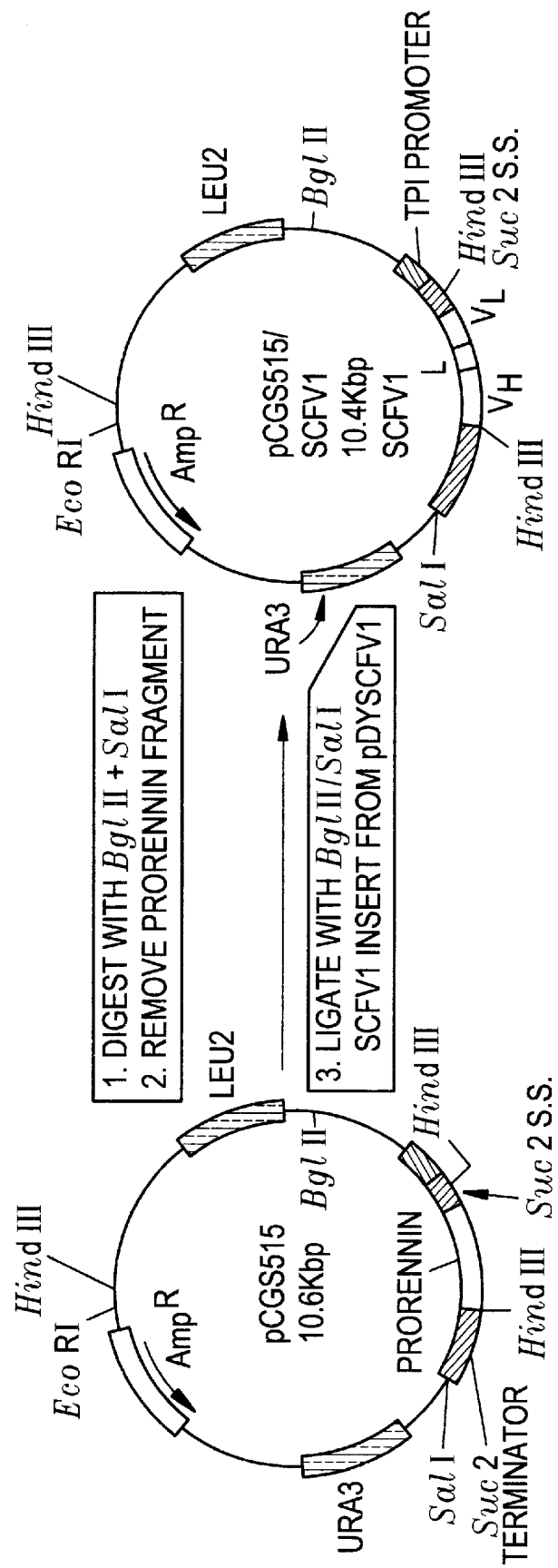

DNA from the vector and insert were digested in separate reactions with Bgl II and Sal I using 10×buffer number 3 (50 MM Tris-HCI (pH 8.0), 100 mM NaCl, BRL). The DNA fragment from pDYSCFV1 was run in and electroeluted from a 5 percent polyacrylamide gel and the insert DNA was run and electroeluted from a 3.75 percent polyacrylamide gel. A standard ligation using T4 DNA ligase (Stratagene, La Jolla, Calif.) and a transformation using *E. coli* DH1 (Invitrogen) was carried out. Out of 6 clones selected for screening with Bgl II and Sal I, all 6 were correctly oriented, and one was designated pCGS515/SCFV1 (FIG. 23).

DNA sequencing of pCGS515/SCFVI DNA was done using a Sequenase™ kit (U.S. Biochemical, Cleveland, Ohio) using pCGS515/SCFV1 DNA. The results have been presented in FIG. 22 and confirm the sequence expected, based on the linker, the Hum4 $V_L$ and the CC49 $V_H$.

Transformation of yeast cells using the autonomously replicating plasmid pCGS515/SCFV1 was carried out using the lithium acetate procedures described in Ito et al. (1983), *J. Bacteriol.*, 153:163–168; and Treco (1987), In: *Current Protocols in Molecular Biology*, Ausebel et al. (eds), 2:13.71–13.7.6. The recipient strain of *S. cerevisiae* was CGY1284 having the genotype—MAT α (mating strain α), ura 3-52 (uracil auxotrophy), SSC1-1 (supersecreting 1), and PEP4⁺ (peptidase 4 positive).

Transformed clones of CGY1284 carrying SCFV plasmids were selected by their ability to grow on minimal media in the absence of uracil. Transformed colonies appeared within 3 to 5 days. The colonies were transferred, grown and plated in YEPD medium. Shake flasks were used to provide culture supernatant with expressed product.

An ELISA procedure was used to detect biological activity of the SCFV1. The assay was set up such that the SCFV would compete with biotinylated CC49 (biotin-CC49) for binding to the TAG-72 antigen on the ELISA plate.

SCFV1 protein was partially purified from a crude yeast culture supernatant, using a Superose 12 gel filtration column (Pharmacia LKB Biotechnology), and found to compete with biotinylated CC49 in the competition ELISA. These results demonstrate that the SCFV1 had TAG-72 binding activity.

The SCFV1 protein was detected by a standard Western protocol (see Towbin et al. (1979), *Proc. Natl. Acad. Sci., USA,* 76:4350–4354). The detecting agent was biotinylated FAID14 (ATCC No. CRL 10256), an anti-idiotypic monoclonal antibody prepared from mice that had been immunized with CC49. A band was visualized that had an apparent molecular weight of approximately 26,000 daltons, the expected size of SCFV1. This result demonstrated that the SCFV1 had been secreted and properly processed.

Example 4

The following example demonstrates the cloning of human $V_H$ genes into a SCFV plasmid construct containing sequence coding for the Hum4 $V_L$ and a 25 amino acid linker called UNIHOPE.

Figure 24A:
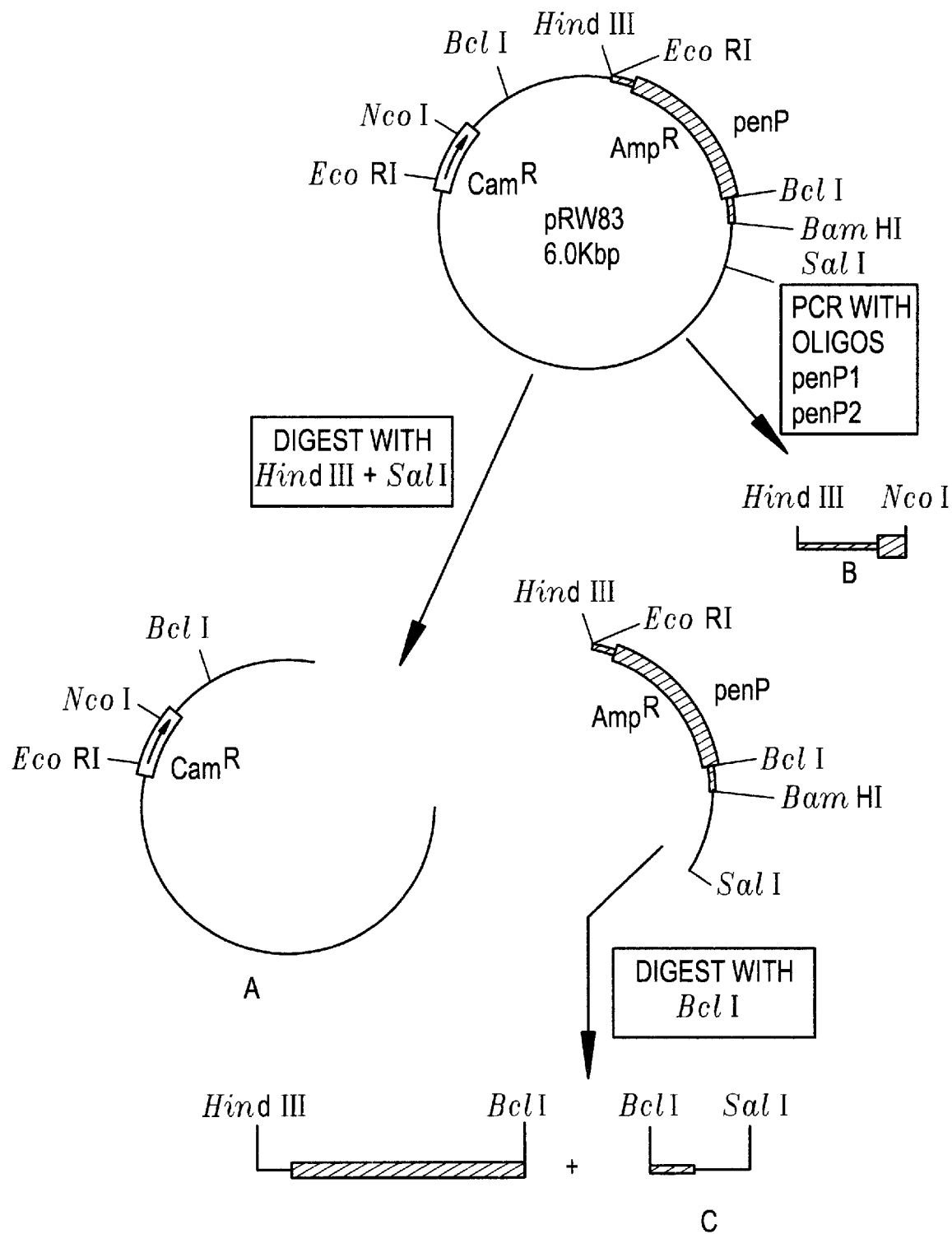
FIGS. 24A–24B show the construction of plasmid pSCFV31.
Figure 24B:
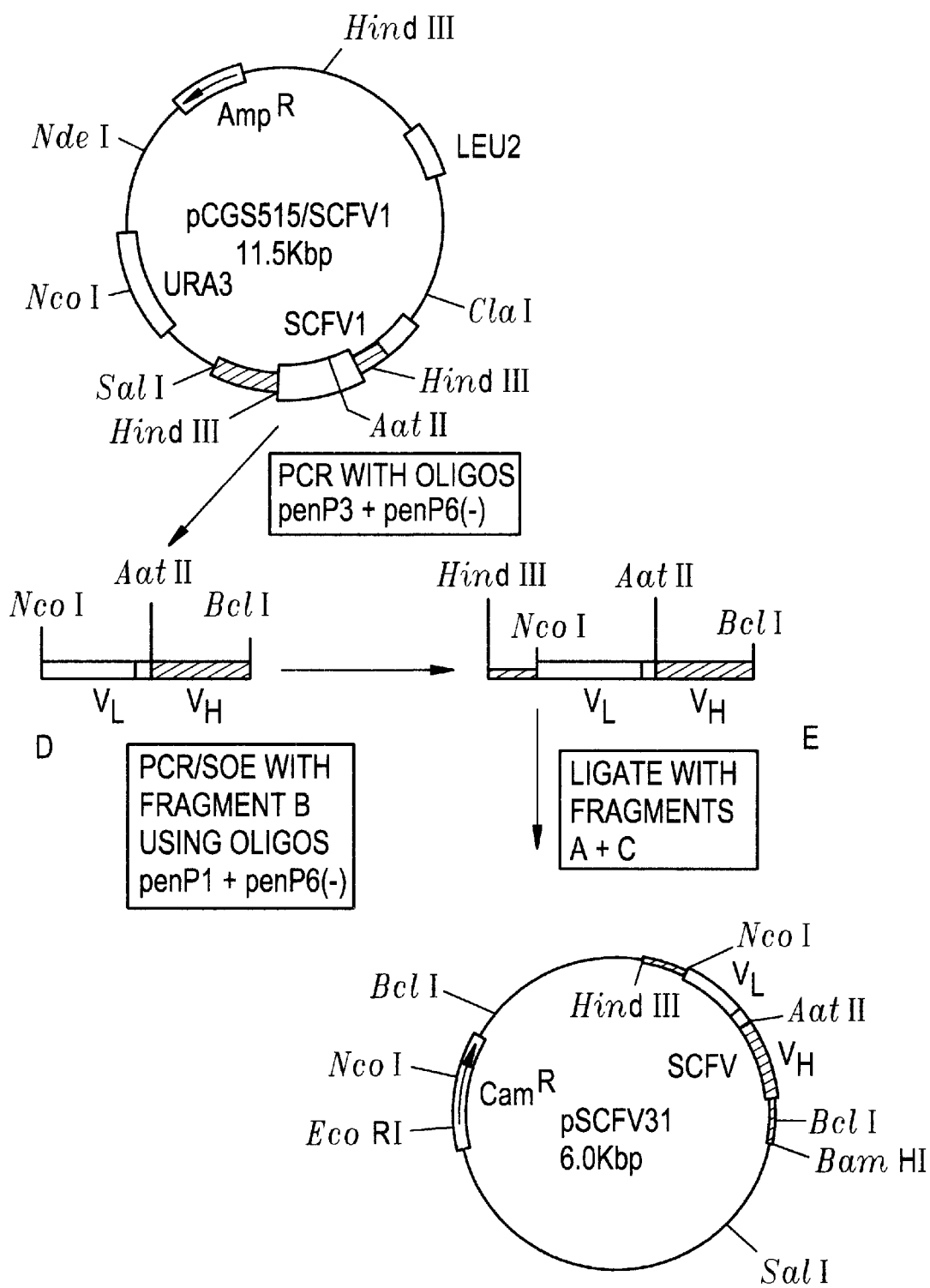

A vector was prepared from plasmid pRW 83 containing a chloramphenicol resistance ($Cam^r$) gene for clone selection, and a penP gene with a penP promoter and terminator (see Mezes, et al. (1983), *J. Biol. Chem.,* 258:11211–11218) and the pel B signal sequence (see Lei, et al. (1987), supra). The vector was designated Fragment A (see FIG. 24). The penP gene was removed with a Hind III/Sal I digest.

The penP promoter and pel B signal sequence were obtained by a PCR using pRW 83 as a template and oligonucleotides penP1 and penP2 as primers. The fragment was designated Fragment B (see FIG. 24). A Nco I enzyme restriction site was introduced at the 3' end of the signal sequence region by the penP2 oligonucleotide.

```
penP1:
5'-CGATAAGCTTGAATTCCATCACTTCC-3' penP2:
5'-GGCCATGGCTGGTTGGGCAGCGAGTAATAACAATCCAGCG GCT
GCCGTAGGCAATAGGTATTTCATCAAAATCGTCTCCCTCCGTTTGAA-3'
```

A SCFV comprised of a Hum4 $V_L$, a CC49 $V_H$, and an 18 amino acid linker (Lys Glu Ser Gly Ser Val Ser Ser Glu Gln Leu Ala Gln Phe Arg Ser Leu Asp) was obtained from pCGS515/SCFV1 by PCR using oligonucleotides penP3 and penP6. This fragment was designated Fragment D (see FIG. 24). A Bcl I site was introduced at the 3' end of the $V_H$ region by the penP6 oligonucleotide.

```
penP3:
5'-GCTGCCCAACCAGCCATGGCCGACATCGTGATGACCCAGTCTCC-3' penP6(-):
5'-CTCTTGATCACCAAGTGACTTTATGTAAGATGATGTTTTG ACG
GATTCATCGCAATGTTTTTATTTGCCGGAGACGGTGACTGAGGTTCC-3'.
```

Fragments B and D were joined by PCR using oligonucleotides penP1 and penP6, following the procedures of Horton et al., supra. The new fragment was designated E (See FIG. 24).

Fragment C containing the penP termination codon was isolated by digesting pRW 83 with Bcl I and Sal I, and designated Fragment C. pRW 83 was isolated from *E. coli* strain GM161, which is DNA methylase minus or dam⁻.

Plasmid pSCFV 31 (see FIG. 24) was created with a three part ligation Fragments A, C, and E.

The Nco I restriction enzyme site within the $Cam^r$ gene and the Hind III site located at the 5' end of the penP promoter in pSCFV 31 were destroyed through a PCR DNA amplification using oligonucleotides Nco1.1 and Nco1.3(-) to generate an Eco RI-Nco I fragment and oligonucleotides Nco1.2 and Nco1.4c(-) to generate a Nco I to Eco RI fragment. These two fragments were joined by PCR-SOE using oligonucleotides Nco1.1 and Nco1.4c(-). The oligonucleotides are set forth below:

```
Nco1.1:
5'-TCCGGAATTCCGTATGGCAATGA-3'

Nco1.3(-):
5'-CTTGCGTATAATATTTGCCCATCGTGAAAACGGGGGC-3'

Nco1.2:
5'-ATGGGCAAATATTATACGCAAG-3'

Nco1.4c(-):
5'-CACTGAATTCATCGATGATAAGCTGTCAAACATGAG-3'
``` pSCFV 31 was digested with Eco RI and the larger fragment was isolated by polyacrylamide gel electrophoresis. To prevent self ligation, the DNA was dephosphorylated using calf intestinal alkaline phosphatase according to the teachings of Sambrook et al., supra.

Figure 25A:
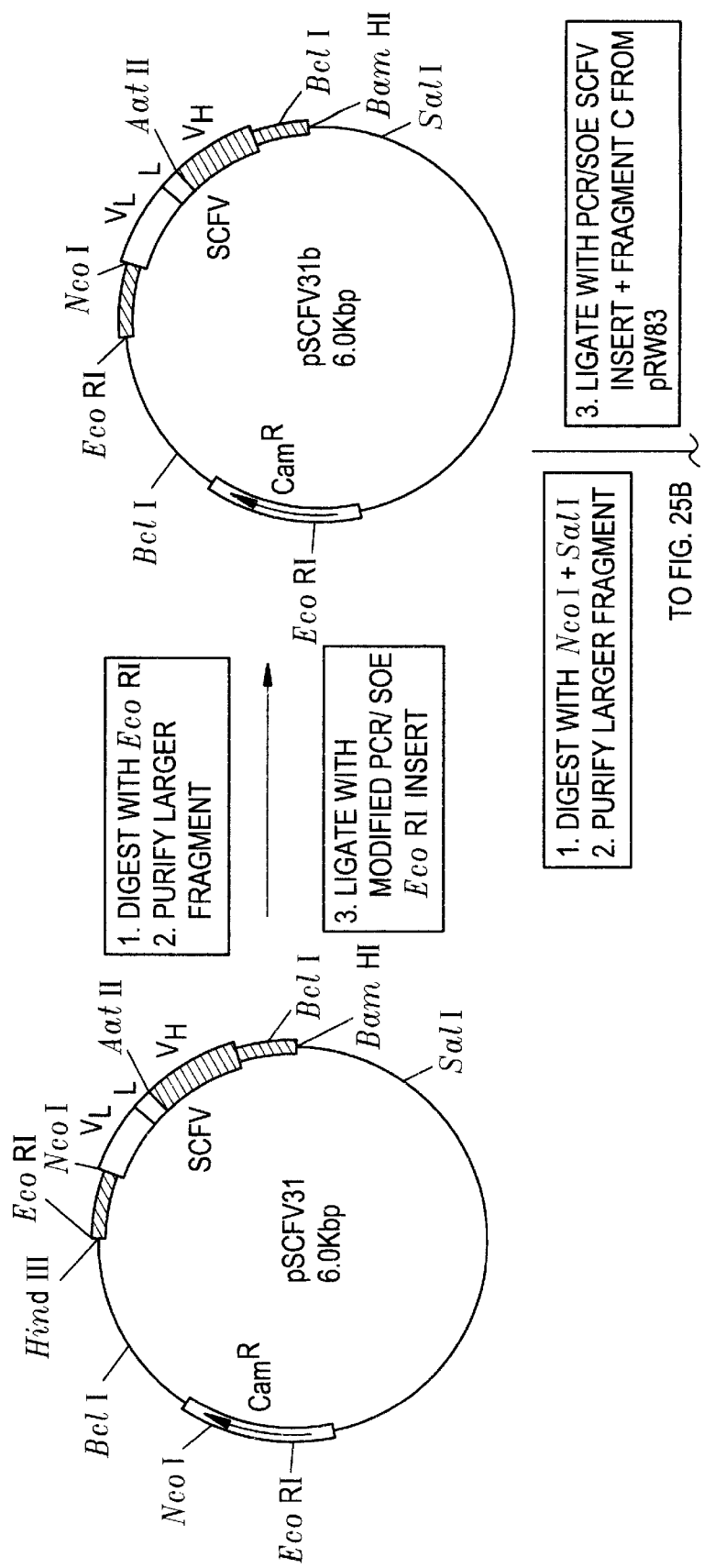
FIG. 25 shows the construction of E. coli SCFV expression plasmids containing Hum4 $V_L$.

A two part ligation of the larger pSCFV 31 digested fragment and the PCR-SOE fragment, described above, resulted in the creation of pSCFV 31b (see FIG. 25).

pSCFV 31b was digested with Nco I and Sal I and a fragment containing the $Cam^r$ gene was isolated.

The Hum4 $V_L$ was obtained by PCR DNA amplification using pCGS515/SCFV1 as a template and oligonucleotides 104BH1 and 104BH2(-) as primers.

```
104BH1:
5'-CAGCCATGGCCGACATCGTGATGACCCAGTCTCCA-3'

104BH2(-):
5'-AAGCTTGCCCCATGCTGCTTTAACGTTAGTTTTATCTGCTGG
AGACAGAGTGCCTTCTGCCTCCACCTTGGTCCCTCCGCCGAAAG-3'
```

The CC49 $V_H$ was obtained by PCR using p49 g1-2.3 (FIG. 6) as a template and oligonucleotides 104B3 and 104B4(-) as primers. A Nhe I enzyme restriction site was introduced just past the termination codon in the 3' end (before the Bcl I site) by oligonucleotide 104B4(-).

```
104B3:
5'-GTTAAAGCAGCATGGGGCAAGCTTATGACTCAGTTGCAGCAGTCTGACGC-3'
```

```
104B4(-):
5'-CTCTTGATCACCAAGTGACTTTATGTAAGATGATGTTTTGACGGATT

CATCGCTAGCTTTTTATTTGCCATAATAAGGGGAGACGGTGACTGAGGTTCC-3'
```

In the PCR which joined these two fragments using oligonucleotides 104BH1 and 104B4(-) as primers, a coding region for a 22 amino acid linker was formed.

A fragment C (same as above) containing the penP termination codon was isolated from pRW 83 digested with Bcl I and Sal I.

Plasmid pSCFV 33H (see FIG. 25) was created with a three part ligation of the vector, fragment C, and the SCFV fragment described above.

pSCFV 33H was digested with NcoI and NheI, and the DNA fragment containing the Cam$^r$ gene was isolated as a vector.

Hum4 $V_L$ was obtained by PCR DNA amplification using pRL1001 (see FIG. 18) as a template and oligonucleotides UNIH1 and UNIH2(-) as primers. Oligonucleotides for the PCR were:

```
UNIH1:
5'-CAGCCATGGCCGACATTGTGATGTCACAGTCTCC-3'
```

The Nco I site is in bold and the hybridizing sequence is underlined.

```
UNIH2(-):
5'-GAGGTCCGTAAGATCTGCCTCGCTACCTAGCAAA

AGGTCCTCAAGCTTGATCACCACCTTGGTCCCTCCGC-3'
```

The Hind III site is in bold.

The CC49 $V_H$ was obtained by a PCR using p49g1-2.3 (see FIG. 6) as a template and oligonucleotides UNI3 and UNI4(-) as primers.

```
UNI3:
5'-AGCGAGGCAGATCTTACGGACCTCGAGGTTCAGTTGCAGCAGTCTGAC-3'.
```

The Xho I site is in bold and the hybridizing sequence is underlined.

```
UNI4(-):
5'-CATCGCTAGCTTTTTATGAGGAGACGGTGACTGAGGTTCC-3'.
```

The Nhe I site is in bold and the hybridizing sequence is underlined.

Oligonucleotides UNIH1 and UNI4(-) were used in the PCR-SOE amplification which joined the Hum4 $V_L$ and CC49 $V_H$ fragments and formed a coding region for a negatively charged fifteen amino acid linker. The DNA as digested with Nhe I and Nco I and ligated with the vector fragment from the Nco I-Nhe I digest of pSCFV 33H. The resultant plasmid was designated pSCFV UNIH (shown in FIG. 25).

With the construction of pSCFV UNIH, a universal vector for any SCFV was created with all the desired restriction enzyme sites in place.

pSCFV UNIH was digested with Hind III/Xho I, and the large DNA fragment containing the Cam$^r$ gene, Hum4 $V_L$ and CC49 $V_H$ was isolated.

A fragment coding for a 25 amino acid linker, was made by annealing the two oligonucleotides shown below. The linker UNIHOPE is based on 205C SCA™ linker (see Whitlow, (1990) *Antibody Engineering: New Technology and Application Implications,* IBC USA Conferences Inc, Mass.), but the first amino acid was changed from serine to leucine and the twenty-fifth amino acid were was changed from glycine to leucine, to accommodate the Hind III and Xho I restriction sites. The nucleotide sequence of the single chain portion of pSCFV Unihope H is shown in FIG. 26. Structural sequences are indicated by the amino acid sequence written above the DNA sequence. The symbols → and ← indicate the beginning and end of a given segment. The amino acid sequence of the linker is boxed.

The nucleotide sequence encoding the linker UNIHOPE is set forth below:

```
UNIHOPE (FIG. 26):
5'-TATAAAGCTTAGTGCGGACGATGCGAAAAAGGATGCTGCGAAG

AAGGATGACGCTAAGAAAGACGATGCTAAAAAGGACCTCGAGTCTA-3'

UNIHOPE(-) (FIG. 26):
5'-TAGACTCGAGGTCCTTTTTAGCATCGTCTTTCTTAGCGTCAT

CCTTCTTCGCAGCATCCTTTTTCGCATCGTCCGCACTAAGCTTTATA-3'.
```

Figure 27:
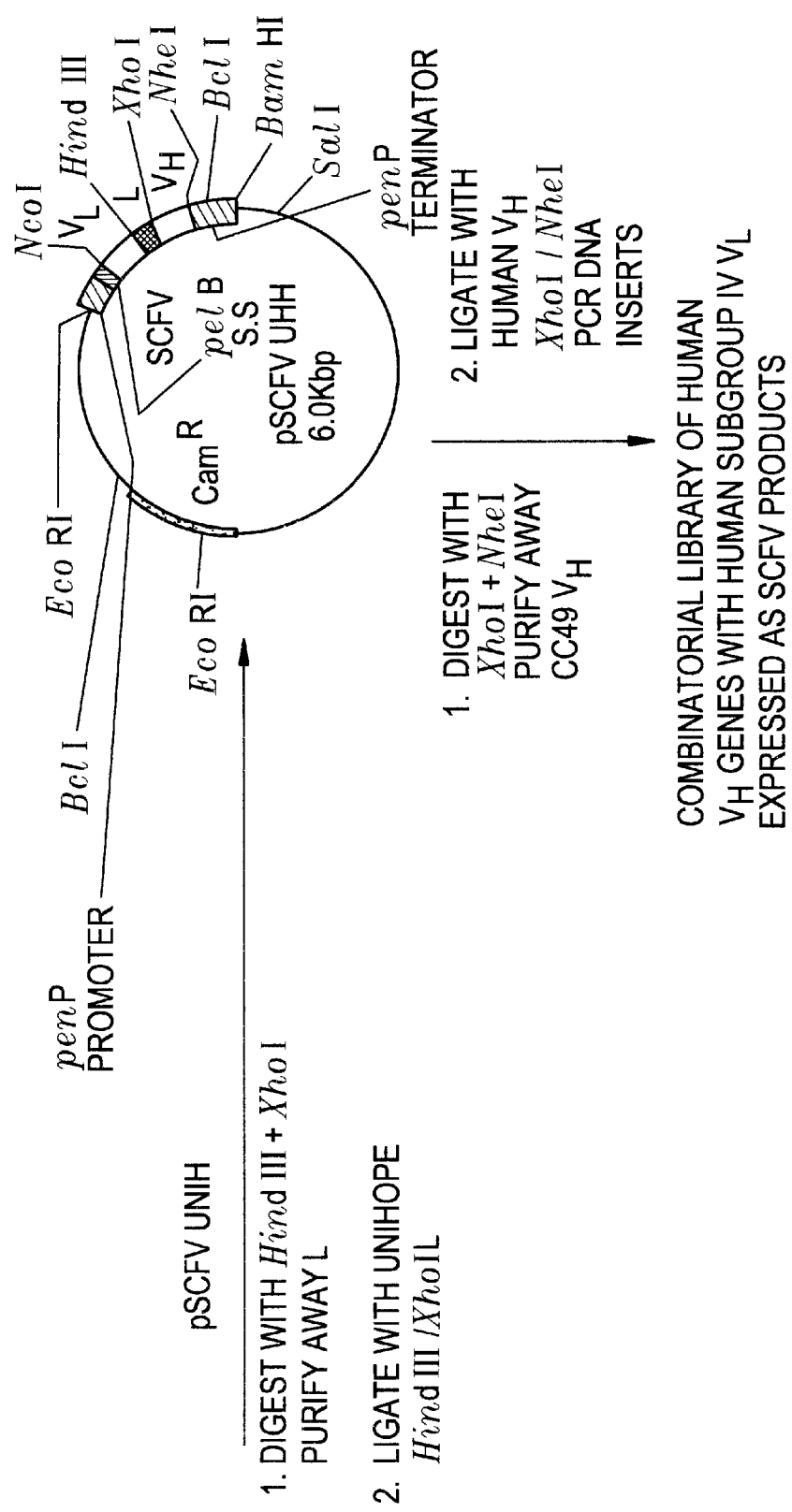
FIG. 27 shows the construction of plasmid pSCFV UHH and a schematic of a combinatorial library of $V_H$ genes with Hum4 $V_L$.

The resulting strand was digested with Hind III/Xho I and ligated into the vector, thus generating the plasmid pSCFV UHH (shown in FIG. 27). Plasmid pSCFV UHH expresses a biologically active, TAG-72 binding SCFV consisting of the Hum4 $V_L$ and CC49 $V_H$. The expression plasmid utilizes the β-lactamase penP promoter, pectate lyase pelB signal sequence and the penP terminator region. Different immunoglobulin light chain variable regions can be inserted in the Nco I-Hind III restriction sites, different SCFV linkers can be inserted in the Hind III-Xho I sites and different immunoglobulin heavy chain variable regions can be inserted in the Xho I-Nhe I sites.

*E. coli* AG1 (Stratagene) was transformed with the ligation mix, and after screening, a single chloramphenicol resistant clone, having DNA with the correct restriction map, was used for further work.

The DNA sequence and deduced amino acid sequence of the SCFV gene in the resulting plasmid are shown in FIG. 26.

*E. coli* AG1 containing pSCFV UHH were grown in 2 ml of LB broth with 20 μg/mL chloramphenicol (CAM 20). The culture was sonicated and assayed using a competition ELISA. The cells were found to produce anti-TAG-72 binding material. The competition assay was set up as follows: a 96 well plate was derivatized with a TAG-72 preparation from LS174T cells. The plate was blocked with 1% BSA in PBS for 1 hour at 31° C. and then washed 3 times. Twenty-five microliters of biotin CC49 (1/20,000 dilution of a 1 mg/mL solution) were added to the wells along with 25 μL of sample to be tested (competition step) and the plate was incubated for 30 minutes at 31° C. The relative amounts of TAG-72 bound to the plate, biotinylated CC49, streptavidin-alkaline phosphatase, and color development times were determined empirically in order not to have excess of either antigen or biotinylated CC49, yet have enough signal to detect competition by SCFV. Positive controls were CC49 at 5 μg/mL and CC49 Fab at 10 μL/mL. Negative controls were 1% BSA in PBS and/or concentrated LB. At the end of the competition step, unbound proteins were washed away.

Fifty microliters of a 1:1000 dilution of streptavidin conjugated with alkaline phosphatase (Southern Biotechnology Associates, Inc., Birmingham, Ala.) were added and the plate was incubated for 30 minutes at 31° C. The plate was washed 3 more times. Fifty microliters of a para-nitrophenylphosphate solution (Kirkegaard & Perry Laboratories, Inc., Gaithersburg, Md.) were added and the color reaction was allowed to develop for a minimum of 20 minutes. The relative amount of SCFV binding was measured by optical density scanning at 405–450 nm using a microplate reader (Molecular Devices Corporation, Menlo Park, Calif.). Binding of the SCFV resulted in decreased binding of the biotinylated CC49 with a concomitant decrease in color development. The average value for triplicate test samples is shown in the table below:

| Sample (50 µL) (mixed 1:1 with CC49 Biotin) | OD 405 nm - OD 450 nm Value at 50 minutes |
|---|---|
| Sonicate E.coli AG1/ pSCFVUHH clone 10 | 0.072 |
| Sonicate E.coli AG1/ pSCFVUHH clone 11 | 0.085 |
| CC49 at 5 mg/mL | 0.076 |
| CC49 Fab at 10 mg/mL | 0.078 |
| LB (negative control) | 0.359 |

The data indicates that there was anti-TAG-72 activity present in the *E. coli* AGI/pSCFVUHH clone sonicate.

Example 5

Figure 31A:
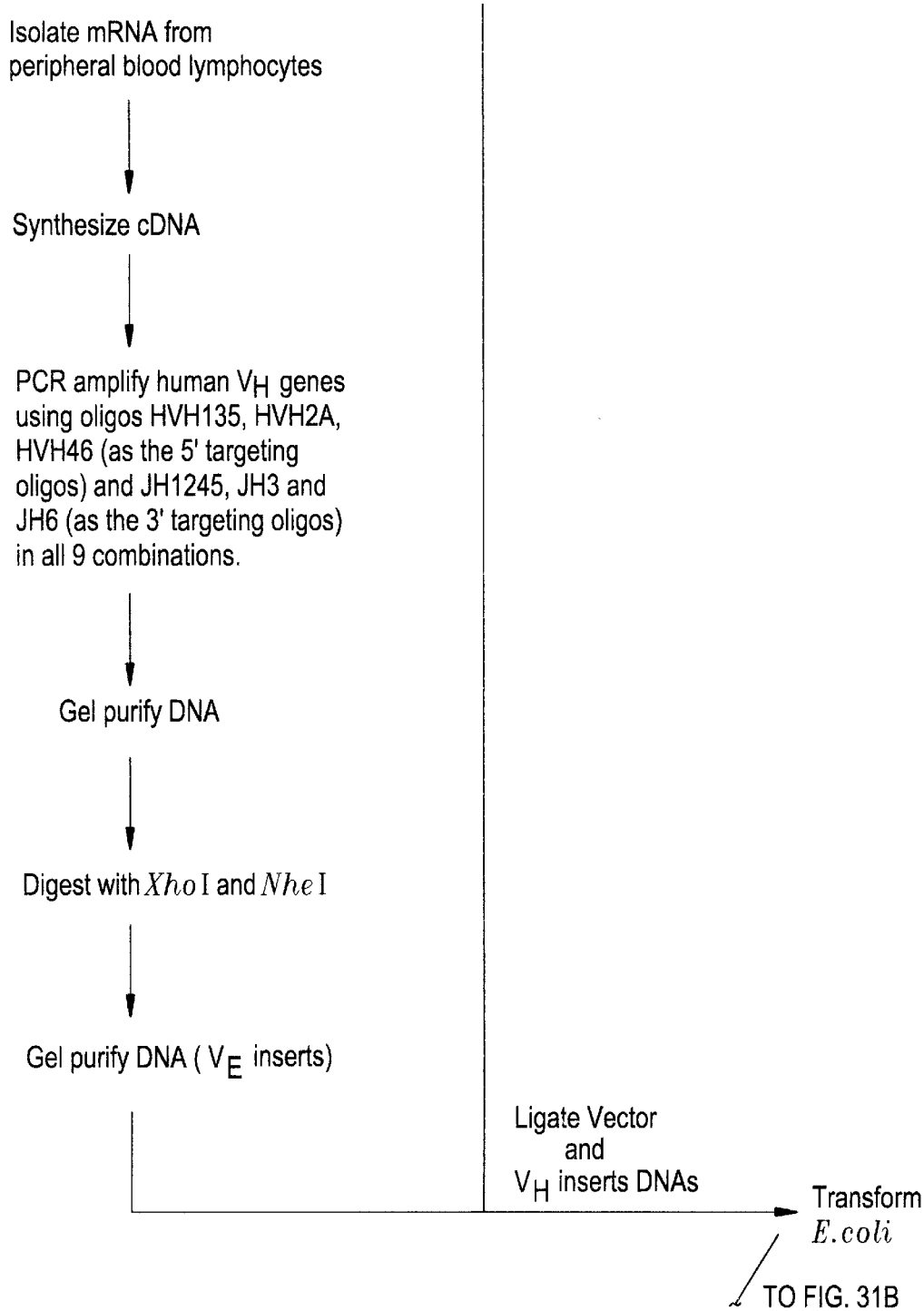

The plasmid pSCFVUHH may be used to host other $V_H$ genes on Xho I-Nhe I fragments and test in a SCFV format, following the procedures set forth below. A schematic for this process is shown in FIG. 31.

Isolating total RNA from peripheral blood lymphocytes:

Blood from a normal, healthy donor is drawn into three 5 mL purple-cap Vacutainer tubes. Seven mL of blood are added to two 15 mL polypropylene tubes. An equal volume of lymphoprep (cat#AN5501, Accurate) is added and the solution is mixed by inversion. Both tubes are centrifuged at 1000 rpm and 18° C. for 20 minutes. The resulting white area near the top of the liquid (area not containing red blood cells) is removed from each sample and placed into two sterile polypropylene centrifuge tube. Ten mL of sterile PBS are added and the tube mixed by inversion. The samples are centrifuged at 1500 rpm and 18° C. for 20 minutes Total RNA is isolated from resulting pellet according to the RNAzol B Method (Chomczynski and Sacchi (1987), *Analytical Biochemistry*, 162:156–159). Briefly, the cell pellets are lysed in 0.4 mL RNAzol solution (cat#:CS-105, Cinna/Biotecx). RNA is solubilized by passing the cell pellet through a 1 mL pipette tip. Sixty µL of chloroform are added and the solution is shaken for 15 seconds. RNA solutions are then placed on ice for 5 minutes. Phases are separated by centrifugation at 12000×g and 4° C. for 15 minutes. The upper (aqueous) phases are transferred to fresh RNase-free microcentrifuge tubes. One volume of isopropanol is added and the samples placed at –20° C. for 1 hour. The samples are then placed on dry ice for 5 minutes and finally centrifuged for 40 seconds at 14,000×g and 4° C. The resulting supernatant is removed from each sample and the pellet is dissolved in 144 µL of sterile RNase-free water. Final molarity is brought to 0.2 in NaCl. The DNA is reprecipitated by adding 2 volumes of 100% ethanol, leaving on dry ice for 10 minutes, and centrifugation at 14,000 rpm and 4° C. for 15 minutes. The supernatants are then removed, the pellets washed with 75% ethanol and centrifuged for 8 minutes at 12000×g and 4° C. The ethanol is then removed and the pellets dried under vacuum. The resulting RNA is then dissolved in 20 sterile water containing 1 µl RNasin (cat#:N2511, Promega).

cDNA synthesis:

cDNA synthesis is performed using a Gene Amp™ PCR kit (cat#: N808-0017 Perkin Elmer Cetus), RNasin™ (cat#: N2511, Promega), and AMV reverse transcriptase (cat#: M9004, Promega). The following protocol is used for each sample:

| Components | Amount |
|---|---|
| MgCl$_2$ solution | 4 µl |
| 10 × PCR buffer II | 2 µl |
| dATP | 2 µl |
| dCTP | 2 µl |
| dGTP | 2 µl |
| dTTP | 2 µl |
| 3' primer (random hexamers) | 1 µl |
| RNA sample | 2 µl |
| RNasin | 1 µl |
| AMV RT | 1.5 µl |

Samples are heated at 80° C. for 3 minutes then slowly cooled to 48° C. The samples are then centrifuged for 10 seconds. AMV reverse transcriptase is added to the samples which are then incubated for 30 minutes at 37° C. After incubation, 0.5 µl of each dNTP and 0.75 reverse transcriptase (cat#:109118, Boehringer Mannheim) are added. The samples are incubated for an additional 15 minutes at 37° C.

PCR Reaction:

Oligonucleotides are designed to amplify human $V_H$ genes by polymerase chain reaction. The 5' oligonucleotides are set forth below:

HVH 135:
5'-TATTCTCGAGGTGCA(AG)CTG(CG)TG(CG)AGTCTGG-3'

HVH2A:
5'-TATTCTCGAGGTCAA(CG)TT(AG)A(AG)GGAGTCTGG-3'

HVH46:
5'-TATTCTCGAGGTACAGCT(AG)CAG(CG)(AT)GTC(ACG)GG-3'

The 3' oligonucleotides are ser forth below:

JH1245:
5'-TTATGCTAGCTGAGGAGAC(AG)GTGACCAGGG-3'

JH3:
5'-TTATGCTAGCTGAAGAGACGGTGACCATTG

JH6:
5'-TTATGCTAGCTGAGGAGACGGTGACCGTGG-3'

PCR reactions are performed with a GeneAmp™ PCR kit (cat#:N808-0017, Perkin Elmer Cetus). Components are listed below:

| Components | Amount |
|---|---|
| ddH$_2$O | 75 µl |
| 10 × buffer | 10 µl |
| dATP | 2 µl |
| dCTP | 2 µl |
| dGTP | 2 µl |

-continued

| Components | Amount |
|---|---|
| dTTP | 2 μl |
| 1* Target DNA | 1 μl |
| 2* 5' primer | 2.5 μl |
| 3' primer | 2.0 μl |
| 3* AmpliTaq ™ Polymerase | 1.3 μl |

*components added in order at 92° C. of first cycle
PCR program:
step 1 94° C. for 30 seconds
step 2 60° C. for 1 minutes
step 3 72° C. for 45 seconds Approximately 35 cycles are completed for each reaction. All PCR reactions are performed using a Perkin Elmer Cetus PCR System 9600 thermal cycler.

Treatment of Human $V_H$ inserts with Xho I and Nhe I:

Human $V_H$ genes are digested with Xho I (cat#: 131L, New England Biolabs) and Nhe I (cat#: 146L, New England Biolabs). The following protocol is used for each sample:

| SUBSTANCE | AMOUNT |
|---|---|
| DNA | 20 μl |
| NEB Buffer #2 | 4.5 μl |
| Nhe I | 2 μl |
| Xho I | 2 μl |
| ddH$_2$O | 16.5 μl |

Samples are incubated at 37° C. for 1 hour. After this incubation, an additional 1.5 μL Nhe I is added and samples are incubated an additional two hours at 37° C.

Purification of DNA:

After the restriction enzyme digest, DNA is run on a 5 percent polyacrylamide gel (Sambrook et al. (1989), supra). Bands of 390–420 bp in size are excised from the gel. DNA is electroeluted and ethanol precipitated according to standard procedures.

PCR products resulting from oligonucleotide combinations are pooled together: JH1245 with HVH135, HVH2A and HVH46; JH3 with HVH135, HVH2A and HVH46; JH6 with HVH135, HVH2A and HVH46. The volume of the resulting pools are reduced under vacuum to 50 microliters. The pools are then purified from a 4 percent polyacrylamide gel (Sambrook et al. (1989), supra) to isolate DNA fragments. Bands resulting at 390–420 bp are excised from the gel. The DNA from excised gel slices is electroeluted according to standard protocols set forth in Sambrook, supra.

Isolation of pSCFVUHH Xho I/Nhe I Vector Fragment

Approximately 5 μg in 15 μL of pSCFVUHH plasmid is isolated using the Magic Mini-prep™ system (Promega). To this is added 5.4 μL OF 10×Buffer #2 (New England Biolabs), 45 units of Xho I (New England Biolabs), 15 units of Nhe I and 24 μL of ddH$_2$O. The reaction is allowed to proceed for 1 hour at 37° C. The sample is loaded on a 4% polyacrylamide gel, electrophoresed and purified by electroelution, as described earlier. The DNA pellet is dissolved in 20 μL of ddH$_2$O.

One hundred nanograms of pSCFVUHH digested with Xho I/Nhe I is ligated with a 1:1 molar ratio of purified human $V_H$ inserts digested with Xho I and Nhe I using T4 DNA ligase (Stratagene). Aliquots are used to transform competent E. coli AG1 cells (Stratagene) according to the supplier's instructions.

GVWP hydrophilic membranes (cat#GVWP14250, Millipore) are placed on CAM 20 LB agar plates (Sambrook et al., 1989). One membrane is added to each plate. Four hundred microliters of the E. coli AG1 transformation suspension from above are evenly spread over the surface of each membrane. The plates are incubated for 16 hours at 37° C.

Preparation of TAG-72-coated membranes:

A 1% dilution of partially purified tumor associated glycoprotein-72 (TAG-72) produced in LS174 T-cells is prepared in TBS (cat#28376, Pierce). Ten milliliters of the TAG dilution are placed in a petri plate (cat#8-757-14, Fisher) for future use. Immobilon-P PVDF transfer membranes (cat#SE151103, Millipore) are immersed in methanol. The membranes are then rinsed three times in sterile double distilled water. After the final wash, the excess water is allowed to drain. Each of the membranes are placed in 10 milliliters of dilute TAG-72. The membranes are incubated at ambient temperature from 1 hour with gentle shaking. After incubation, the membranes are blocked with Western blocking solution (25 mM Tris, 0.15 M NaCl, pH 7.6; 1% BSA) for about 1 hour at ambient temperature.

Blocking solution is drained from the TAG membranes. With the side exposed to TAG-72 facing up, the membranes are placed onto fresh CAM 20 plates. Resulting air pockets are removed. The bacterial membranes are then added, colony side up, to a TAG membrane. The agar plates are incubated for 24 to 96 hours at ambient temperatures.

The orientation of the TAG-72 and bacterial membranes are marked with permanent ink. Both membranes are removed from the agar surface. The TAG-72 membrane is placed in 20 ml of Western antibody buffer (TBS in 0.05% Tween-20, cat#P-1379, Sigma Chemical Co.; 1% BSA, cat#3203, Biocell Laboratories) containing 0.2 ng of CC49-Biotin probe antibody. The bacterial membranes are replaced on the agar surface in their original orientation and set aside. CC49-Biotin is allowed to bind to the TAG membranes for 1 hour at 31° C. with gentle shaking. The membranes are then washed three times with TTBS (TBS, 0.05% Tween-20) for 5 minutes on an orbital shaker at 300 rpm. Streptavidin alkaline phosphatase (cat#7100-04, Southern Biotechnology Associates) is added to Western antibody buffer to produce a 0.1% solution. The TAG-72 membranes are each immersed in 16 milliliters of the streptavidin solution and allowed to incubate for 30 minutes at 31° C. with gentle shaking. After incubation, the membranes are washed as previously described. A final wash is then performed using Western alkaline phosphate buffer (8.4 g NaCO$_3$, 0.203 g MgCl$_2$-H$_2$O, pH 9.8), for 2 minutes at 200 rpm at ambient temperature. To develop the membranes, Western blue stabilized substrate (cat#S384B, Promega) is added to each membrane surface. After 30 minutes at ambient temperatures, development of the membranes is stopped by rinsing the membranes three times with ddH$_2$O. The membranes are then photographed and clear zones are correlated with colonies on the hydrophilic membrane, set aside earlier. Colony(ies) are isolated for growth in culture and used to prepare plasmid DNA for sequencing characterization. Also, the protein product is isolated to evaluate specificity and affinity.

Identification of Hum4 $V_L$, human $V_H$ combinations using pATDFLAG.

In a second assay system, Hum4 $V_L$-human $V_H$ combinations are discovered that bind to TAG-72 according to the schematic, supra, except for the following a different plasmid vector, pATDFLAG, was used (see below): at the assay step, IBI MII antibody is used as a probe to detect any Hum4 $V_L$-$V_H$ SCFV combinations that have bound to the hydrophobic membrane coated with TAG-72 and a sheep anti-mouse Ig antibody conjugated to horseradish peroxidase (Amersham, Arlington Heights, Ill.) is used to detect any binding of the MII antibody to TAG-72.

Figure 29A:
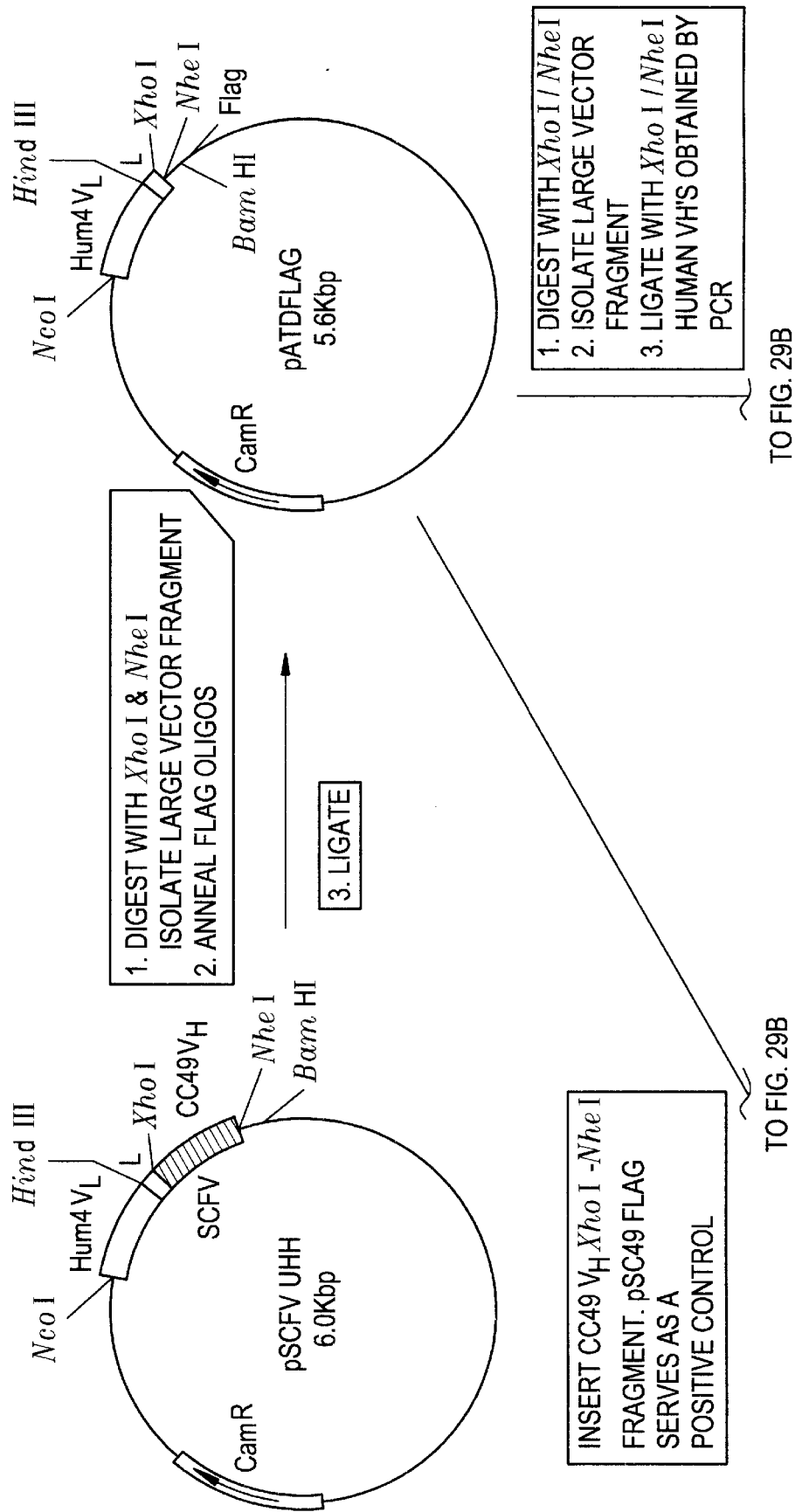
FIG. 29 illustrates the construction of pATDFLAG, pHumVL-HumVH (X) and pSC49FLAG.

The plasmid pATDFLAG was generated from pSCFVUHH (see FIG. 29) to incorporate a Flag-coding sequence 3' of any human $V_H$ genes to be expressed contiguously with Hum4 $V_L$. The plasmid pATDFLAG, when digested with Xho I and Nhe I and purified becomes the human $V_H$ discovery plasmid containing Hum4 $V_L$ in this SCFV format. The plasmid pATDFLAG was generated as follows. Plasmid pSCFVUHH treated with Xho I and Nhe I (isolated and described above) was used in a ligation reaction with the annealed FLAG and FLAGNC oligonucleotides.
FLAGC:
5'-TCGAGACAATGTCGCTAGCGACTACAAG ACGATGATGACAAATAAAAAC-3' FLAGNC:
5'-CTAGGTTTTTATTTGTCATCATCGTCCT TGTAGTCGCTAGCGACATTGTC-3'

Equimolar amounts ($1\times10^{-10}$ moles of each of the oligonucleotides FLAGC and FLAGNC were mixed together using a ligation buffer (Stratagene). The sample is heated to 94° C. and is allowed to cool to below 35° C. before use in the ligation reaction below.
Ligation Reaction to Obtain pATDFLAG

| COMPONENT | AMOUNT |
| --- | --- |
| pSCFVUHH Xho I/Nhe I vector | 1.5 μl |
| ANNEALED FLAGC/FLAGNC | 0.85 μl |
| 10 × Ligation buffer | 2 μl |
| T4 DNA LIGASE | 1 μl |
| 10 MM ATP | 2 μl |
| ddH$_2$O | 12.65 μl |

This ligation reaction is carried out using the following components and amounts according to the ligation protocol disclosed above. E. coli AG1 cells (Stratagene) are transformed with 3 μl of the above ligation reaction and colonies selected using CAM 20 plates. Clones having appropriate Nhe I, Xho I and Nhe I/Xho I restriction patterns are selected for DNA sequencing.

The oligonucleotide used to verify the sequence of the FLAG linker in pATDFLAG (see FIG. 28) is called PENPT-SEQ: 5'-CTTTATGTAAGATGATGTTTTG-3'. This oligonucleotide is derived from the non-coding strand of the penP terminator region. DNA sequencing is performed using Sequenase™ sequencing kit (U.S. Biochemical, Cleveland, Ohio) following the manufacturer's directions. The DNA and deduced amino acid sequences of the Hum4 $V_L$—UNIHOPE linker—FLAG peptide of pATDFLAG is shown in FIG. 28.
Generation of pSC49FLAG The CC49$V_H$ is inserted into the sites of Xho I-Nhe I pATDFLAG (see FIG. 29) and evaluated for biological activity with the purpose of serving as a positive control for the FLAG assay system to detect binding to TAG-72. The new plasmid, called pSC49FLAG (see FIG. 29) is generated as follows. The plasmid pATDFLAG (5 mg, purified from a 2.5 ml culture by the Magic Miniprep™ system (Promega) is treated with Xho I and Nhe I and the large vector fragment purified as described above for pSCFVUHH. The CC49 $V_H$ insert DNA fragment is obtained by PCR amplification from pSCFVUHH and oligonucleotides UNI3 as the 5' end oligonucleotide and SC49FLAG as the 3' end oligonucleotide. The resulting DNA and amino acid sequences of this SCFV antibody, with the FLAG peptide at the C-terminus, is shown in FIG. 30. The PCR reaction is carried out using 100 pmol each of the oligonucleotides, 0.1 ng of pSCFVUHH target DNA (uncut) and the standard protocol and reagents provided by Perkin Elmer Cetus. The DNA is first gel purified, then treated with Xho I and Nhe I to generate sticky ends and purified from a 4% polyacrylamide gel and electroeluted as described earlier. The DNA vector (pATDFLAG treated with Xho I and Nhe I) and the insert (CC49 $V_H$ PCR product from pSCFVUHH treated with Xho I and Nhe I) are ligated in a 1:1 molar ratio, using 100 ng vector DNA (Stratagene kit) and used to transform E. coli AG1 competent cells (Stratagene) according to the manufacturer's directions. A colony with the correct plasmid DNA is picked as the pSC49FLAG clone.
Ligation of pATDFLAG Vector with PCR Amplified Human $V_H$ Inserts The protocol for the ligation reaction is as follows:

| COMPONENT | AMOUNT |
| --- | --- |
| DNA vector:pATDFLAG Xho I/Nhe I | 2.5 μL |
| Hum $V_H$ (X) DNA inserts: Xho I/Nhe I | 6 μL |
| 10 mM ATP (Stratagene) | 2 μL |
| 10 × buffer (Stratagene) | 2 μL |
| T4 DNA ligase (Stratagene) | 1 μL |
| ddH$_2$O | 6.5 μL |

DNA vector, ATP, 10×buffer and ddH$_2$O are combined. DNA insert and T4 DNA ligase are then added. Ligation reactions are placed in a 4 L beaker containing H$_2$O at 18° C. The temperature of the water is gradually reduced by refrigeration at 4° C. overnight. This ligation reaction generates pHum4 $V_L$-hum $V_H$ (X) (See FIG. 29).
Transformation of E. coli AG1 with pHum4 $V_L$-Hum $V_H$ (X) Ligation Mix Transformation of pATDFLAG into competent E. coli AG1 cells (Stratagene) is achieved following the supplier's protocol.
IBI MII Anti-FLAG Antibody Plate Assay The first three steps, preparation of TAG-coated membranes, plating of bacterial membranes, and assembly of TAG and bacterial membranes, are the same as those described in the CC49-Biotin Competition Plate Assay.

After the 24 hour incubation at ambient temperatures, the membranes are washed with TTBS three times at 250 rpm for four minutes. The MII antibody (cat#IB13010, International Biotechnologies, Inc.) is then diluted with TBS to a concentration ranging from 10.85 μg/ml to 0.03 μg/ml. Ten milliliters of the diluted antibody are added to each membrane. The membranes are then incubated for 1 hour at ambient temperatures and shaken on a rotary shaker at 70 rpm. After incubation, the MII antibody is removed and the membranes are washed three times at 250 rpm and ambient temperatures for 5 minutes. The final wash is removed and 20 milliliters of a 1:2000 dilution of sheep anti-mouse horseradish peroxidase linked whole antibody (cat#NA931, Amersham) is prepared with TBS and added to each membrane. The membranes are again incubated for 1 hour at ambient temperatures and 70 rpm. Following incubation, the membranes are washed three times at 250 rpm and ambient temperature for 5 minutes each. Enzygraphic Webs (cat#IB8217051, International Biotechnologies, Inc.) are used to develop the membranes, according to the manufacturer's instructions. The membranes are then photographed.

Instead of seeing a clear zone on the developed membrane for a positive Hum4 $V_L$-$V_H$ (X) clone producing an SCFV that binds to TAG-72, (as seen with the competition screening assay) in this direct FLAG—detecting assay, a blue-purple spot is indicative of a colony producing a SCFV that has bound to the TAG-72 coated membrane. The advantage of using the FLAG system is that any Hum4 $V_L$-$V_H$ SCFV combination that has bound to TAG-72 will be detected. Affinities can be measured by Scatchard analysis (Scatchard (1949), supra) and specificity by immunohistochemistry. These candidates could then be checked for binding to a specific epitope by using the competition assay, supra, and a competing antibody or mimetic, if desired.

The present invention is not to be limited in scope by the cell lines deposited since the deposited embodiment is intended for illustration only and all cell lines which are functionally equivalent are within the scope of the invention. Indeed, while this invention has been described in detail and with reference to specific embodiments thereof, various changes and modifications could be made therein without departing from the spirit and scope of the appended claims.

What is claimed is:

1. A cell capable of expressing a Hum4 $V_L$, $V_H$ antibody or antibody fragment having binding affinity for TAG-72, said antibody or fragment comprising at least one light chain variable region ($V_L$) and at least one heavy chain variable region ($V_H$) wherein
   (A) the $V_L$ is a human kappa Subgroup IV $V_L$ encoded by the human Subgroup IV germline gene (Hum4 $V_L$) or by one of the effectively homologous human kappa Subgroup IV genes or DNA sequences thereof, the $V_L$ comprising human complementarity determining regions (CDRs) and comprising human kappa Subgroup IV framework regions;
   (B) the $V_H$ is an anti-TAG-72 $V_H$ encoded by the $V_H\alpha$TAG germline gene or one of its productively rearranged anti-TAG-72 $V_H$-encoding derivatives, or by one of the at least 80% homologous anti-TAG-72 $V_H$-encoding genes or DNA sequences thereof, said $V_H$ being capable of combining with said $V_L$ to form a three dimensional structure having the ability to bind TAG-72;

said cell being transformed with
   (C) a first DNA sequence encoding said $V_L$; and
   (D) a second DNA sequence encoding said $V_H$.

2. The cell of claim 1, wherein the first and second DNA sequences are contained within at least one biologically functional expression vector.

3. The cell of claim 1 wherein the Hum4 $V_L$, $V_H$ antibody or fragment has, as at least one $V_H$ thereof, a $V_H$ derived from a heavy chain of CC46, CC49, CC83, or CC92.

4. The cell of claim 1 wherein the Hum4 $V_L$, $V_H$ antibody or fragment is MP1-44H produced by a cell line having the identifying characteristics of ATCC HB 10426 or MP1-84H produced by a cell line having the identifying characteristics of ATCC HB 10427.

5. The cell of claim 1 wherein the anti-TAG-72 $V_H$ of the Hum4 $V_L$, $V_H$ antibody or fragment comprises (1) complementarity determining regions (CDRs) encoded by the $V_H\alpha$TAG germline gene or one of its productively rearranged anti-TAG-72 $V_H$-encoding derivatives, or by one of the effectively homologous anti-TAG-72 $V_H$-encoding genes or DNA sequences thereof; and (2) framework regions encoded by a human gene.

6. The cell of claim 1 wherein the Hum4 $V_L$, $V_H$ antibody or fragment has, as each light chain thereof, one said $V_L$ covalently attached to a human light chain constant domain ($C_L$) and has, as each heavy chain thereof, one said $V_H$ covalently attached to at least one animal heavy chain constant domain ($C_H$).

7. The cell of claim 6 wherein the Hum4 $V_L$, $V_H$ antibody or fragment thereof has the $C_H$ selected from the group consisting of $IgG_{1-4}$, IgM, IgA1, IgA2, IgD or IgE.

8. A process for producing a Hum4 $V_L$, $V_H$ antibody or antibody fragment said fragment comprising at least the variable domains of the antibody's heavy and light chains, in a single host cell, the process comprising the steps of:
   (A) transforming at least one host cell with
      i) a first DNA sequence encoding a human kappa Subgroup IV light chain variable region ($V_L$), which DNA sequence is effectively homologous to the human Subgroup IV germline gene, and
      ii) a second DNA sequence encoding an anti-TAG-72 heavy chain variable region ($V_H$) which is capable of combining with the $V_L$ to form a three dimensional structure having the ability to bind TAG-72, and
   (B) independently expressing said first DNA sequence and said second DNA sequence in said transformed host cell.

9. The process according to claim 8 wherein said first and second DNA sequences are present in at least one vector.

10. The process according to claim 9 wherein the antibody heavy and light chains of the Hum4 $V_L$, $V_H$ antibody or fragment thereof are expressed in the host cell are secreted therefrom as an immunologically functional antibody molecule or antibody fragment.

11. The process of claim 8, wherein the second DNA sequence encodes the $V_H$ of CC46, CC49, CC83 or CC92.

12. A process for preparing an antibody or antibody fragment conjugate which comprises contacting with an imaging marker or therapeutic agent:
   a Hum4 $V_L$, $V_H$ antibody or antibody fragment having binding affinity for TAG-72 and comprising at least one light chain variable region ($V_L$) and at least one heavy chain variable region ($V_H$) wherein
   (A) the $V_L$ is a human kappa Subgroup IV $V_L$ encoded by the human Subgroup IV germline gene or by one of the effectively homologous human kappa Subgroup IV genes or DNA sequences thereof, the $V_L$ comprising human complementarity determining regions (CDRs) and comprising human kappa Subgroup IV framework regions; and
   (B) the $V_H$ is an anti-TAG-72 $V_H$ encoded by the $V_H\alpha$TAG germline gene or one of its productively rearranged anti-TAG-72 $V_H$-encoding derivatives, or by one of the at least 80% homologous anti-TAG-72 $V_H$-encoding genes or DNA sequences thereof, said $V_H$ being capable of combining with said $V_L$ to form a three dimensional structure having the ability to bind TAG-72; and
   wherein said Hum4 $V_L$, $V_H$ antibody or fragment is produced according to the process of any one of claims 8–11.

13. A process for preparing an antibody or antibody fragment conjugate which comprises contacting with an imaging marker or therapeutic agent:
   a Hum4 $V_L$, $V_H$ antibody or antibody fragment having binding affinity for TAG-72 and comprising at least one light chain variable region ($V_L$) and at least one heavy chain variable region ($V_H$) wherein
   (A) the $V_L$ is a human kappa Subgroup IV $V_L$ encoded by the human Subgroup IV germline gene (Hum4 $V_L$) or by one of the effectively homologous human kappa Subgroup IV genes or DNA sequences thereof, the $V_L$ comprising human complementarity determining regions (CDRs) and comprising human kappa Subgroup IV framework regions; and (B) the $V_H$ is an anti-TAG-72 $V_H$ encoded by the $V_H\alpha$TAG germline gene or one of its productively rearranged anti-TAG-72 $V_H$-encoding derivatives, or by one of the at least 80% homologous anti-TAG-72 $V_H$-encoding genes or DNA sequences thereof, said $V_H$ being capable of combining with said $V_L$ to form a three dimensional structure having the ability to bind TAG-72.

14. The process of claim 13, wherein the imaging marker is $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re, $^{188}$Re or $^{99m}$Tc.

15. The process of claim 13, wherein the therapeutic agent is a radionuclide, drug or biological response modifier, toxin or another antibody.

16. The process of claim 13 wherein the Hum4 $V_L$, $V_H$ antibody or fragment has the $V_H$ derived from the variable regions of CC46, CC49, CC83 or CC92.

17. The process of claim 13 wherein the Hum4 $V_L$, $V_H$ antibody or fragment has the $V_H$ comprising (1) complementarity diversity regions (CDRs) encoded by a gene from the $V_H\alpha$TAG, and (2) framework segments, adjacent to the CDR segments, encoded by a human gene.

18. The process of claim 13 wherein the Hum4 $V_L$, $V_H$ antibody or fragment has, as each light chain thereof, one said $V_L$ covalently attached to a human light chain constant domain ($C_L$) and has, as each heavy chain thereof, one said $V_H$ covalently attached to at least one animal heavy chain constant domain ($C_H$).

19. The process of claim 18 wherein the Hum4 $V_L$, $V_H$ antibody or fragment thereof has the $C_H$ selected from the group consisting of IgG$_{1-4}$, IgM, IgA1, IgA2, IgD or IgE.

* * * * *